US012268584B2

(12) United States Patent
Carrillo Ojeda et al.

(10) Patent No.: US 12,268,584 B2
(45) Date of Patent: Apr. 8, 2025

(54) THREE-DIMENSIONAL NONWOVEN MATERIALS AND METHODS OF MANUFACTURING THEREOF

(71) Applicant: Kimberly-Clark Worldwide, Inc., Neenah, WI (US)

(72) Inventors: Antonio J. Carrillo Ojeda, Appleton, WI (US); Davis Dang H. Nhan, Menasha, WI (US); Neil T. Scholl, Neenah, WI (US); Vasily A. Topolkaraev, Appleton, WI (US); David G. Biggs, New London, WI (US); Patrick D. Abney, Menasha, WI (US); Jonathan A. Baker, Appleton, WI (US); Mark M. Mleziva, Appleton, WI (US); Steven J. Roffers, Neenah, WI (US); Dustin J. Smith, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 893 days.

(21) Appl. No.: 17/295,670

(22) PCT Filed: Nov. 27, 2019

(86) PCT No.: PCT/US2019/063546
§ 371 (c)(1),
(2) Date: May 20, 2021

(87) PCT Pub. No.: WO2020/112960
PCT Pub. Date: Jun. 4, 2020

(65) Prior Publication Data
US 2022/0008262 A1    Jan. 13, 2022

Related U.S. Application Data

(60) Provisional application No. 62/773,529, filed on Nov. 30, 2018.

(51) Int. Cl.
*A61F 13/511* (2006.01)
*A61F 13/15* (2006.01)
(Continued)

(52) U.S. Cl.
CPC .. *A61F 13/51104* (2013.01); *A61F 13/15577* (2013.01); *A61F 13/15699* (2013.01);
(Continued)

(58) Field of Classification Search
CPC ...... A61F 13/512; A61F 13/15; A61F 13/475; A61F 13/494; A61F 13/511;
(Continued)

(56) References Cited

U.S. PATENT DOCUMENTS 2,862,251 A * 12/1958 Kalwaites ............... D04H 1/49
162/286
2,958,608 A   11/1960 Barnard
(Continued)

FOREIGN PATENT DOCUMENTS

CA    2022080 A1    1/1992
CA    2133299 C     7/1999
(Continued)

OTHER PUBLICATIONS

Beaumont, Donald F. and Dr. Kenneth R. Randall, "Rotary Hydraulic Entanglement of Nonwovens," Nonwovens World, vol. 1, No. 3, Nov. 1986, pp. 76-80, reprinted from Insight 86 International Advanced Forming/Bonding Conference.
(Continued)

*Primary Examiner* — Michele Kidwell
(74) *Attorney, Agent, or Firm* — KIMBERLY-CLARK WORLDWIDE, INC.

(57) ABSTRACT

Three dimensional nonwoven materials and absorbent articles comprising such materials are disclosed. In one embodiment, an absorbent article may comprise an outer
(Continued)

cover, a bodyside liner, an absorbent body, and a nonwoven material coupled to the bodyside liner. The nonwoven material may comprise an apertured zone providing a percent open area for the apertured zone that is greater than about 15%. The nonwoven material may be coupled to liner by a front waist bond forming a front waist bonding region which extends through the apertured zone and a rear waist bond forming a rear waist bonding region, wherein the rear waist bonding region has a length that is between about 2% and about 10% of the material length and the front waist bonding region has a length that is between about 20% and about 50% of the material length.

19 Claims, 31 Drawing Sheets

(51) Int. Cl.
| | |
|---|---|
| *A61F 13/475* | (2006.01) |
| *A61F 13/49* | (2006.01) |
| *A61F 13/494* | (2006.01) |
| *A61F 13/512* | (2006.01) |
| *A61F 13/513* | (2006.01) |
| *B32B 3/26* | (2006.01) |
| *B32B 3/30* | (2006.01) |
| *B32B 5/02* | (2006.01) |
| *B32B 5/12* | (2006.01) |
| *D04H 1/495* | (2012.01) |
| *B32B 5/24* | (2006.01) |

(52) U.S. Cl.
CPC ...... *A61F 13/15731* (2013.01); *A61F 13/475* (2013.01); *A61F 13/49* (2013.01); *A61F 13/494* (2013.01); *A61F 13/51121* (2013.01); *A61F 13/5116* (2013.01); *A61F 13/512* (2013.01); *A61F 13/5121* (2013.01); *A61F 13/5125* (2013.01); *A61F 13/5126* (2013.01); *A61F 13/513* (2013.01); *B32B 3/266* (2013.01); *B32B 3/30* (2013.01); *B32B 5/022* (2013.01); *B32B 5/12* (2013.01); *D04H 1/495* (2013.01); *A61F 2013/15284* (2013.01); *A61F 2013/15829* (2013.01); *A61F 2013/1591* (2013.01); *A61F 2013/15934* (2013.01); *A61F 2013/15983* (2013.01); *A61F 2013/51165* (2013.01); *B32B 5/24* (2013.01); *B32B 2555/02* (2013.01); *D10B 2401/06* (2013.01); *D10B 2401/063* (2013.01); *D10B 2509/02* (2013.01); *D10B 2509/026* (2013.01); *Y10T 428/24124* (2015.01); *Y10T 428/24182* (2015.01); *Y10T 428/24298* (2015.01); *Y10T 428/24322* (2015.01); *Y10T 428/24331* (2015.01); *Y10T 442/689* (2015.04)

(58) Field of Classification Search
CPC ............. A61F 13/513; A61F 13/5116; A61F 13/5123; D04H 1/495; B32B 5/02; B32B 3/30; B32B 5/12; B32B 3/26; B32B 5/24
See application file for complete search history.

(56) References Cited

U.S. PATENT DOCUMENTS

| | | | |
|---|---|---|---|
| 3,014,263 A | 12/1961 | Oace | |
| 3,081,512 A | 3/1963 | Griswold | |
| 3,081,515 A | 3/1963 | Griswold et al. | |
| 3,095,878 A | 7/1963 | Bassett | |
| 3,193,436 A | 7/1965 | Kalwaites | |
| 3,218,381 A | 11/1965 | Such et al. | |
| 3,240,657 A | 3/1966 | Hynek | |
| 3,330,009 A | 7/1967 | Hynek | |
| 3,345,243 A | 10/1967 | Kalwaites | |
| 3,413,182 A | 11/1968 | Simons | |
| 3,485,706 A | 12/1969 | Evans | |
| 3,485,708 A | 12/1969 | Jack et al. | |
| 3,498,874 A | 3/1970 | Franklin et al. | |
| 3,623,935 A | 11/1971 | Allman et al. | |
| 3,679,535 A | 7/1972 | Frank | |
| 3,679,536 A | 7/1972 | Frank | |
| 3,681,183 A | 8/1972 | Frank | |
| 3,717,532 A | 2/1973 | Kamp | |
| 3,747,161 A | 7/1973 | Kalwaites | |
| 3,750,237 A | 8/1973 | Kalwaites | |
| 3,766,922 A | 10/1973 | Krusko | |
| 3,855,046 A | 12/1974 | Hansen et al. | |
| 3,860,003 A | 1/1975 | Buell | |
| 3,917,785 A | 11/1975 | Kalwaites | |
| 4,016,317 A | 4/1977 | Kalwaites | |
| 4,041,951 A | 8/1977 | Sanford | |
| 4,183,995 A | 1/1980 | Marshall | |
| 4,202,868 A | 5/1980 | Hayashi et al. | |
| 4,297,404 A | 10/1981 | Nguyen | |
| 4,333,979 A | 6/1982 | Sciaraffa et al. | |
| 4,555,430 A | 11/1985 | Mays | |
| 4,609,518 A | 9/1986 | Curro et al. | |
| 4,612,226 A | 9/1986 | Kennette et al. | |
| 4,614,679 A | 9/1986 | Farrington et al. | |
| 4,673,402 A | 6/1987 | Weisman et al. | |
| 4,691,417 A | 9/1987 | Vuillaume | |
| 4,693,922 A | 9/1987 | Buyofsky et al. | |
| 4,704,112 A | 11/1987 | Suzuki et al. | |
| 4,718,152 A | 1/1988 | Suzuki et al. | |
| 4,735,842 A | 4/1988 | Buyofsky et al. | |
| 4,741,941 A | 5/1988 | Englebert et al. | |
| 4,780,352 A | 10/1988 | Palumbo | |
| 4,781,710 A | 11/1988 | Megison et al. | |
| 4,805,275 A | 2/1989 | Suzuki et al. | |
| 4,840,829 A | 6/1989 | Suzuki et al. | |
| 4,846,821 A | 7/1989 | Lyons et al. | |
| 4,868,958 A | 9/1989 | Suzuki et al. | |
| 4,879,170 A | 11/1989 | Radwanski et al. | |
| 4,931,355 A | 6/1990 | Radwanski et al. | |
| 4,939,016 A | 7/1990 | Radwanski et al. | |
| 4,950,531 A | 8/1990 | Radwanski et al. | |
| 4,960,630 A * | 10/1990 | Greenway | D04H 18/04 28/104 |
| 4,970,104 A | 11/1990 | Radwanski | |
| 4,988,234 A | 1/1991 | Henkel et al. | |
| 4,988,344 A | 1/1991 | Reising et al. | |
| 4,988,345 A | 1/1991 | Reising | |
| 5,019,062 A | 5/1991 | Ryan et al. | |
| 5,098,764 A | 3/1992 | Bassett et al. | |
| 5,137,600 A | 8/1992 | Barnes et al. | |
| 5,142,752 A | 9/1992 | Greenway et al. | |
| 5,144,729 A | 9/1992 | Austin et al. | |
| 5,180,620 A | 1/1993 | Mende | |
| 5,227,227 A | 7/1993 | Boulanger | |
| 5,242,632 A | 9/1993 | Mende | |
| 5,244,711 A | 9/1993 | Drelich et al. | |
| 5,301,401 A | 4/1994 | Suzuki et al. | |
| 5,369,858 A | 12/1994 | Gilmore et al. | |
| 5,389,202 A | 2/1995 | Everhart et al. | |
| 5,393,599 A | 2/1995 | Quantrille et al. | |
| 5,405,650 A | 4/1995 | Boulanger et al. | |
| 5,407,439 A | 4/1995 | Goulait | |
| 5,415,640 A | 5/1995 | Kirby et al. | |
| 5,437,904 A | 8/1995 | Boulanger et al. | |
| 5,500,270 A | 3/1996 | Langdon et al. | |
| 5,505,720 A | 4/1996 | Walters et al. | |
| 5,514,120 A | 5/1996 | Johnston et al. | |
| 5,527,300 A | 6/1996 | Sauer | |
| 5,562,650 A * | 10/1996 | Everett | A61F 13/4942 604/378 |
| 5,567,376 A | 10/1996 | Turi et al. | |
| 5,575,874 A | 11/1996 | Griesbach et al. | |
| 5,587,225 A | 12/1996 | Griesbach et al. | |
| 5,614,281 A | 3/1997 | Jackson et al. | |
| 5,624,427 A | 4/1997 | Bergman et al. | |

(56) References Cited

U.S. PATENT DOCUMENTS

| | | |
|---|---|---|
| 5,632,072 A | 5/1997 | Simon et al. |
| 5,656,232 A | 8/1997 | Takai et al. |
| 5,670,234 A | 9/1997 | Suehr et al. |
| 5,785,697 A | 7/1998 | Trombetta et al. |
| 5,785,698 A | 7/1998 | Van Iten |
| 5,830,202 A | 11/1998 | Bogdanski et al. |
| 5,858,515 A | 1/1999 | Stokes et al. |
| 5,888,607 A | 3/1999 | Seth et al. |
| 5,906,879 A | 5/1999 | Huntoon et al. |
| 5,928,212 A | 7/1999 | Kline et al. |
| 5,962,112 A | 10/1999 | Haynes et al. |
| 5,990,377 A | 11/1999 | Chen et al. |
| 5,997,981 A | 12/1999 | McCormack et al. |
| 6,022,818 A | 2/2000 | Welchel et al. |
| 6,176,954 B1 | 1/2001 | Tsuji et al. |
| 6,192,556 B1 | 2/2001 | Kikko et al. |
| 6,222,092 B1 | 4/2001 | Hansen et al. |
| 6,228,216 B1 | 5/2001 | Lindsay et al. |
| 6,241,714 B1 | 6/2001 | Raidel et al. |
| 6,242,074 B1 | 6/2001 | Thomas |
| 6,290,685 B1 | 9/2001 | Insley et al. |
| 6,290,979 B1 | 9/2001 | Roe et al. |
| 6,291,050 B1 | 9/2001 | Cree et al. |
| 6,314,627 B1 | 11/2001 | Ngai |
| 6,316,687 B1 | 11/2001 | Davis et al. |
| 6,319,455 B1 | 11/2001 | Kauschke et al. |
| 6,324,738 B1 | 12/2001 | Fleissner |
| 6,331,268 B1 | 12/2001 | Kauschke et al. |
| 6,331,345 B1 | 12/2001 | Kauschke et al. |
| 6,395,957 B1 | 5/2002 | Chen et al. |
| 6,405,416 B1 | 6/2002 | Fleissner |
| 6,413,344 B2 | 7/2002 | Bodaghi |
| 6,417,427 B1 | 7/2002 | Roxendal et al. |
| 6,430,788 B1 | 8/2002 | Putnam et al. |
| 6,436,512 B1 | 8/2002 | Kauschke et al. |
| 6,440,114 B1 | 8/2002 | Bast et al. |
| 6,468,626 B1 | 10/2002 | Takai et al. |
| 6,488,801 B1 | 12/2002 | Bodaghi et al. |
| 6,502,288 B2 | 1/2003 | Black et al. |
| 6,521,555 B1 | 2/2003 | Bodaghi et al. |
| 6,610,173 B1 | 8/2003 | Lindsay et al. |
| 6,610,904 B1 | 8/2003 | Thomas et al. |
| 6,660,362 B1 | 12/2003 | Lindsay et al. |
| 6,671,936 B1 | 1/2004 | Carlson et al. |
| 6,689,242 B2 | 2/2004 | Bodaghi |
| RE38,505 E | 4/2004 | James et al. |
| 6,725,512 B2 | 4/2004 | Carter |
| 6,733,610 B2 | 5/2004 | Mizutani et al. |
| 6,735,832 B1 | 5/2004 | Putnam et al. |
| 6,802,932 B2 | 10/2004 | Kudo et al. |
| 6,822,134 B1 | 11/2004 | Stiehl et al. |
| 6,838,591 B2 | 1/2005 | Waksmundzki et al. |
| 6,888,046 B2 | 5/2005 | Toyoshima et al. |
| 6,911,573 B2 | 6/2005 | Chen et al. |
| 6,911,574 B1 | 6/2005 | Mizutani |
| 6,936,038 B2 | 8/2005 | Tears et al. |
| 6,936,333 B2 | 8/2005 | Shizuno et al. |
| 6,955,847 B1 | 10/2005 | Itou et al. |
| 6,998,017 B2 | 2/2006 | Lindsay et al. |
| 7,102,054 B1 | 9/2006 | Cree et al. |
| 7,105,716 B2 | 9/2006 | Baratian et al. |
| 7,132,585 B2 | 11/2006 | Kudo et al. |
| 7,172,801 B2 | 2/2007 | Hoying et al. |
| 7,175,613 B2 | 2/2007 | Sugiyama et al. |
| 7,194,788 B2 | 3/2007 | Clark et al. |
| 7,267,860 B2 | 9/2007 | Toyoshima et al. |
| 7,294,387 B2 | 11/2007 | Wildeman |
| 7,303,805 B2 | 12/2007 | Seth et al. |
| 7,303,808 B2 | 12/2007 | Taneichi et al. |
| RE40,362 E | 6/2008 | Sternlieb et al. |
| 7,410,683 B2 | 8/2008 | Curro et al. |
| 7,421,766 B2 | 9/2008 | Münstermann |
| 7,455,800 B2 | 11/2008 | Ferencz et al. |
| 7,468,114 B2 | 12/2008 | Sato et al. |
| 7,507,463 B2 | 3/2009 | Noda et al. |
| 7,518,032 B2 | 4/2009 | Seyler |
| 7,534,928 B2 | 5/2009 | Sakamoto et al. |
| 7,547,469 B2 | 6/2009 | Provost et al. |
| 7,553,532 B2 | 6/2009 | Turner et al. |
| 7,553,535 B2 | 6/2009 | Noda et al. |
| 7,569,264 B2 | 8/2009 | Toyoshima et al. |
| 7,589,251 B2 | 9/2009 | Roe |
| 7,632,258 B2 | 12/2009 | Misek et al. |
| 7,648,752 B2 | 1/2010 | Hoying et al. |
| 7,662,462 B2 | 2/2010 | Noda et al. |
| 7,678,442 B2 | 3/2010 | Casey et al. |
| 7,682,686 B2 | 3/2010 | Curro et al. |
| 7,686,921 B2 | 3/2010 | Hamed et al. |
| 7,687,681 B2 | 3/2010 | Di Luccio et al. |
| 7,717,150 B2 | 5/2010 | Manabe et al. |
| 7,718,243 B2 | 5/2010 | Curro et al. |
| 7,718,249 B2 | 5/2010 | Russell et al. |
| 7,815,995 B2 | 10/2010 | Clark et al. |
| 7,829,173 B2 | 11/2010 | Turner et al. |
| 7,838,099 B2 | 11/2010 | Curro et al. |
| 7,851,047 B2 | 12/2010 | Sato et al. |
| 7,855,314 B2 | 12/2010 | Hanao et al. |
| 7,884,259 B2 | 2/2011 | Hanao et al. |
| 7,897,240 B2 | 3/2011 | Noda et al. |
| 7,935,861 B2 | 5/2011 | Suzuki |
| 7,942,992 B2 | 5/2011 | Saka et al. |
| 7,954,213 B2 | 6/2011 | Mizutani et al. |
| 7,955,549 B2 | 6/2011 | Noda et al. |
| 7,972,985 B2 | 7/2011 | Hirose et al. |
| 7,981,822 B2 | 7/2011 | Lester, Jr. et al. |
| 7,993,317 B2 | 8/2011 | Hammons et al. |
| 8,022,267 B2 | 9/2011 | Hellström et al. |
| 8,075,977 B2 | 12/2011 | Curro et al. |
| 8,105,526 B2 | 1/2012 | Stone et al. |
| 8,143,177 B2 | 3/2012 | Noda et al. |
| 8,153,225 B2 | 4/2012 | Turner et al. |
| 8,183,431 B2 | 5/2012 | Noda et al. |
| 8,206,628 B2 | 6/2012 | Stone et al. |
| 8,235,959 B2 | 8/2012 | Ponomarenko et al. |
| 8,273,942 B2 | 9/2012 | Roe |
| 8,304,600 B2 | 11/2012 | Noda et al. |
| 8,393,374 B2 | 3/2013 | Sato et al. |
| 8,450,557 B2 | 5/2013 | Nishitani et al. |
| 8,575,418 B2 | 11/2013 | Gabrielii et al. |
| 8,617,449 B2 | 12/2013 | Baker et al. |
| 8,722,173 B2 | 5/2014 | Oba et al. |
| 8,748,692 B2 | 6/2014 | Suzuki |
| 8,765,250 B2 | 7/2014 | Seyler et al. |
| 8,784,972 B2 | 7/2014 | Sato et al. |
| 8,865,965 B2 | 10/2014 | Sato et al. |
| 9,237,973 B2 | 1/2016 | Abuto et al. |
| 9,327,473 B2 | 5/2016 | Finn et al. |
| 9,445,951 B2 | 9/2016 | Moberg-Alehammar et al. |
| 9,474,660 B2 | 10/2016 | Kirby et al. |
| 9,480,608 B2 | 11/2016 | Kirby et al. |
| 9,480,609 B2 | 11/2016 | Kirby et al. |
| 9,789,009 B2 | 10/2017 | Joseph |
| 9,987,175 B2 | 6/2018 | Butler et al. |
| 10,070,999 B2 | 9/2018 | Faulks et al. |
| 10,285,874 B2 | 5/2019 | Tally et al. |
| 10,470,947 B2 | 11/2019 | Kirby et al. |
| 10,478,354 B2 | 11/2019 | Kirby et al. |
| 11,007,093 B2 | 5/2021 | Beitz et al. |
| 2001/0005926 A1 | 7/2001 | Noelle |
| 2001/0027302 A1 | 10/2001 | Glaug et al. |
| 2002/0002764 A1 | 1/2002 | Putnam et al. |
| 2002/0034914 A1 | 3/2002 | De Leon et al. |
| 2002/0132544 A1 | 9/2002 | Takagaki |
| 2002/0132714 A1 | 9/2002 | Carter et al. |
| 2002/0133132 A1 | 9/2002 | Copat et al. |
| 2002/0143311 A1 | 10/2002 | Brisebois |
| 2003/0003832 A1 | 1/2003 | Childs et al. |
| 2003/0008108 A1 | 1/2003 | Shizuno et al. |
| 2003/0009862 A1 | 1/2003 | Black et al. |
| 2003/0036741 A1 | 2/2003 | Abba et al. |
| 2003/0050615 A1 | 3/2003 | Sakamoto et al. |
| 2003/0119410 A1 | 6/2003 | Bodaghi |
| 2003/0131454 A1 | 7/2003 | Noelle |
| 2003/0135191 A1 | 7/2003 | Price et al. |

(56) References Cited

U.S. PATENT DOCUMENTS

| | | |
|---|---|---|
| 2003/0143376 A1 | 7/2003 | Toyoshima et al. |
| 2003/0162460 A1 | 8/2003 | Saka et al. |
| 2003/0167044 A1 | 9/2003 | Toyoshima et al. |
| 2003/0181882 A1 | 9/2003 | Toyoshima et al. |
| 2003/0203162 A1 | 10/2003 | Fenwick et al. |
| 2003/0211802 A1 | 11/2003 | Keck et al. |
| 2003/0232558 A1 | 12/2003 | Moody et al. |
| 2004/0020579 A1 | 2/2004 | Durrance et al. |
| 2004/0058607 A1 | 3/2004 | Bodaghi |
| 2004/0087924 A1 | 5/2004 | Sroda et al. |
| 2004/0102124 A1 | 5/2004 | Suzuki |
| 2004/0175556 A1 | 9/2004 | Clark et al. |
| 2004/0206442 A1 | 10/2004 | Sommer et al. |
| 2005/0118389 A1 | 6/2005 | Wildeman |
| 2005/0136213 A1 | 6/2005 | Seth et al. |
| 2005/0202744 A1 | 9/2005 | Putnam et al. |
| 2005/0244619 A1 | 11/2005 | Kauschke et al. |
| 2005/0261649 A1 | 11/2005 | Cohen |
| 2005/0261653 A1 | 11/2005 | Digiacomantonio et al. |
| 2005/0281976 A1 | 12/2005 | Curro et al. |
| 2006/0019056 A1 | 1/2006 | Turner et al. |
| 2006/0020251 A1 | 1/2006 | Kelly |
| 2006/0058772 A1 | 3/2006 | Karami |
| 2006/0069380 A1 | 3/2006 | Chen et al. |
| 2006/0122572 A1 | 6/2006 | Suarez |
| 2006/0141217 A1 | 6/2006 | Ellis et al. |
| 2006/0241558 A1 | 10/2006 | Ramshak |
| 2007/0020440 A1 | 1/2007 | Wong et al. |
| 2007/0026753 A1 | 2/2007 | Neely et al. |
| 2007/0036943 A1 | 2/2007 | Hirose et al. |
| 2007/0128411 A1 | 6/2007 | Kawai et al. |
| 2007/0130713 A1 | 6/2007 | Chen et al. |
| 2007/0172628 A1 | 7/2007 | Seth et al. |
| 2007/0203467 A1* | 8/2007 | Koele ................. B32B 5/022 604/361 |
| 2007/0254545 A1 | 11/2007 | Martin |
| 2007/0255247 A1 | 11/2007 | Moberg-Alehammar et al. |
| 2007/0261541 A1 | 11/2007 | Munstermann |
| 2007/0298213 A1 | 12/2007 | Noda et al. |
| 2008/0010795 A1 | 1/2008 | Mizutani et al. |
| 2008/0015531 A1 | 1/2008 | Hird et al. |
| 2008/0044622 A1 | 2/2008 | Noda et al. |
| 2008/0085399 A1 | 4/2008 | Noda et al. |
| 2008/0092350 A1 | 4/2008 | Noelle et al. |
| 2008/0108962 A1 | 5/2008 | Furuta et al. |
| 2008/0132865 A1 | 6/2008 | Li et al. |
| 2008/0172018 A1 | 7/2008 | Chien |
| 2008/0256768 A1 | 10/2008 | Lampila et al. |
| 2008/0261476 A1 | 10/2008 | Strandqvist et al. |
| 2008/0275415 A1 | 11/2008 | Wheeler et al. |
| 2008/0294138 A1 | 11/2008 | Andersson et al. |
| 2008/0300562 A1 | 12/2008 | Ahoniemi et al. |
| 2009/0005752 A1 | 1/2009 | Suzuki et al. |
| 2009/0030391 A1 | 1/2009 | Hammons et al. |
| 2009/0221979 A1 | 9/2009 | Huang et al. |
| 2009/0247977 A1 | 10/2009 | Takeuchi et al. |
| 2009/0259208 A1* | 10/2009 | Hellstrom ............. D04H 1/492 604/383 |
| 2009/0264851 A1 | 10/2009 | Richlen et al. |
| 2010/0108554 A1 | 5/2010 | Melius et al. |
| 2010/0209664 A1 | 8/2010 | Sato et al. |
| 2010/0249740 A1 | 9/2010 | Miyamoto et al. |
| 2010/0274208 A1 | 10/2010 | Gabrielii et al. |
| 2010/0312211 A1 | 12/2010 | Bond et al. |
| 2011/0042011 A1 | 2/2011 | Sato et al. |
| 2011/0151196 A1 | 6/2011 | Schmidt et al. |
| 2011/0250816 A1 | 10/2011 | Fujiwara et al. |
| 2012/0059343 A1 | 3/2012 | Kume et al. |
| 2012/0111483 A1 | 5/2012 | Schneider et al. |
| 2012/0141742 A1 | 6/2012 | Yamaguchi et al. |
| 2012/0171408 A1 | 7/2012 | Turner et al. |
| 2012/0177886 A1 | 7/2012 | Kanya et al. |
| 2012/0179125 A1 | 7/2012 | Kanya et al. |
| 2012/0179126 A1 | 7/2012 | Kanya et al. |
| 2012/0189814 A1 | 7/2012 | Coslett et al. |
| 2012/0226250 A1 | 9/2012 | Sato et al. |
| 2012/0226252 A1 | 9/2012 | Yago et al. |
| 2012/0282436 A1 | 11/2012 | Coe et al. |
| 2012/0310197 A1 | 12/2012 | Thomas |
| 2012/0330260 A1 | 12/2012 | Bishop et al. |
| 2013/0034686 A1 | 2/2013 | Mitsuno |
| 2013/0137328 A1 | 5/2013 | Mitsuno |
| 2013/0158497 A1 | 6/2013 | Yamaguchi et al. |
| 2013/0165883 A1 | 6/2013 | Kimura et al. |
| 2013/0178811 A1 | 7/2013 | Kikuchi et al. |
| 2013/0178815 A1 | 7/2013 | Ohashi et al. |
| 2013/0211358 A1 | 8/2013 | Kikkawa et al. |
| 2013/0304009 A1 | 11/2013 | Wang et al. |
| 2014/0005622 A1 | 1/2014 | Wirtz et al. |
| 2014/0021626 A1 | 1/2014 | Takano et al. |
| 2014/0121623 A1 | 5/2014 | Kirby et al. |
| 2014/0121624 A1* | 5/2014 | Kirby ................. A61F 13/51108 604/383 |
| 2014/0121625 A1 | 5/2014 | Kirby et al. |
| 2014/0154459 A1 | 6/2014 | Krautkramer et al. |
| 2014/0154469 A1* | 6/2014 | Kagawa ............. H01Q 17/002 428/155 |
| 2014/0215780 A1 | 8/2014 | Seils et al. |
| 2014/0234575 A1 | 8/2014 | Mitsuno et al. |
| 2014/0336608 A1 | 11/2014 | Hao et al. |
| 2015/0038933 A1 | 2/2015 | Day et al. |
| 2015/0250660 A1 | 9/2015 | Tally et al. |
| 2015/0282997 A1 | 10/2015 | Arizti et al. |
| 2015/0282998 A1 | 10/2015 | Arizti et al. |
| 2016/0039109 A1 | 2/2016 | Cecchetto et al. |
| 2016/0074244 A1 | 3/2016 | Rosati et al. |
| 2016/0074256 A1 | 3/2016 | Strube et al. |
| 2016/0136011 A1 | 5/2016 | Peri et al. |
| 2016/0167334 A1 | 6/2016 | Arora et al. |
| 2016/0213520 A1 | 7/2016 | Li et al. |
| 2017/0016158 A1 | 1/2017 | Burgess et al. |
| 2017/0065460 A1 | 3/2017 | Rosati et al. |
| 2017/0119596 A1 | 5/2017 | Bewick-Sonntag et al. |
| 2017/0203542 A1 | 7/2017 | Ramaratnam et al. |
| 2017/0226672 A1 | 8/2017 | Kimura et al. |
| 2017/0258645 A1 | 9/2017 | Orr et al. |
| 2017/0258649 A1 | 9/2017 | Rosati et al. |
| 2017/0259524 A1 | 9/2017 | Neton et al. |
| 2017/0312148 A1 | 11/2017 | Dobrosielska-Oura et al. |
| 2017/0319404 A1 | 11/2017 | Bewick-Sonntag et al. |
| 2018/0177643 A1 | 6/2018 | Hao et al. |
| 2018/0200123 A1 | 7/2018 | Xie et al. |
| 2018/0228659 A1 | 8/2018 | Conrad et al. |
| 2018/0228669 A1 | 8/2018 | Schneider et al. |
| 2020/0038261 A1 | 2/2020 | Kirby et al. |
| 2020/0337910 A1 | 10/2020 | Xu et al. |
| 2020/0378044 A1 | 12/2020 | Beitz et al. |
| 2021/0205154 A1 | 7/2021 | Kurihara et al. |
| 2021/0251820 A1 | 8/2021 | Beitz et al. |
| 2021/0388547 A1 | 12/2021 | Oje |
| 2022/0000680 A1 | 1/2022 | Oje |
| 2022/0015960 A1 | 1/2022 | Oje |
| 2022/0015961 A1 | 1/2022 | Oje |
| 2022/0015963 A1 | 1/2022 | Oje |
| 2022/0015964 A1 | 1/2022 | Oje |

FOREIGN PATENT DOCUMENTS

| | | |
|---|---|---|
| CN | 1049388 A | 2/1991 |
| CN | 1134475 A | 10/1996 |
| CN | 1156485 A | 8/1997 |
| CN | 1299258 A | 6/2001 |
| CN | 1348026 A | 5/2002 |
| CN | 2599035 Y | 1/2004 |
| CN | 1672669 A | 9/2005 |
| CN | 1735394 A | 2/2006 |
| CN | 1937983 A | 3/2007 |
| CN | 2923758 Y | 7/2007 |
| CN | 101065528 A | 10/2007 |
| CN | 101370973 A | 2/2009 |
| CN | 101522974 A | 9/2009 |
| CN | 101594989 A | 12/2009 |
| CN | 101959555 A | 1/2011 |
| CN | 102264970 A | 11/2011 |

(56) References Cited

FOREIGN PATENT DOCUMENTS

| | | | |
|---|---|---|---|
| CN | 103352327 A | 10/2013 |
| CN | 104010806 A | 8/2014 |
| CN | 105188630 A | 12/2015 |
| CN | 105208988 A | 12/2015 |
| CN | 204939744 U | 1/2016 |
| CN | 106255485 A | 12/2016 |
| CN | 107072830 A | 8/2017 |
| CN | 107405235 A | 11/2017 |
| CN | 107847355 A | 3/2018 |
| CN | 108103664 A | 6/2018 |
| CN | 108374239 A | 8/2018 |
| DE | 19737219 A1 | 3/1999 |
| DE | 19846857 C1 | 3/2000 |
| DE | 102005036759 A1 | 8/2006 |
| DE | 102006035914 B3 | 1/2008 |
| DE | 102015106490 B3 | 9/2016 |
| EM | 000648472 S | 6/2009 |
| EP | 0341993 A1 | 11/1989 |
| EP | 0418954 A2 | 3/1991 |
| EP | 0432882 A2 | 6/1991 |
| EP | 0556749 A1 | 8/1993 |
| EP | 0446432 B1 | 8/1996 |
| EP | 0687169 B1 | 11/1999 |
| EP | 1036871 A1 | 9/2000 |
| EP | 1190690 A2 | 3/2002 |
| EP | 1209271 A1 | 5/2002 |
| EP | 0863734 B1 | 6/2002 |
| EP | 1059908 B1 | 10/2004 |
| EP | 1207829 B1 | 8/2006 |
| EP | 2157223 A1 | 2/2010 |
| EP | 1902168 B1 | 7/2010 |
| EP | 1803429 B1 | 12/2011 |
| EP | 2159043 B1 | 6/2012 |
| EP | 2505173 A1 | 10/2012 |
| GB | 1088376 A | 10/1967 |
| GB | 1395402 A | 5/1975 |
| JP | 1977066772 A | 6/1977 |
| JP | H0424261 A | 1/1992 |
| JP | 1992061857 A | 2/1992 |
| JP | 08109564 A | 4/1996 |
| JP | 2000023715 A | 1/2000 |
| JP | 2001123366 A | 5/2001 |
| JP | 3181195 B2 | 7/2001 |
| JP | 2002173863 A | 6/2002 |
| JP | 2002287228 A2 | 10/2002 |
| JP | 1172567 S | 5/2003 |
| JP | 3408078 B2 | 5/2003 |
| JP | 3453031 B2 | 10/2003 |
| JP | 2004113489 A | 4/2004 |
| JP | 2004121701 A | 4/2004 |
| JP | 1220443 S | 10/2004 |
| JP | 2005312547 A | 11/2005 |
| JP | 2005334374 A | 12/2005 |
| JP | 2006175688 A | 7/2006 |
| JP | 2007190315 A | 8/2007 |
| JP | 2007195958 A | 8/2007 |
| JP | 3989476 B2 | 10/2007 |
| JP | 3989477 B2 | 10/2007 |
| JP | 2008148807 A | 7/2008 |
| JP | 2008161302 A | 7/2008 |
| JP | 2008161319 A | 7/2008 |
| JP | 2009050621 A | 3/2009 |
| JP | 4301999 B2 | 7/2009 |
| JP | 2009153556 A | 7/2009 |
| JP | 2009279097 A | 12/2009 |
| JP | 2009279098 A | 12/2009 |
| JP | 2009299227 A | 12/2009 |
| JP | 2010024573 A | 2/2010 |
| JP | 2010115352 A | 5/2010 |
| JP | 2010133071 A | 6/2010 |
| JP | 4566109 B2 | 10/2010 |
| JP | 4627014 B2 | 2/2011 |
| JP | 2011110317 A | 6/2011 |
| JP | 4889273 B2 | 3/2012 |
| JP | 5074301 B2 | 11/2012 |
| JP | 5086035 B2 | 11/2012 |
| JP | 5087419 B2 | 12/2012 |
| JP | 1479504 S | 9/2013 |
| JP | 2017075431 A | 4/2017 |
| KR | 20100040729 A | 4/2010 |
| KR | 20180060050 A | 6/2018 |
| RU | 2415659 C1 | 4/2011 |
| WO | 1990004066 A2 | 4/1990 |
| WO | 1991011161 A1 | 8/1991 |
| WO | 1998052458 A1 | 11/1998 |
| WO | 1999055532 A1 | 11/1999 |
| WO | 2001072251 A1 | 10/2001 |
| WO | 04062528 A2 | 7/2004 |
| WO | 2004059061 A1 | 7/2004 |
| WO | 2005007952 A2 | 1/2005 |
| WO | 2005007962 A1 | 1/2005 |
| WO | 2005065606 A1 | 7/2005 |
| WO | 2006007307 A1 | 1/2006 |
| WO | 2006007340 A1 | 1/2006 |
| WO | 2006011724 A1 | 2/2006 |
| WO | 09101591 A1 | 8/2009 |
| WO | 2009152791 A1 | 12/2009 |
| WO | 2010074205 A1 | 7/2010 |
| WO | 2011142272 A1 | 11/2011 |
| WO | 2012024576 A1 | 2/2012 |
| WO | 2012029391 A1 | 3/2012 |
| WO | 2012086766 A1 | 6/2012 |
| WO | 2013005782 A1 | 1/2013 |
| WO | 2013047890 A1 | 4/2013 |
| WO | 2013099624 A1 | 7/2013 |
| WO | 2014204016 A1 | 12/2014 |
| WO | 2016040112 A1 | 3/2016 |
| WO | 2016040120 A1 | 3/2016 |
| WO | 2016073713 A1 | 5/2016 |
| WO | 2016096529 A1 | 6/2016 |
| WO | 2018193775 A1 | 10/2018 |
| WO | 2020035257 A1 | 2/2020 |

OTHER PUBLICATIONS

Lemere, Mark, "Nonwoven Bonding Technologies", p. 7, Image, Inda.org, http://www.inda.org/BIO/cab2012_444_PPT.pdf.

Newbusi, "Application of non-woven fabrics on diapers and their technical development trends", Industry News, Apr. 18, 2019.

Huddersfield Textiles, "Nonwoven Manufacturing", www.tikp.co.uk/knowledge/technology/nonwovens/under-construction/?print=true, Jul. 10, 2019.

Co-pending U.S. Appl. No. 17/239,775, filed Apr. 26, 2021, by Beitz et al. for "Incorporation of Apertured Area Into An Absorbent Article".

Co-pending U.S. Appl. No. 17/295,505, filed May 20, 2021, by Carrillo Ojeda et al. for "Three-Dimensional Nonwoven Materials and Methods of Manufacturing Thereof".

Co-pending U.S. Appl. No. 17/295,565, filed May 20, 2021, by Carrillo Ojeda et al. for "Three- Dimensional Nonwoven Materials and Methods of Manufacturing Thereof".

Co-pending U.S. Appl. No. 17/295,585, filed May 20, 2021, by Carrillo Ojeda et al. for "Three-Dimensional Nonwoven Materials and Methods of Manufacturing Thereof".

Co-pending U.S. Appl. No. 17/295,607, filed May 20, 2021, by Carrillo Ojeda et al. for "Three-Dimensional Nonwoven Materials and Methods of Manufacturing Thereof".

Co-pending U.S. Appl. No. 17/295,637, filed May 20, 2021, by Carrillo Ojeda et al. for "Three-Dimensional Nonwoven Materials and Methods of Manufacturing Thereof".

Co-pending U.S. Appl. No. 17/295,703, filed May 20, 2021, by Carrillo Ojeda et al. for "Three-Dimensional Nonwoven Materials and Methods of Manufacturing Thereof".

\* cited by examiner

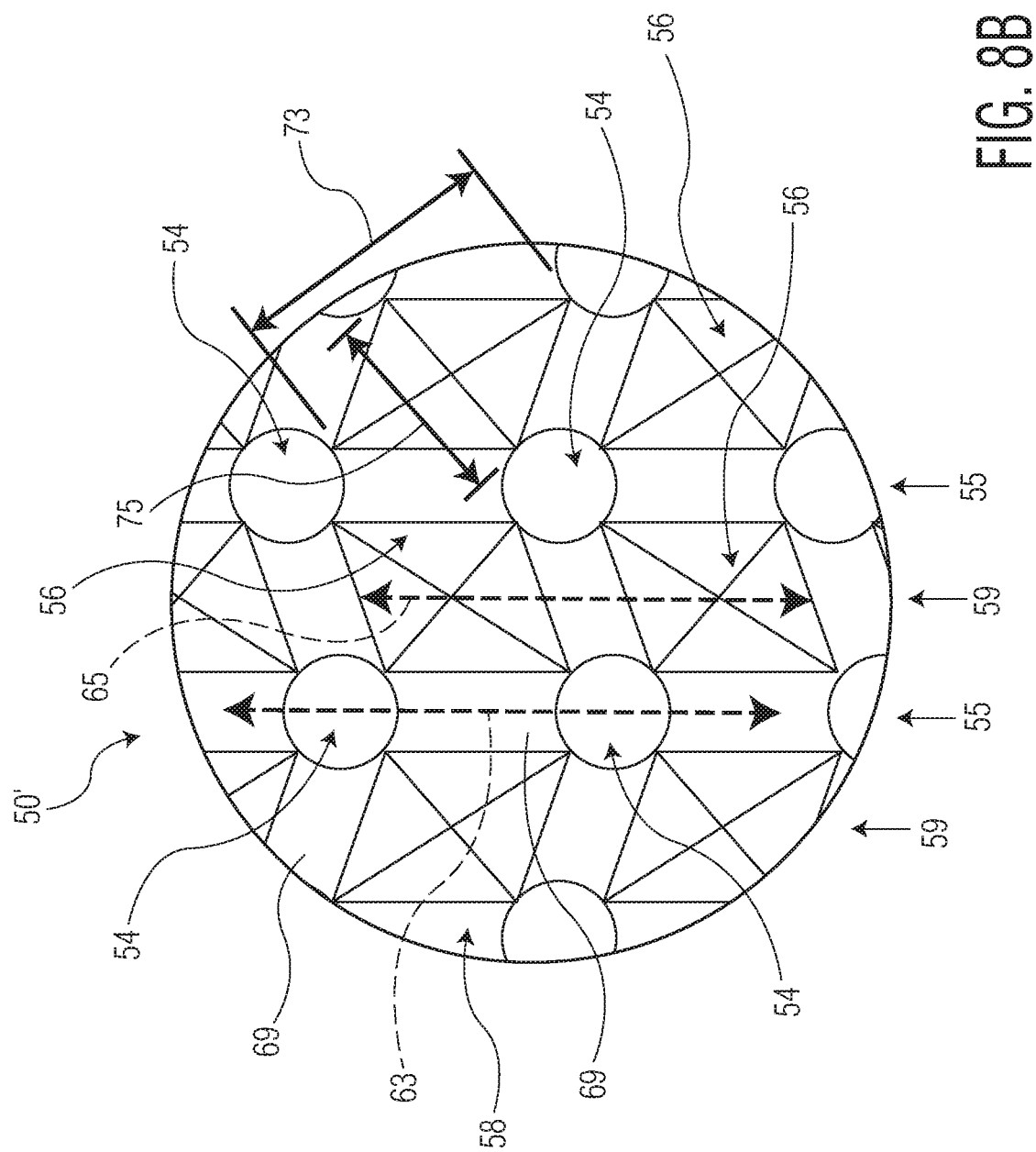

THREE-DIMENSIONAL NONWOVEN MATERIALS AND METHODS OF MANUFACTURING THEREOF

TECHNICAL FIELD

The present disclosure relates to nonwoven materials. More specifically, the present disclosure relates to three dimensional nonwoven materials.

BACKGROUND OF THE DISCLOSURE

Fibrous nonwoven web materials are in wide use in a number of applications including but not limited to absorbent structures and wiping products, many of which are disposable. In particular, such materials are commonly used in personal care absorbent articles such as diapers, diaper pants, training pants, feminine hygiene products, adult incontinence products, bandages, and wiping products such as baby and adult wet wipes. They are also commonly used in cleaning products such as wet and dry disposable wipes which may be treated with cleaning and other compounds which are designed to be used by hand or in conjunction with cleaning devices such as mops. Yet a further application is with beauty aids such as cleansing and make-up removal pads and wipes.

In many of these applications, three-dimensionality and increased surface area are desirable attributes. This is particularly true with materials for the aforementioned personal care absorbent articles and cleaning products. For example, one of the main functions of personal care absorbent articles is to absorb and retain body exudates such as blood, menses, urine, and bowel movements. Some body exudates, such as solid and semi-solid fecal material and menses, have difficulty penetrating such components of the absorbent article as easily as low viscosity exudates, such as urine, and tend to spread across the surface of such materials. The spread of body exudates across a nonwoven material can result in leakage of the body exudates from the absorbent article in which the material is used. Semi-solid fecal material, such as low viscosity fecal material which can be prevalent with younger children, and menses can be especially difficult to contain in an absorbent article. These exudates can move around on a body facing material of an absorbent article under the influence of gravity, motion, and pressure by the wearer of the absorbent article. The migration of the exudates is often towards the perimeter of the absorbent article, increasing the likelihood of leakage and smears against the skin of the wearer which can make clean-up of the skin difficult and can lead to an increased potential for skin irritation of a wearer of the absorbent article.

While attempts have been made in the past to provide nonwoven materials that seek to reduce spreading of body exudates through the creation of three-dimensional topography, opportunities for improvement still exist. For example, various types of embossing have been utilized to create three-dimensionality. However, this approach requires high basis weight materials to create a structure with significant topography and the process can reduce the thickness of the material due to the inherent nature of the crushing and bonding process of embossing. The densified sections from embossing can also create weld points that are impervious to the passage of body exudates and can cause the material to stiffen and become harsh to the touch.

Other approaches to provide three-dimensionality to nonwoven materials can include fiber forming on a three-dimensional forming surface and aperturing fibrous webs. Current technologies involving fiber forming can result in nonwoven materials having low resilience at lower basis weights (assuming soft fibers with desirable aesthetic attributes are used) and the topography is significantly degraded when wound on a roll and put through subsequent converting processes. Aperturing can seek to generate three-dimensionality by displacing the fiber out of the plane of the original two-dimensional web. Typically, the extent of the three-dimensionality is limited and, under sufficient load, the displaced fiber may be pushed back toward its original position resulting in at least partial closure of the aperture. Aperturing processes that attempt to "set" the displaced fiber outside the plane of the original web are also prone to degrading the softness of the starting web.

As a result, there is a still a need for both a material and a process and apparatus which provide three-dimensional characteristics that meet the aforementioned needs. There remains a need for a nonwoven material that can adequately reduce the spreading of body exudates in the absorbent article to help reduce the likelihood of leakage of exudates from the absorbent article. There remains a need for a nonwoven material that can minimize the amount of body exudates in contact with the wearer's skin. There remains a need for an absorbent article that can provide physical and emotional comfort to the wearer of the absorbent article.

SUMMARY OF THE DISCLOSURE

In one embodiment, an absorbent article may have a front waist region with a front waist edge, a rear waist region with a rear waist edge, and a crotch region disposed between the front waist region and the rear waist region, and the article may comprise an outer cover, a bodyside liner, an absorbent body disposed between the outer cover and the body side liner, and a nonwoven material coupled to the bodyside liner having a front edge, a rear edge, and a material length. The nonwoven material may comprise an apertured zone comprising a plurality of openings formed between nodes and connecting ligaments of the nonwoven material and providing a percent open area for the apertured zone of the nonwoven material that is greater than about 15%, as determined by the Material Sample Analysis Test Method. The nonwoven material may be coupled to bodyside liner by a primary front waist bond extending throughout a primary front waist bonding region and a primary rear waist bond extending throughout a primary rear waist bonding region, the primary front waist bonding region extending through the apertured zone and the primary rear waist bonding region being spaced from the primary front waist bonding region, and the primary rear waist bonding region may have a length that is between about 2% and about 10% of the material length and the primary front waist bonding region may have a length that is between about 20% and about 50% of the material length.

In another embodiment, an absorbent article may have a front waist region with a front waist edge, a rear waist region with a rear waist edge, and a crotch region disposed between the front waist region and the rear waist region, the article may further comprise an outer cover, a bodyside liner, an absorbent body disposed between the outer cover and the body side liner, and a nonwoven material having a front edge, a rear edge, and a material length coupled to the bodyside liner. The nonwoven material may further comprise an apertured zone comprising a plurality of openings formed between nodes and connecting ligaments of the nonwoven material and providing a percent open area for the apertured zone of the nonwoven material that is greater than about 15%, as determined by the Material Sample Analysis Test Method, wherein the nonwoven material is coupled to the bodyside liner by a rear waist mechanical bond extending through the apertured zone and covering a primary rear waist bonding region, a rear waist adhesive bond extending through the apertured zone and covering a secondary rear waist bonding region which at least partially overlaps the primary rear waist bonding region, and a front waist bond extending through the apertured zone and covering a front waist bonding region that is spaced from the primary rear waist bonding region and the secondary rear waist bonding region. The front waist bonding region may further have a length that is between about 20% and about 50% of the material length, the primary rear waist bonding region may further have a length that is between about 2% and about 10% of the material length, and the secondary rear waist bonding region may further have a length that is between about 2% and about 10% of the material length.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 8B is a detailed top view of a portion of an alternative forming surface that can be utilized in the processes of FIGS. 7A-7C.

Figure 1:
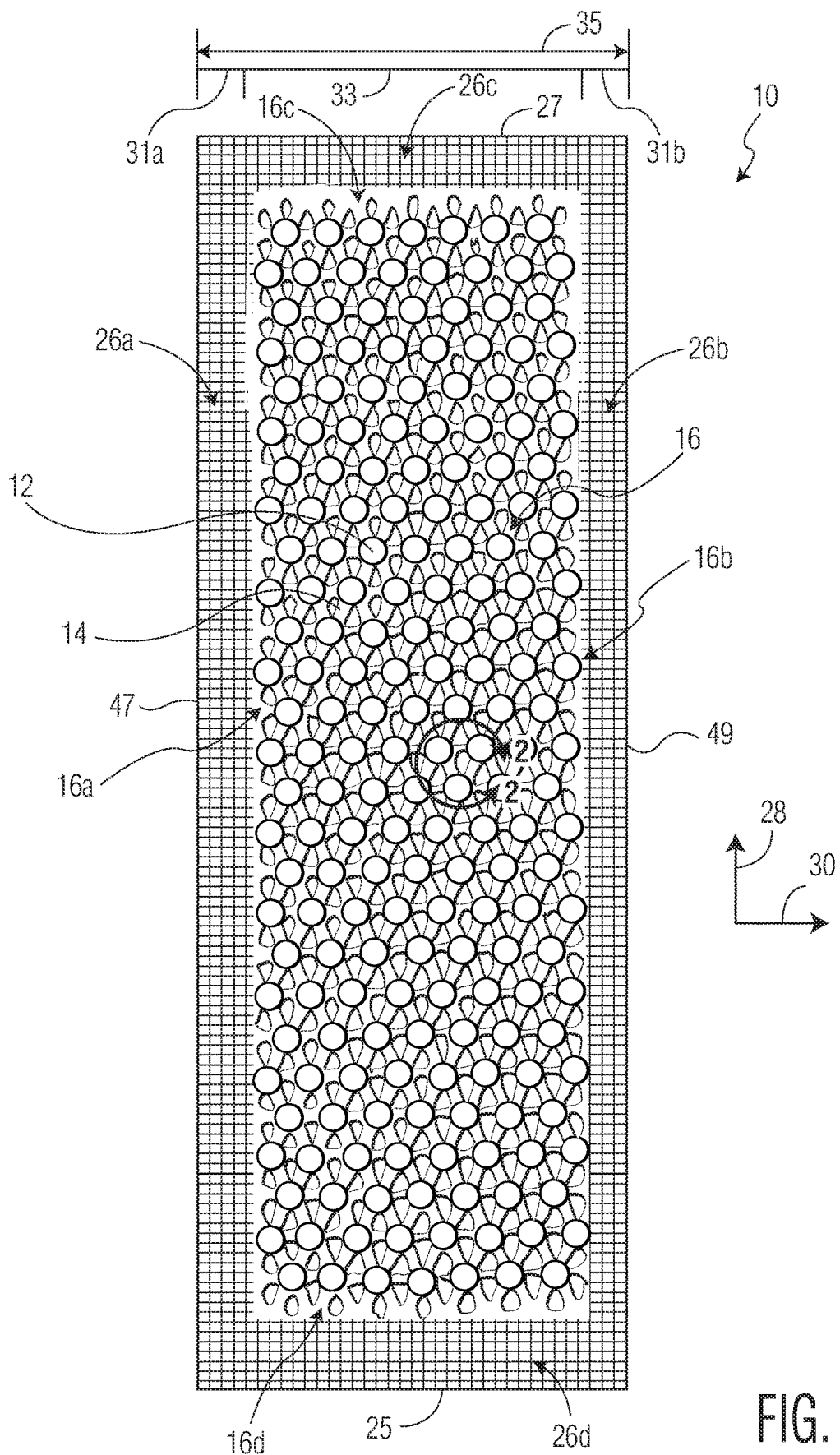
FIG. 1 is a top view of an exemplary embodiment of a three-dimensional nonwoven material according to the present invention.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards a nonwoven material 10, 110, 210, 310, methods 100', 100", 100'" of manufacturing the same, and absorbent articles 410, 510, 610, 710 including such exemplary nonwoven materials. Each example is provided by way of explanation and is not meant as a limitation. For example, features illustrated or described as part of one embodiment or figure can be used on another embodiment or figure to yield yet another embodiment. It is intended that the present disclosure include such modifications and variations. Any of the discussion below referencing a specific exemplary nonwoven material 10, 110, 210, 310 is intended to apply to any of the other embodiments of nonwoven material 10, 110, 210, 310 described herein unless otherwise stated. Additionally, any discussion below referencing a specific method 100', 100", 100'" of manufacturing a nonwoven material is intended to apply to any of the other embodiments of methods 100', 100", 100'" of manufacturing a nonwoven material described herein unless otherwise stated. Further, any discussion below referencing a specific absorbent article 410, 510, 610, 710 is intended to apply to any of the other embodiments of the absorbent articles 410, 510, 610, 710 described herein unless otherwise stated.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid-entangled" generally refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) is then directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, their fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 2:
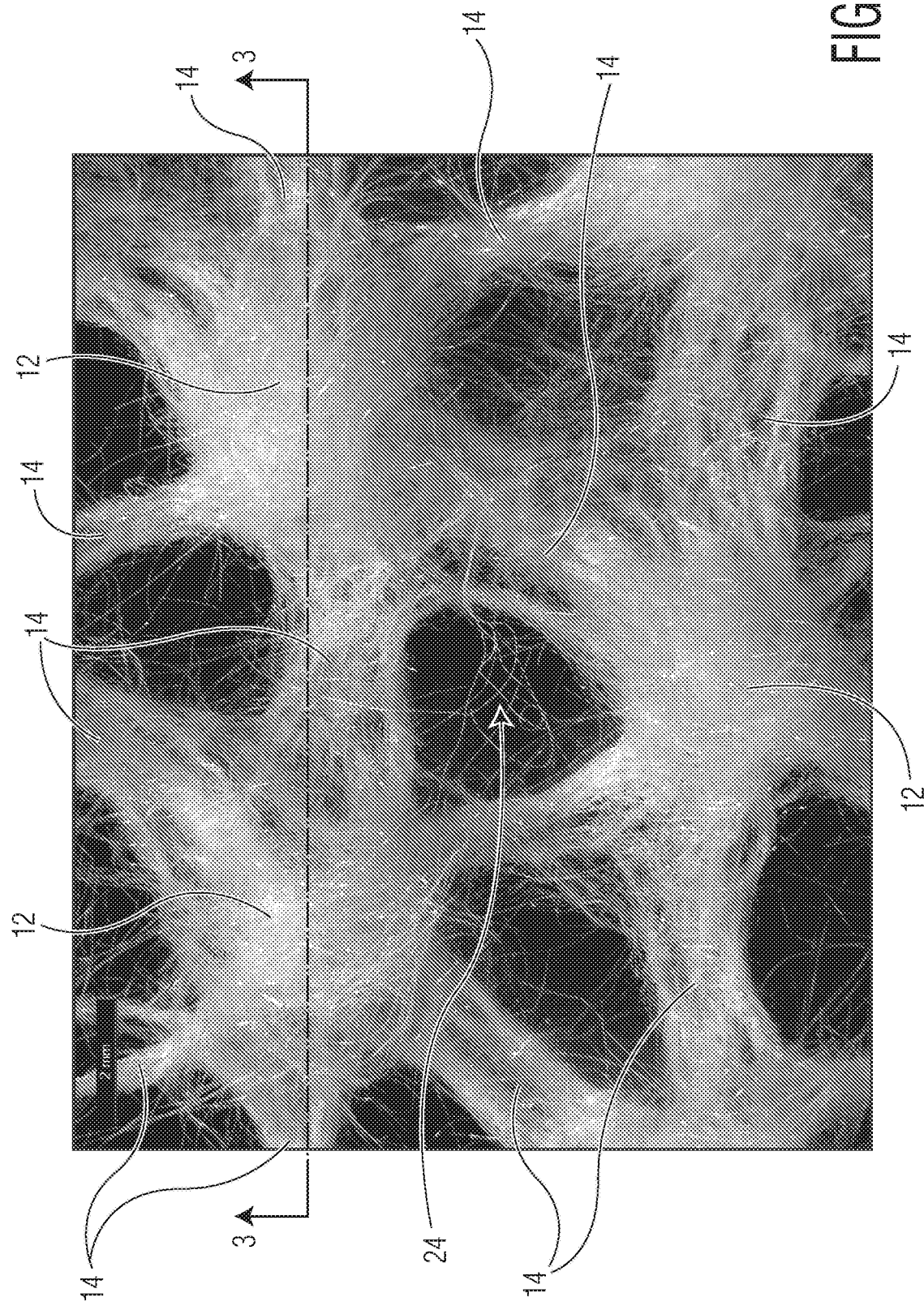
FIG. 2 is a Scanning Electron Microscope (SEM) image providing a detailed view taken from the embodiment of FIG. 1.
Figure 3:
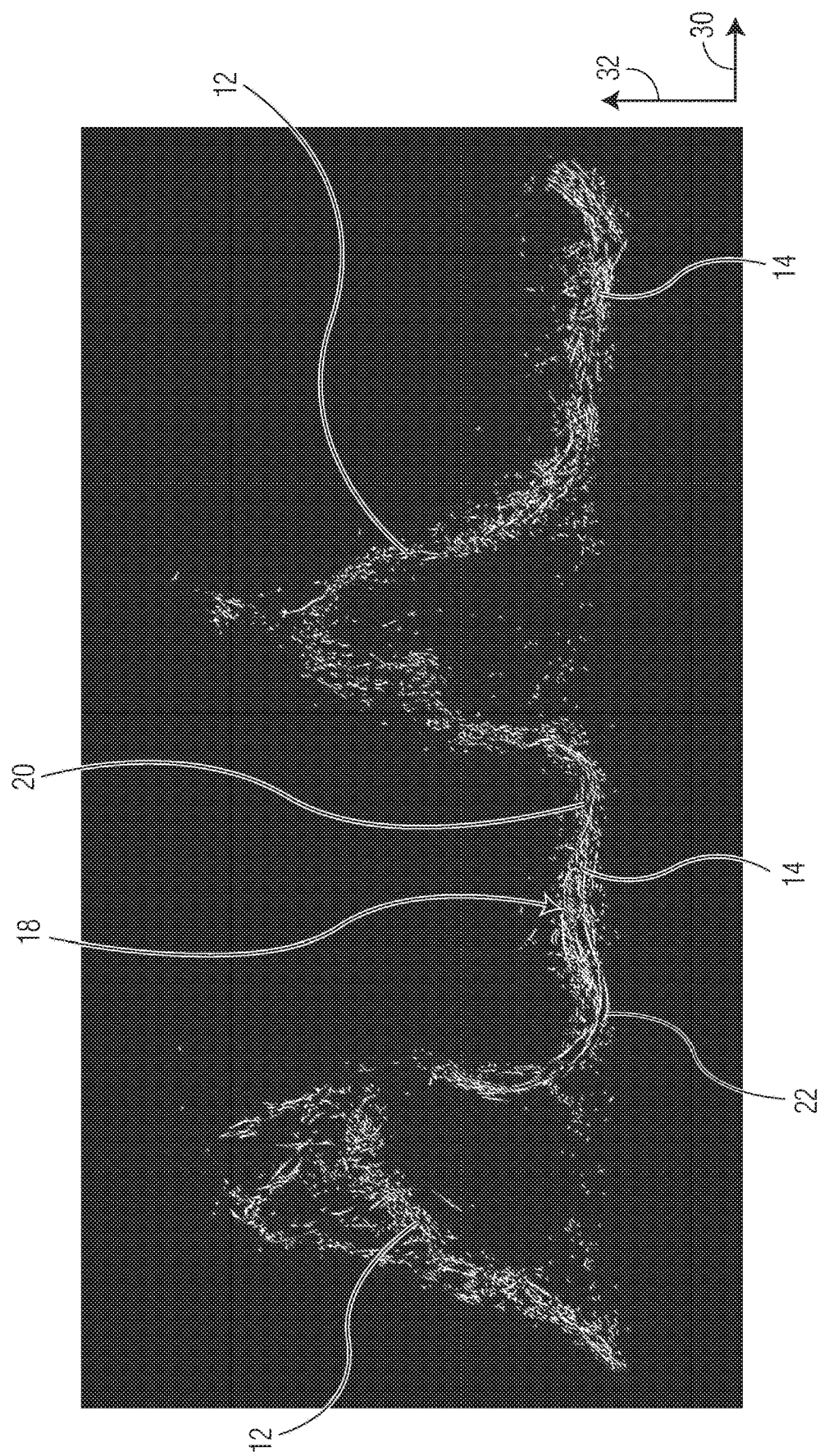
FIG. 3 is an SEM image providing a cross-section view taken from the embodiment of FIG. 1 along line 3-3.

Three-dimensional Web with Nodes, Ligaments, and Openings:

As depicted in FIGS. 1-3, a three-dimensional nonwoven material 10 can include a plurality of nodes 12 and a plurality of connecting ligaments 14 (only one of the nodes 12 and one of the connecting ligaments 14 being labeled in FIG. 1 for clarity purposes). The nodes 12 and connecting ligaments 14 can be disposed within an apertured zone 16 of the material 10. As best illustrated in the cross-sectional view of FIG. 3, the nodes 12 can extend away from a base plane 18 on a first surface 20 of the nonwoven material 10. The base plane 18 can be defined as the generally planar region of the first surface 20 of the nonwoven material 10 other than the portion of the nonwoven material 10 forming the nodes 12. In other words, for the embodiment depicted in FIGS. 1-3, the base plane 18 can be formed by the first surface 20 of the nonwoven material 10 that provides the connecting ligaments 14. The nonwoven material 10 can also include a second surface 22. The first surface 20 can be opposite from the second surface 22, as depicted in FIG. 3.

The nodes 12 can be configured in a variety of shapes and sizes as will be discussed in further detail below in the discussion of the manufacturing of the nonwoven material 10. In some embodiments, the nodes 12 can be generally cylindrical in shape. In preferred embodiments, the nodes 12 are configured to not include any openings or apertures. In some embodiments, the nodes 12 can have a height 15 (as measured in a direction perpendicular to the base plane 18) of between about 1 mm to about 10 mm, and more preferably, from about 3 mm to about 6 mm. The height 15 of the nodes 12 is measured using the analysis techniques described in the Node Analysis Test Method described in the Test Methods section herein. In some embodiments, a majority of the nodes 12 can each have an area (as measured by the area of the node 12 within the base plane 18) of about 5 mm$^2$ to about 35 mm$^2$, and more preferably, from about 10 mm$^2$ to about 20 mm$^2$. The plurality of nodes 12 can be configured in the apertured zone 16 such that the nodes 12 provide a node density of about 1.0 nodes/cm$^2$ to about 3.0 nodes/cm$^2$. The node area and node density within the apertured zone 16 can be measured using the analysis techniques described in the Material Sample Analysis Test Method described in the Test Methods section herein.

As depicted in FIG. 1 and in more detail in FIG. 2, the connecting ligaments 14 can interconnect the plurality of nodes 12. An individual connecting ligament 14 can be referred to as extending between only two adjacent nodes 12. In other words, an individual connecting ligament 14 does not interconnect three or more nodes 12. In preferred embodiments, a majority of the plurality of nodes 12 can include at least three connecting ligaments 14 connecting to adjacent nodes 12. In preferred embodiments, a majority of the plurality of nodes 12 can include ten or less connecting ligaments 14 connecting to adjacent nodes 12. In some embodiments, the nonwoven material 10 can be configured such that a majority of the plurality of nodes 12 can include three to eight connecting ligaments 14 connecting to adjacent nodes 12. For example, in the embodiment depicted in FIGS. 1 and 2, a majority of the plurality of nodes 12 include six connecting ligaments 14 that connect to adjacent nodes 12. In other embodiments, it can be preferable to have a majority of the plurality of nodes 12 include three to six connecting ligaments 14 connecting to adjacent nodes 12, and in some embodiments, preferably include three to four connecting ligaments 14 connecting to adjacent nodes 12.

The nonwoven material 10 can also include a plurality of openings 24 in the apertured zone 16. The openings 24 can also be referred to herein as "apertures". The openings 24 as described herein are areas of the nonwoven material 10 that have a lower density of fibers of the nonwoven material 10 in comparison to nodes 12 and connecting ligaments 14. In some embodiments, the openings 24 can be substantially devoid of fibers. As used herein, the openings 24 are to be distinguished from the normal interstitial fiber-to-fiber spacing commonly found in fibrous nonwoven materials. For example, FIG. 2 provides an SEM image of an exemplary nonwoven material 10 labels one opening 24 which includes a lower density of fibers than adjacent nodes 12 and connecting ligaments 14. The openings 24 can be formed between the plurality of connecting ligaments 14 and the plurality of nodes 12. Individual openings 24 can be disposed between adjacent nodes 12. Individual openings 24 can be defined between at least three connecting ligaments 14 and at least three nodes 12. In some embodiments, individual openings 24 can be defined between at least four connecting ligaments 14 and at least four nodes 12. In some embodiments, a majority of the plurality of openings 24 can be configured such that each has an area (as measured by the area of the opening 24 within the base plane 18) that ranges from about 5 mm² to about 25 mm², more preferably from about 7 mm² to about 20 mm², and even more preferably, from about 7 mm² to about 17 mm². The area of the openings 24 within the apertured zone 16 can be measured using the analysis techniques in the Material Sample Analysis Test Method as described in the Test Methods section herein.

Figure 4:
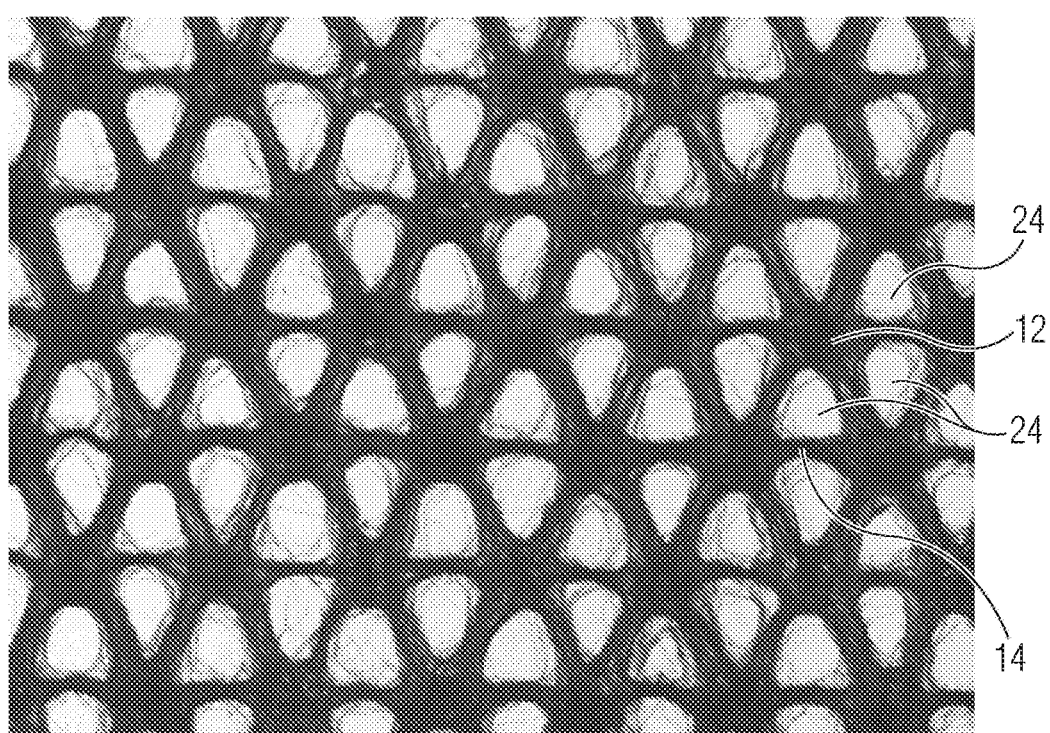
FIG. 4 is a detailed view taken from FIG. 1 illustrating the transmitted light utilized to calculate the percent open area of the apertured zone of the nonwoven material of FIG. 1.

In some embodiments, the plurality of openings 24 for the nonwoven material 10 can provide a percent open area for the apertured zone 16 from about 10% to about 60%. In some preferred embodiments, the plurality of openings 24 for the nonwoven material 10 can provide a percent open area for the apertured zone 16 from about 15% to about 45%. In some preferred embodiments, the nonwoven material 10 can provide a percent open area for the apertured zone 16 from about 20% to about 40%, or even more preferably from about 20% to about 30%. As used herein, the percent open area is determined using the Material Sample Analysis Test Method as described in the Test Methods section herein. Although it is described in detail in the Test Methods section, the Material Sample Analysis Test Method involves projecting a light source on the nonwoven material 10 such that the openings 24 can be identified by the property that the openings 24 allow a greater percentage of light to pass through the nonwoven material 10, which is illustrated in FIG. 4 (with only three openings 24 being labeled for purposes of clarity), as compared to nodes 12 and ligaments 14.

The plurality of openings 24 can provide a variety of beneficial properties to the nonwoven material 10. For example, the openings 24 can provide enhanced fluid transfer for the nonwoven material 10 and/or increased permeability. As an example, if the nonwoven material 10 is utilized in an article that intakes and distributes fluid, the openings 24 can help provide increased intake and distribution of fluids through and/or across the nonwoven material 10.

In particular, the plurality of openings 24 can enhance the ability of a material like the nonwoven material 10 to intake and distribute BM material (also referred to herein as feces or fecal matter), resulting in less pooling of the BM on the material 10 and therefore less BM disposed against a skin of a wearer of an absorbent article comprising such nonwoven material 10. In order to determine the ability of different nonwoven materials to effectively handle simulated BM, a number of different nonwoven materials 10 (Materials A-F), according to aspects of the present disclosure, were tested utilizing a test method which determined a BM pooled percent value. Such a test method is described as a "Determination of Residual Fecal Material Simulant" test method in U.S. Pat. No. 9,480,609, titled "Absorbent Article", the entirety of which is hereby incorporated by reference to the extent not contradictory herewith. The different nonwoven materials tested were all formed in a similar manner but with different forming surfaces resulting in different patterns of nodes 12, ligaments 14, and openings 24. These different patterns produced differences in percent open area values within the apertured zone 16, average opening areas, and material bulk properties of the formed nonwoven materials. The different nonwoven materials, and their properties and performance results, are shown below in Table 1.

TABLE 1

| Material Code | BM Pooled (%) | Open Area (%) | Bulk (mm) | Average Opening Area (mm²) |
|---|---|---|---|---|
| A | 35.87 | 21.91 | 2.301 | 10.52 |
| B | 26.60 | 27.31 | 2.876 | 11.81 |
| C | 21.35 | 28.32 | 2.935 | 15.74 |
| D | 23.31 | 30.75 | 3.746 | 20.13 |
| E | 24.58 | 22.32 | 3.961 | 13.79 |
| F | 23.62 | 28.94 | 4.02 | 19.73 |
| GentleAbsorb ® | 42.57 | 0 | 1.5 | 0 |

Primarily, it can be seen how effective materials which have openings 24, providing such materials with percent open area values in the aperture zone 16, are in terms of reducing the amount of pooled BM on such materials. For example, as shown in Table 1, Material A, having the lowest percent open area value, still performed significantly better than the GentleAbsorb® material in terms of an amount of BM left pooled. In fact, all of the tested Materials A-F performed well in comparison to the performance of the GentleAbsorb® material, generally supporting a preferred percent open area range of at least about 20%, or at least about 25%, or at least about 30%, or between about 20% and about 30%.

It can also be seen that it may be preferred, along with such nonwoven materials 10 having the minimum percent open area values of the apertured zone 16 described herein, or percent open area value ranges described herein, it may be preferred for the nonwoven materials 10 to have openings 24 which have relatively larger average area. For example, it can be seen from Table 1 that Materials A and E have similar percent open area values. However, Material E performed significantly better than Material A with respect to the BM left pooled. As seen in Table 1, Material E has an average opening area of 13.79 mm² while the Material A only has an average opening area of 10.52 mm². Accordingly, it may be preferred to the nonwoven materials 10 of the present disclosure to have average open areas of at least 10.52 mm², or at least about 11 mm², or at least about 12 mm², or at least about 13 mm², or at least 13.79 mm². It may be beneficial for the nonwoven materials of the present disclosure to have such average areas of the openings 24 while having a percent open area value of the nonwoven material in the apertured zone 16 of at least 21.91%, or at least about 22%, or at least about 23%, or between about 20% and about 30%.

In some particularly preferred embodiments of the nonwoven materials of the present disclosure, it may be preferable for such materials to have a percent open area value of greater than about 27%, or greater than about 27.31% and less than about 31%, or less than about 30.75%. For example, Materials B, C, and D show Material C performing the better than both Materials B and C, with Materials B and D having percent open area values less than and greater than Material C, respectively. Alternatively, it may be preferable for embodiments of the nonwoven materials of the present disclosure to have average areas of openings 24 that are greater than about 11.81 mm$^2$, or greater than about 12 mm$^2$ and less than about 20.13 mm$^2$, or less than about 21 mm$^2$. For instance, Materials B, C, and D show Material C performing better than both Materials B and D, with Materials B and D having average area values of the openings 24 less than and greater than Material C, respectively. In still further embodiments, it may be preferred for the nonwoven materials of the present disclosure to have a percent open area value of greater than about 27%, or greater than about 27.31% and less than about 31%, or less than about 30.75% and also have average opening areas of greater than about 11.81 mm$^2$, or greater than about 12 mm$^2$ and less than about 20.13 mm$^2$, or less than about 21 mm$^2$.

Figure 5A:
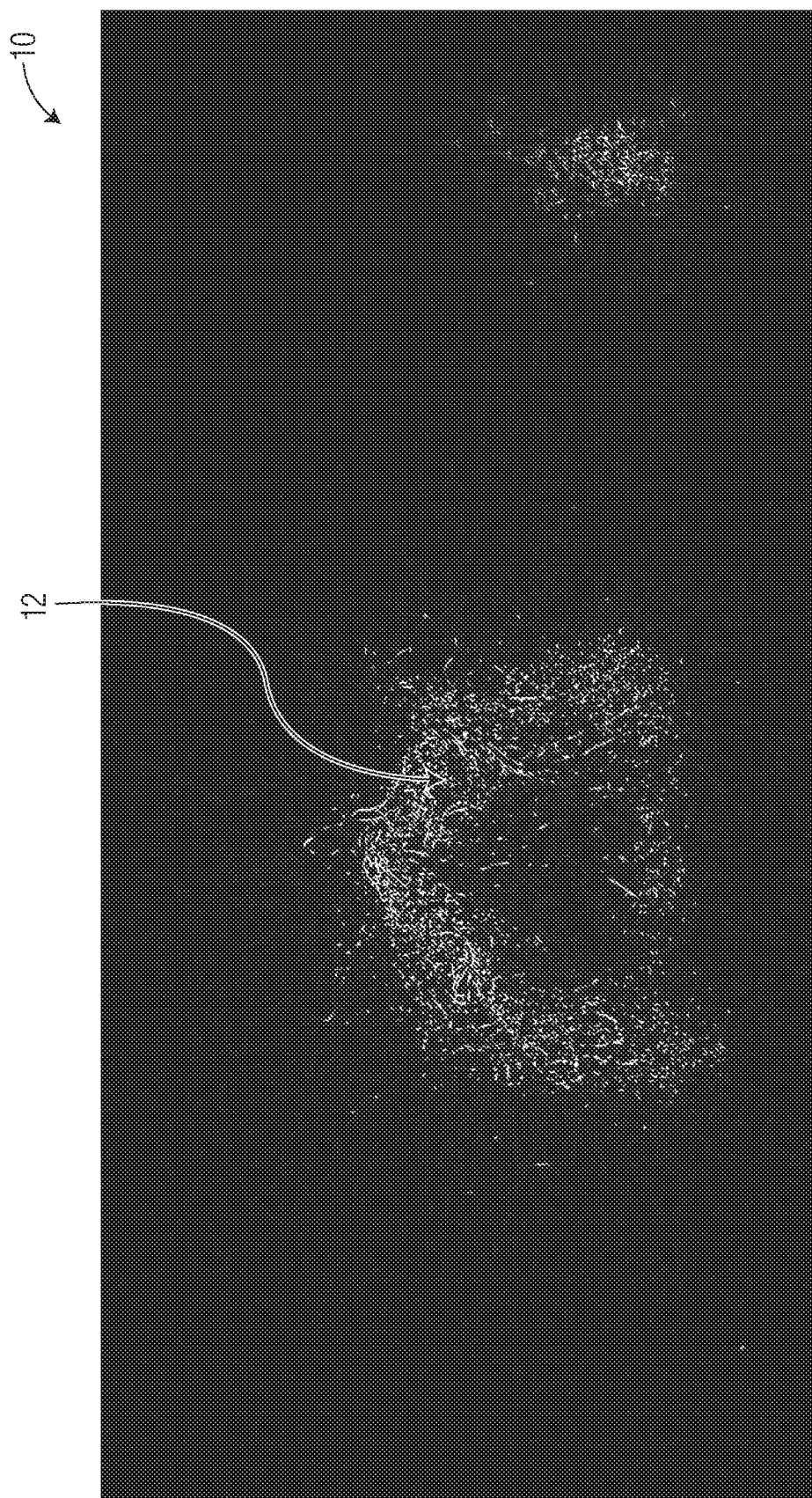
FIGS. 5A and 5B are Micro-CT images of cross-sections of two exemplary embodiments of a nonwoven, taken through a node.
Figure 5B:
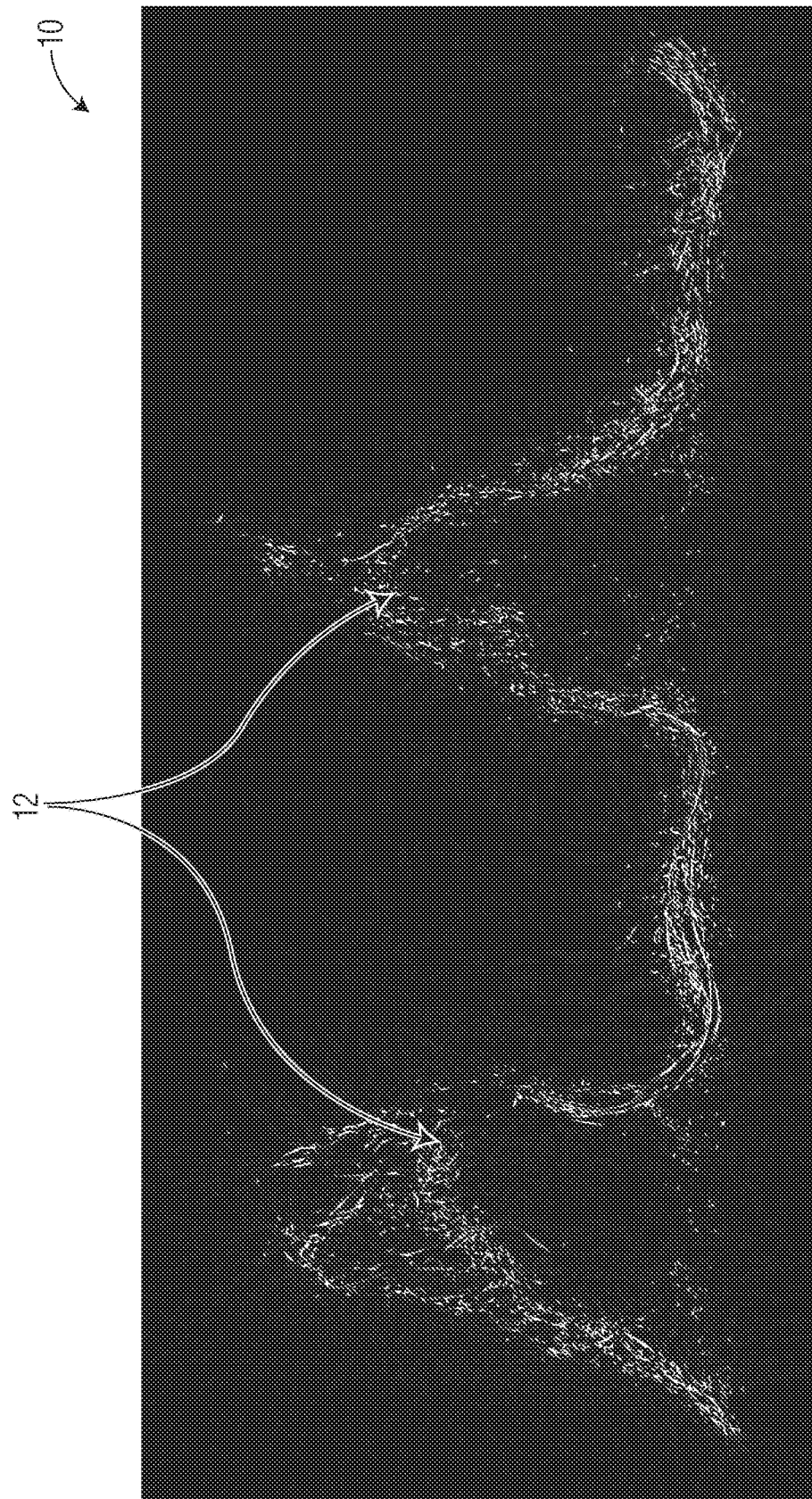
Figure 5C:
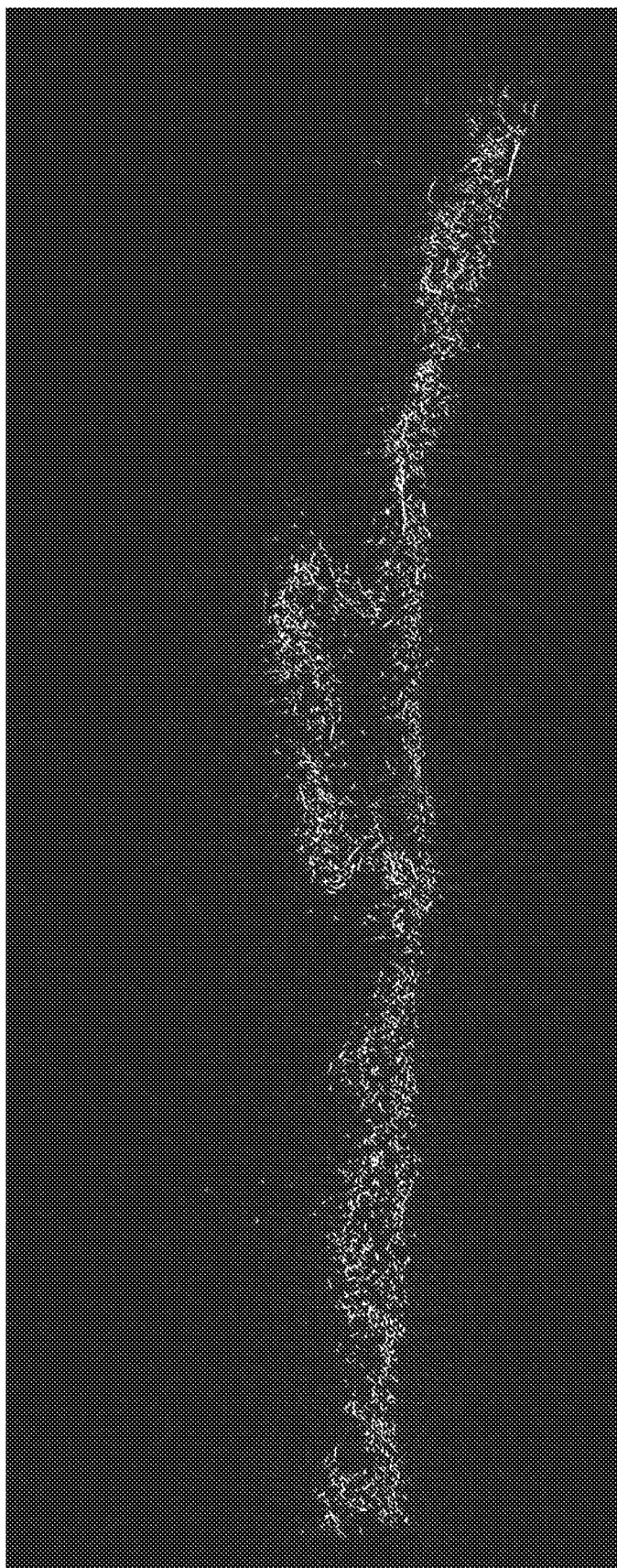
FIG. 5C is a Mirco-CT providing a cross-section of the GentleAbsorb® liner from HUGGIES® Little Snugglers® diapers.

FIGS. 5A-5C provide examples of another beneficial property of the nonwoven material 10 related to fiber orientation. In preferred embodiments of the nonwoven material 10, such as shown in the cross-sections of FIGS. 5A and 5B, at least a majority of the plurality of nodes 12 can be configured such that they have an anisotropy value greater than 1.0 as measured by the Node Analysis Test Method, described in the Test Methods section herein. The nodes 12 have a higher level of fiber alignment in a direction 32 perpendicular to the base plane 18 on the first surface of the nonwoven material 10. FIG. 5C provides a comparative example of a nonwoven material currently used and marketed as a GentleAbsorb® liner in HUGGIES® Little Snugglers® diapers manufactured and sold by Kimberly-Clark Global Sales, LLC, which is described in U.S. Pat. No. 9,327,473. The anisotropy values for the nonwoven materials of FIGS. 5A-5C are shown in Table 2 below. As shown in Table 2, the nonwoven materials 10 from FIGS. 5A and 5B included an anisotropy value greater than 1.0, having anisotropy values of 1.07 and 1.25, respectively.

TABLE 2

Anisotropy Values for Samples from FIGS. 5A-5C

| Sample | Anisotropy Value | Standard Deviation |
| --- | --- | --- |
| Nonwoven from FIG. 5A | 1.07 | 0.04 |
| Nonwoven from FIG. 5B | 1.25 | 0.09 |
| GentleAbsorb ® Liner (FIG. 5C) | 0.94 | 0.03 |

Not to be bound by theory, but it is believed that the improved anisotropy values in the nodes 12 of the nonwoven material 10 described herein can be created by increasing the aspect ratio of the depth of the forming holes 54 compared to the diameter of the forming holes 54, as will be discussed in greater detail below.

Additionally, it is believed that the increased anisotropy values of the nonwoven materials 10 according to this description provide improved compression resistance for the nonwoven material 10 as compared to other nonwoven materials, including as compared to the GentleAbsorb® Liner material. With improved compression resistance, the nonwoven material 10 can maintain its loft through application and use in a variety of environment where it may be exposed to compressive forces. For example, when used in an absorbent article, the nonwoven material 10 can be under compressive forces from its initial packaging state of being in compressed packaging to application on the wearer if the wearer is in a sitting or lying position on the absorbent article. By providing improved resistance to compression, the nonwoven material 10 can help maintain void volume for accepting, transferring, and/or storing body exudates from a wearer. In doing so, the nonwoven material 10 can provide enhanced skin benefits for the wearer by helping keep body exudates away from a wearer's skin and potential product improvements by keeping body exudates away from the edges of the absorbent article, which may be a source of leaks.

Figure 5D:
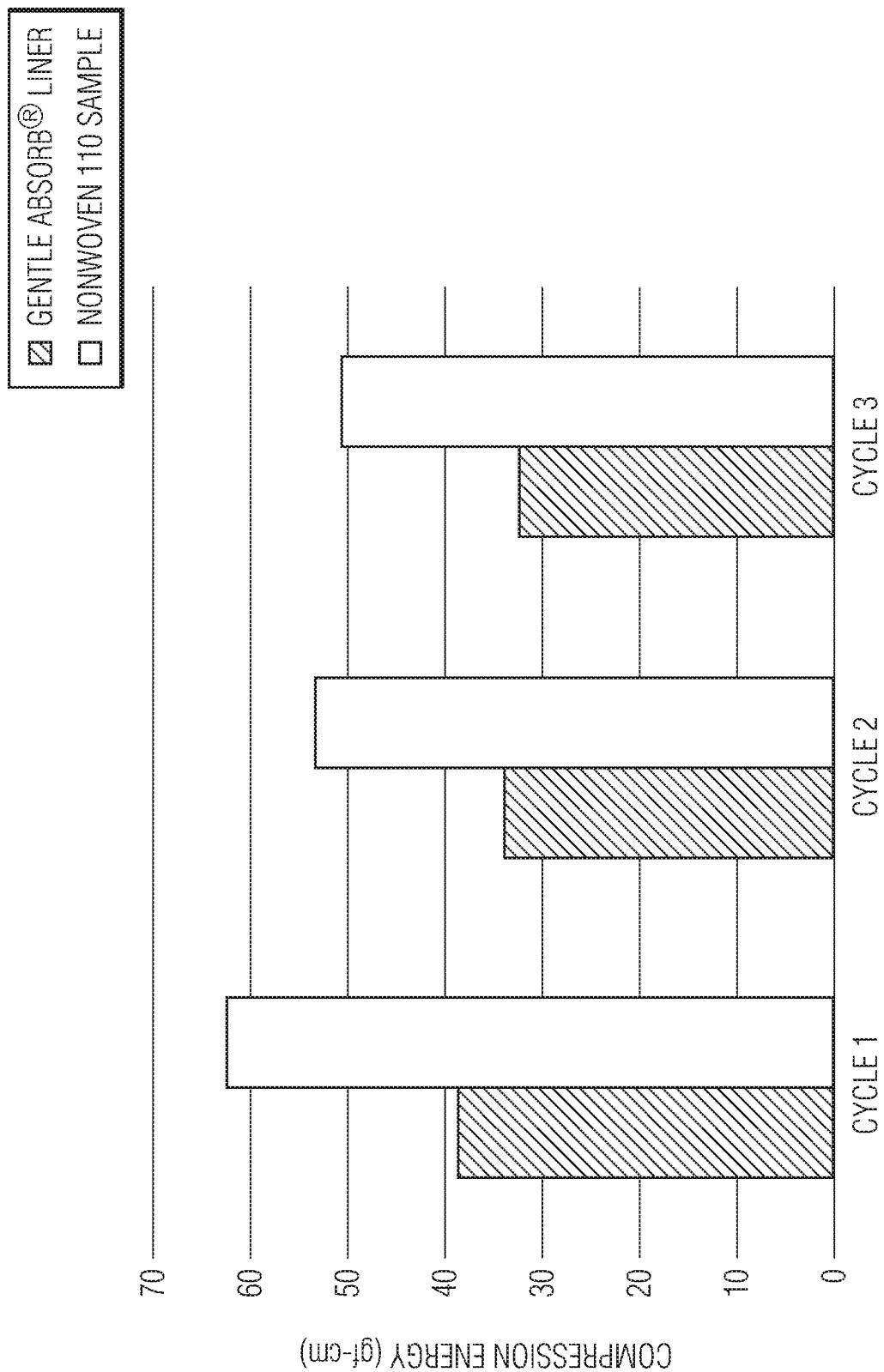
FIG. 5D is a bar graph depicting the results of the testing completed according to the Compression Energy Test Method.
Figure 5E:
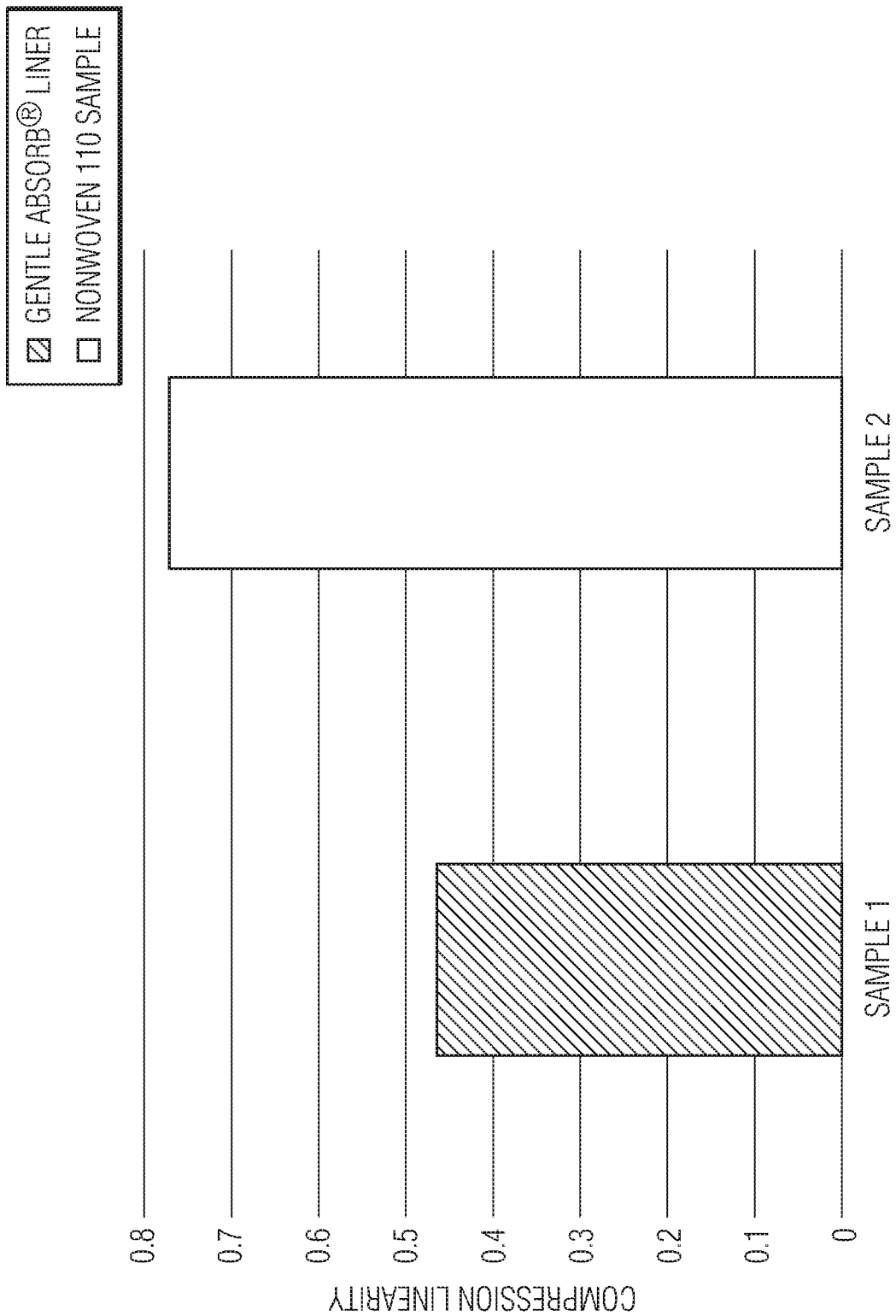
FIG. 5E is a bar graph depicting the results of the testing completed according to the Compression Linearity Test Method

As depicted in FIGS. 5D and 5E, an exemplary nonwoven material 110 described herein (depicted in FIG. 6A) was tested in two compression-related test methods against a comparative example of a nonwoven material currently used and marketed as a GentleAbsorb® liner in HUGGIES® Little Snugglers® diapers manufactured and sold by Kimberly-Clark Global Sales, LLC, which is described in U.S. Pat. No. 9,327,473. A Micro-CT cross-sectional image of a sample of the GentleAbsorb® liner material is depicted in FIG. 5C. FIG. 5D shows the results of the Compression Energy Test and FIG. 5E shows the results of the Compression Linearity Test. The results of this testing will now be discussed.

The Compression Energy Test is described more fully in the Test Methods section herein, but measures the compression resiliency of a material through three cycles of compression by measuring the energy required to compress the nonwoven material from its initial thickness at 5 grams force down to its final thickness at about 1830 grams force (about 10 kPa). As depicted in FIG. 5D, the nonwoven material 110 of the present disclosure required higher amounts of compression energy in each cycle to compress than compared to the compression energy required to compress the control code of the GentleAbsorb® liner, and thus, provides greater compression resilience. In fact, the results of the Compression Energy Testing show that the nonwoven material 110 provide benefits over the control code In particular, the nonwoven material 110 provided a compression energy greater than 40 gr*cm in cycle 1 and greater than 35 gr*cm in cycles 2 and 3. In fact, the nonwoven material provided a compression energy greater than 50 gr*cm in cycles 2 and 3, and greater than 60 gr*cm in cycle 1.

Thus, it is preferable if the nonwoven materials of the present disclosure provide a compression energy greater than 40 gr*cm, more preferably greater than 45 gr*cm, more preferably greater than 50 gr*cm, even more preferably greater than 55 gr*cm, and still even more preferably greater than 60 gr*cm in cycle 1 of the Compression Energy Test. It is preferable if the nonwoven materials of the present disclosure provide a compression energy between 40-65 gr*cm in cycle 1 of the Compression Energy Test. It is also preferable if the nonwoven materials of the present disclosure provide a compression energy greater than 35 gr*cm, more preferably greater than 40 gr*cm, more preferably greater than 45 gr*cm, and even more preferably greater than 50 gr*cm in cycle 2 of the Compression Energy Test. Therefore, it is preferable if the nonwoven materials of the present disclosure provide a compression energy between 40-55 gr*cm in cycle 2 of the Compression Energy Test. It is also preferable if the nonwoven materials of the present disclosure provide a compression energy greater than 35 gr*cm, more preferably greater than 40 gr*cm, more preferably greater than 45 gf*cm, and even more preferably greater than 50 gr*cm in cycle 3 of the Compression Energy Test. It is preferable if the nonwoven materials of the present disclosure provide a compression energy between 40-55 gr*cm in cycle 3 of the Compression Energy Test.

By providing more compression resilience, the nonwoven materials of the present disclosure can provide additional benefits. For example, when the nonwoven material 10 is used in an absorbent article 410, the nonwoven material 10 can maintain void volume for handling body exudates, intaking them into the absorbent assembly 444, which can help keep the skin of the user drier and more comfortable. This benefit may particularly be realized in embodiments in which the nonwoven material 10 is configured in the absorbent article 410 such that nodes 12 extend from the base plane 18 of the first surface 20 of the nonwoven material 10 toward the absorbent body 434. Additionally, by being more compression resilient, the nonwoven material 10 can potentially provide more loft and a softer feel to the skin of a wearer wearing an absorbent article 410.

FIG. 5E depicts the results of the Compression Linearity Test. The Compression Linearity Test, as described fully in the Test Methods section herein, is designed to measure the compression properties of the nonwoven material by compressing the material at a constant rate between two plungers until it reaches a maximum preset force. The displacement of the top plunger compressing the material is detected by a potentiometer. The amount of pressure taken to compress the sample (P, gf/cm$^2$) vs. thickness (displacement) of the material (T, mm) is plotted on the computer screen. The value of compression linearity represents the degree of linearity of the compression curve. The higher the compression linearity value, the more resistant a material is to being compressed. As illustrated in FIG. 5E, the nonwoven material 110 exhibited a compression linearity of about 0.75 whereas the control code of the GentleAbsorb® liner exhibited a compression linearity of less than 0.50. Thus, in preferred embodiments, the nonwoven materials preferably have a compression linearity of greater than 0.50, more preferably greater than 0.55, more preferably greater than 0.60, even more preferably greater than 0.65, and most preferably greater than 0.70. In some embodiments, the nonwoven material can have a compression linearity of between about 0.50 and 1.0, or between about 0.50 and about 0.80.

In some embodiments, the nonwoven material 10 can include side zones and/or end zones which are different than the apertured zone 16. For example, as shown in FIG. 1, the nonwoven material 10 can include a first side zone 26a and a second side zone 26b. The first and second side zones 26a and 26b can be generally parallel to one another and extend in a longitudinal direction 28. The first and second side zones 26a and 26b can be configured such that the first side zone 26a is adjacent to a first side 16a of the apertured zone 16 and the second side zone 26b is adjacent to a second side 16b of the apertured zone 16. Put another way, the apertured zone 16 may be disposed between the first side zone 26a and the second side zone 26b. In at least some embodiments, the side zones 26a, 26b can extend from the front edge 25 of the material 10 all the way to the back edge 27 of the material 10. Additionally, in some embodiments the apertured zone 16 may extend from the front edge 25 of the material 10 all the way to the back edge 27 of the material 10, such that the material 10 does not have any end zones 26c, 26d. Although, in other embodiments the side zones 26a and/or 26b can extend only partially along the length of the nonwoven material 10. In such embodiments, the apertured zone 16 may extend fully between lateral side edges 47, 49 of the nonwoven material 10 along at least a portion of a length of the material 10.

The nonwoven material 10 can have a width 35 defined between the lateral side edges 47, 49. The side zones 26a, 26b have widths 31a, 31b, respectively, while the apertured zone 16 has a width 33. Although shown as constant in FIG. 1, the widths 31a, 31b may vary in other embodiments. For instance, the material 10 could be formed with an apertured zone 16 whose edges curve and/or undulate in the longitudinal direction 28. In such embodiments, the widths 31a, 31b may increase and/or decrease correspondingly to the shape of the apertured zone 16. As used herein, the widths 31a, 31b may refer to the greatest width that the side zones 26a, 26b achieve along the length of the material 10.

In general, it may be beneficial for the side zones 26a, 26b to have widths 31a, 31b which are not too great of a percentage of an overall width 35 of the material 10. For instance, the side zones 26a, 26b may generally have a greater tensile strength than the apertured zone 16. Accordingly, one benefit of the side zones 26a, 26b is that they can help to provide the material 10 with a greater overall tensile strength and thus help the material 10 to be processable within high-speed manufacturing processes where the material 10 is processed under tension (for example, high-speed absorbent article manufacturing processes). However, if the widths 31a, 31b of the side zones 26a, 26b are too great it has been found that the material 10 will curl undesirably when put under tension such that the material 10 may not be processable in desired high-speed manufacturing processes. For example, this curling can cause edges of the nonwoven materials to undesirably fold as the materials traverse along a web path within a manufacturing process. It is believed that the difference in tensile strength between the side zones 26a, 26b and the apertured zone 16 is a key contributing factor to this curling.

In order to help prevent material 10 from curling, or at least curling to such a degree as to impact the processability of the material 10 within a high-speed manufacturing process, it has been found that it is desirable to keep the widths 31a, 31b under certain percentage values of the overall width of the material 10. It is believed that such a feature helps to ensure that the higher tensile strengths of the side zones 26a, 26b do not dominate the performance of the material 10 when subjected to the tensions of high-speed manufacturing processes. It has been found that material 10, and the other materials of the present disclosure, maintain desirable curling properties when subjected to the tensions in typical high-speed manufacturing processes if the widths 31a, 31b are each less than about 20% of the overall width 35 of the material 10. It may be more preferable if the widths 31a, 31b are each less than about 25%, or less than about 20%, or less than about 17.5%, or less than about 15%, less than about 12.5% or less than about 10% of the overall width 35 of the material 10. In at least some of these embodiments, the widths 31a, 31b may each be greater than about 5% of the overall width 35 of the material 10. Consequently, the apertured zone width 33 may be between about 50% and about 90%, or between about 60% and about 90%, or between about 65% and about 90%, or between about 70% and about 90%, or between about 75% and about 90%, or between about 80% and about 90% of the overall width 35 of the material 10.

The widths 31a, 31b may each have similar values. For instance, the widths 31a, 31b may have values such that one of widths 31a, 31b is within about 50% of the value of the other of the widths 31a, 31b, or within about 25% of the value of the other of the widths 31a, 31b.

In embodiments where the material 10 is used within an absorbent article, the side zones 26a, 26b may be used to adhere the material 10 to an absorbent article chassis. In these embodiments, the widths 31a, 31b can be configured to provide a sufficient area to bond the material 10 to the article chassis and to ensure that the material 10 is bonded with sufficient strength such that the material 10 does not delaminate during manufacture or in-use. It has been found that widths 31a, 31b which provide such benefits are between about 10 mm to about 40 mm, or between about 10 mm and about 35 mm, or between about 10 mm and about 30 mm, or between about 10 mm and about 25 mm, or between about 10 mm and about 20 mm.

It has further been found that it in order to manage curling of the material 10 under tension, such as tensions the material 10 may be put under within high-speed manufacturing processes, there is a Tensile Strength Ratio that may be targeted to achieve between the zones 16, 26a, 26b. The Tensile Strength Ratio is described in detail in the discussion of the Tensile Strength Test Method in the Test Methods section herein. In general, the Tensile Strength Ratio compares the additive Tensile Strength of both side zones 26a, 26b against the Tensile Strength of the apertured zone 16. If a preferable Tensile Strength Ratio is achieved, the dimensions of the side zones 26a, 26b do not need to be constrained under a certain percentage of the overall width 35 of the material 10 in order to achieve a desired curling performance. Speaking generally, it has been found that the more even the tensile strength of the material 10 is across its width 35, the less the material 10 curls when put under tension. More specifically, it has been found that material 10, and other materials of the present disclosure, may perform adequately from a curling standpoint if their Tensile Strength Ratio is greater than about 0.8 and less than about 2.5. In other embodiments, the Tensile Strength Ratio may be more preferred to be between about 0.8 and about 2, or between about 0.8 and about 1.75, or between about 0.8 and about 1.5. To determine the tensile strength of the different zones 16, 26a, 26b, the material 10 was subjected to the Tensile Strength Test Method. The Tensile Strength Ratio of the material 10 may then be calculated according to Equation (1) as noted in the Tensile Strength Test Method.

Although the side zones 26a, 26b help to provide greater overall tensile strength to the material 10, the side zones 26a, 26b of the material 10 have not been found to appreciably affect a necking property of the material 10. As used herein, necking is used to refer to the tendency for a material's width to decrease as the material is subjected to increasing longitudinal tension. One material property which is used as a measure of necking is a material's Poisson's ratio. It has been found that the material 10, or more specifically the apertured zone 16 of the material 10, may need to have a relatively low Poisson's ratio in order be processible in a high-speed manufacturing process such as an absorbent article manufacturing process.

As one illustrative example where the material 10 is used as part of an absorbent article, if the material 10 necks too much under tension it may end up not covering a desired width of the absorbent article. Such extreme necking can cause adhesive within the article to be left uncovered by the material 10. This exposed adhesive can undesirably bond other features of the absorbent article together or make opening of such articles difficult. It has been found that beneficial Poisson's ratios of the apertured zone 16 of the material 10 which ensure any necking of the material 10 is not too great, are those ratios that are less than about 3 at 1% strain, or less than about 2.5 at 1% strain, or less than about 2 at 1% strain, or less than about 1.5 at 1% strain. The Poisson's ratio of the apertured zone 16 can be found according to the Poisson's Ratio Test Method as described in the Test Methods section herein.

Another feature of the side zones 26a, 26b is that they may have percent open area values lower than such percent open area values for the apertured zone 16. As described previously, the percent open area value of the apertured zone 16 is desired to be sufficiently high to help produce desirable intake properties of the material 10. The side zones 26a, 26b, conversely, do not need to perform similarly to the apertured zone 16 with respect to intake or other fluid handling properties. Accordingly, in some embodiments the side zones 26a, 26b may have a percent open area value that is less than the percent open area value of the apertured zone 16. It may be more preferable for the side zones 26a, 26b to have percent open area values that are less than about 10%, or less than about 8%, or less than about 6%.

Figure 6A:
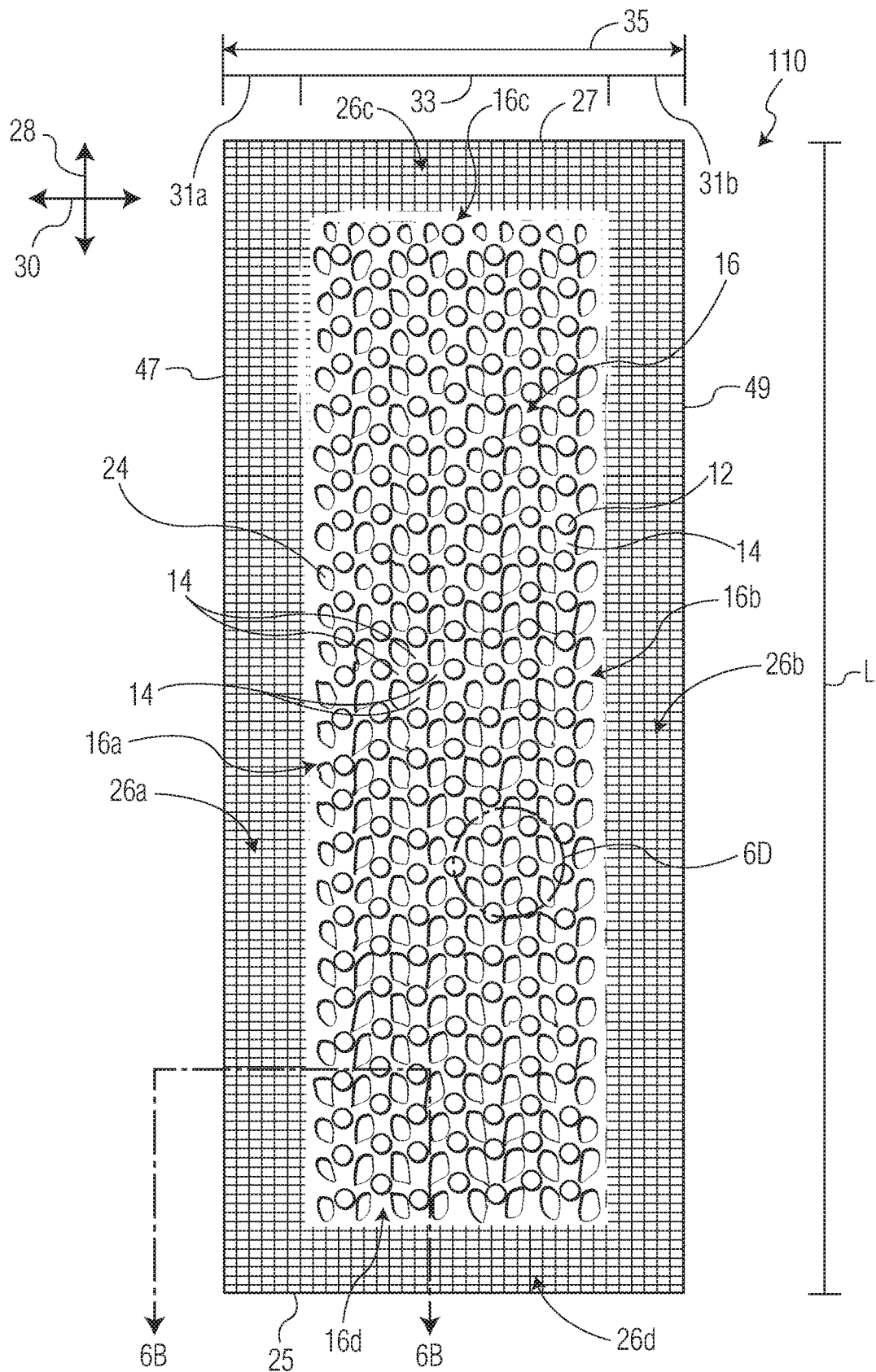
FIG. 6A is a top view of an alternative embodiment of a three-dimensional nonwoven material.
Figure 8A:
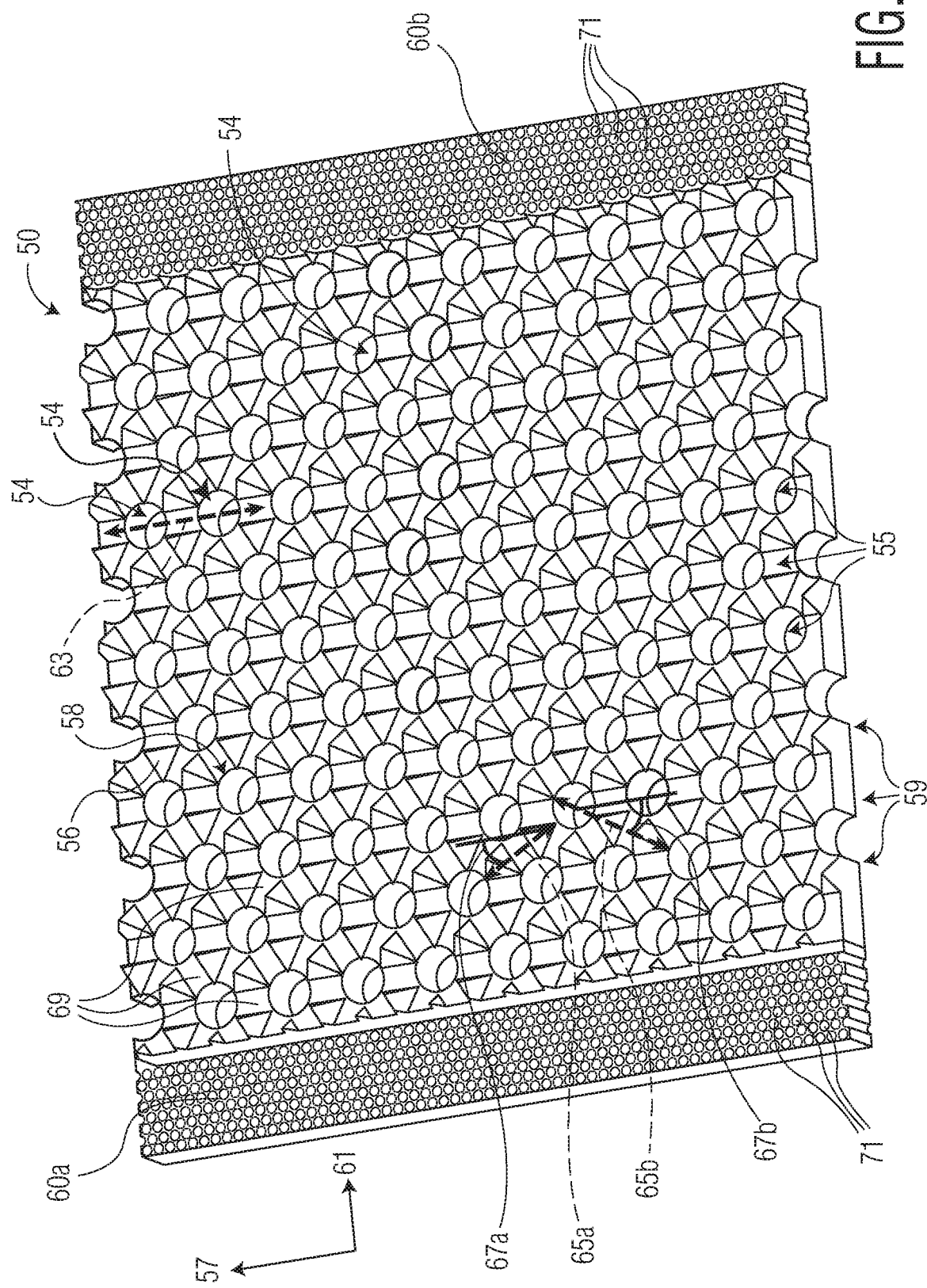
FIG. 8A is a perspective view of a portion of a forming surface that can be utilized in the processes of FIGS. 7A-7C.

It is also the case that the side zones 26a, 26b may have minimum percent open area values. For instance, where the material 10 is a fluid entangled material, the forming process may operate to form micro-apertures 81 within the side zones 26a, 26b. The forming process may additionally or alternatively form areas of greatly reduced fiber density 39, where the process moves fibers from first regions of a forming surface (e.g., portions of the outer surface 58 of the forming surface 50 between apertures 71 as shown in FIG. 8A) used to form the material 10 toward second regions of the forming surface (e.g., apertures 71 as shown in FIG. 8A). These micro-apertures 81 and regions of greatly reduced fiber density 39 can both contribute to the determined percent open area value of the side zones 26a, 26b. These features may be seen in FIG. 6E.

Where the material 10 is a fluid entangled material, it has been found that the percent open area values of the side zones 26a, 26b may generally be greater than about 0.5%, or greater than about 0.6%, or greater than about 0.7% or greater than about 0.8%, or greater than about 0.9%, or greater than about 1.0%, or greater than about 1.25%, or greater than about 2.5%, as determined according to the Material Sample Analysis Test Method. It has been found that the percent open area values of the side zones 26a, 26b in the fluid-entangled nonwoven materials of the present disclosure, such as material 10, are generally greater than the percent open area values of conventional nonwoven materials of similar basis weights, such as spunbond materials, meltblown materials, and even spunlace materials, which do not have openings and/or projections or whereby the openings and/or projections are not formed integrally during formation of such materials.

Figure 6B:
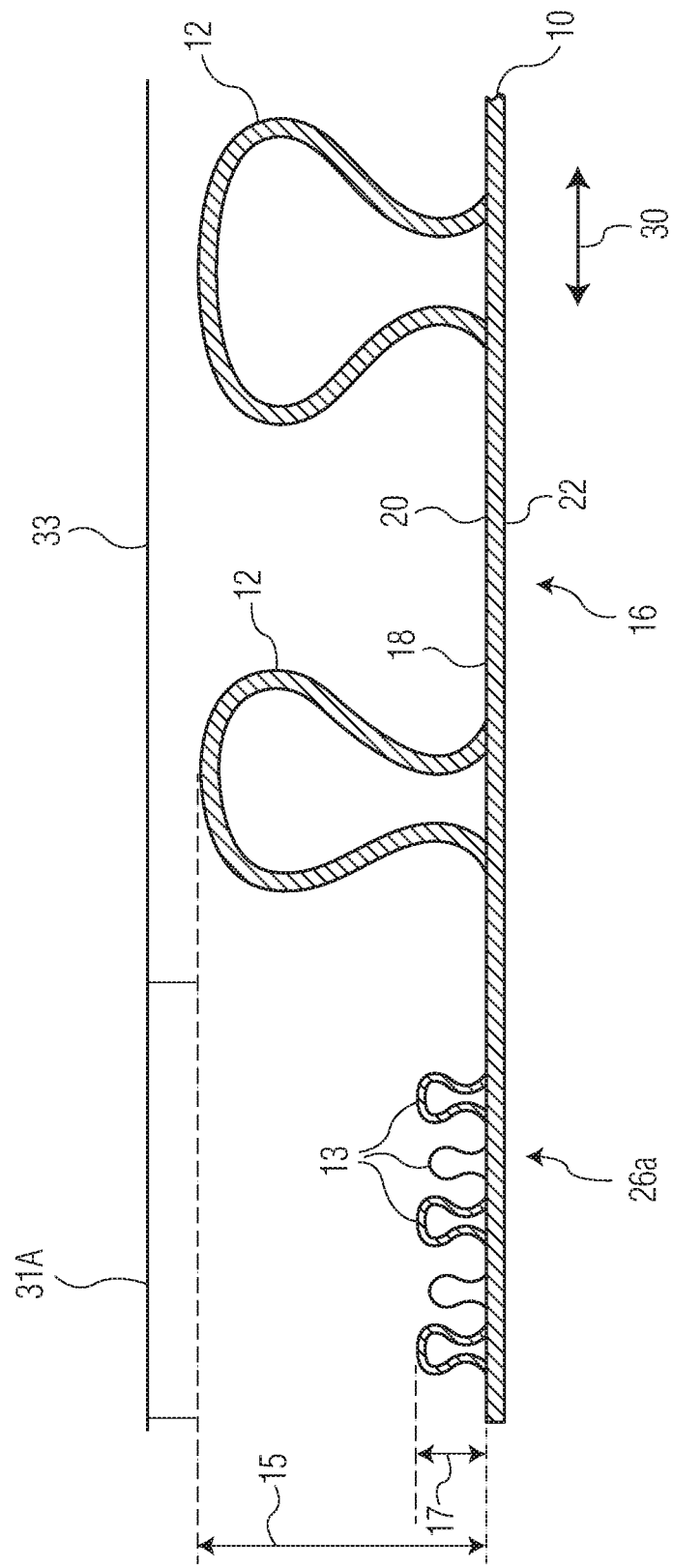
FIG. 6B is a cross-section view of a portion of the material of FIG. 6A as viewed along line 6B-6B.

As described above, where the material 10 is a fluid entangled material, the forming process may form regions of decreased fiber density within the side zones 26a, 26b. Consequently, the formation process may also form regions of increased fiber density within the side zones 26a, 26b, for example, in regions corresponding to apertures 71 in the forming surface 50. As the fibers migrate toward apertures 71 in the forming surface 50, the apertures 71 at least partially fill with fibers, thereby forming micro-bumps 13, as shown in FIG. 6B. This formation process of the micro-bumps 13 may be generally similar to the process of forming the nodes 12 of the apertured zone 16, although the resulting micro-bumps 13 may have a height 17 that is considerably less than the height 15 of the nodes 12. For instance, the micro-bumps 13 may have heights 17 of between about 0.35 mm and about 1.0 mm, or between about 0.4 mm and about 0.9 mm, or between about 0.5 mm and about 0.9 mm, or between about 0.5 mm and about 0.8 mm.

Although optional, the nonwoven material 10 can further include a first end zone 26c and a second end zone 26d. The first end zone 26c and the second end zone 26d can be generally parallel to one another and extend in a lateral direction 30. The first end zone 26c and the second end zone 26d can be configured such that the first end zone 26c is adjacent to a first end 16c of the apertured zone 16 and the second end zone 26d is adjacent to a second end 16d of the apertured zone 16. Any such endzones 26c, 26d may be similar in any fashion to the side zones 26a, 26b as described above.

The openings 24 of the apertured zone 16 can be configured in a variety of shapes and orientations. In the embodiment illustrated in FIGS. 1-4, the openings 24 are each configured to be generally triangular in shape. As best shown in FIGS. 1 and 4, the triangular shape of various openings 24 can be in various orientations. As will be described in more detail below, the openings 24 can be configured in various other shapes and configurations, which can be driven by the process and equipment for how the nonwoven material 10 is manufactured.

Figure 6C:
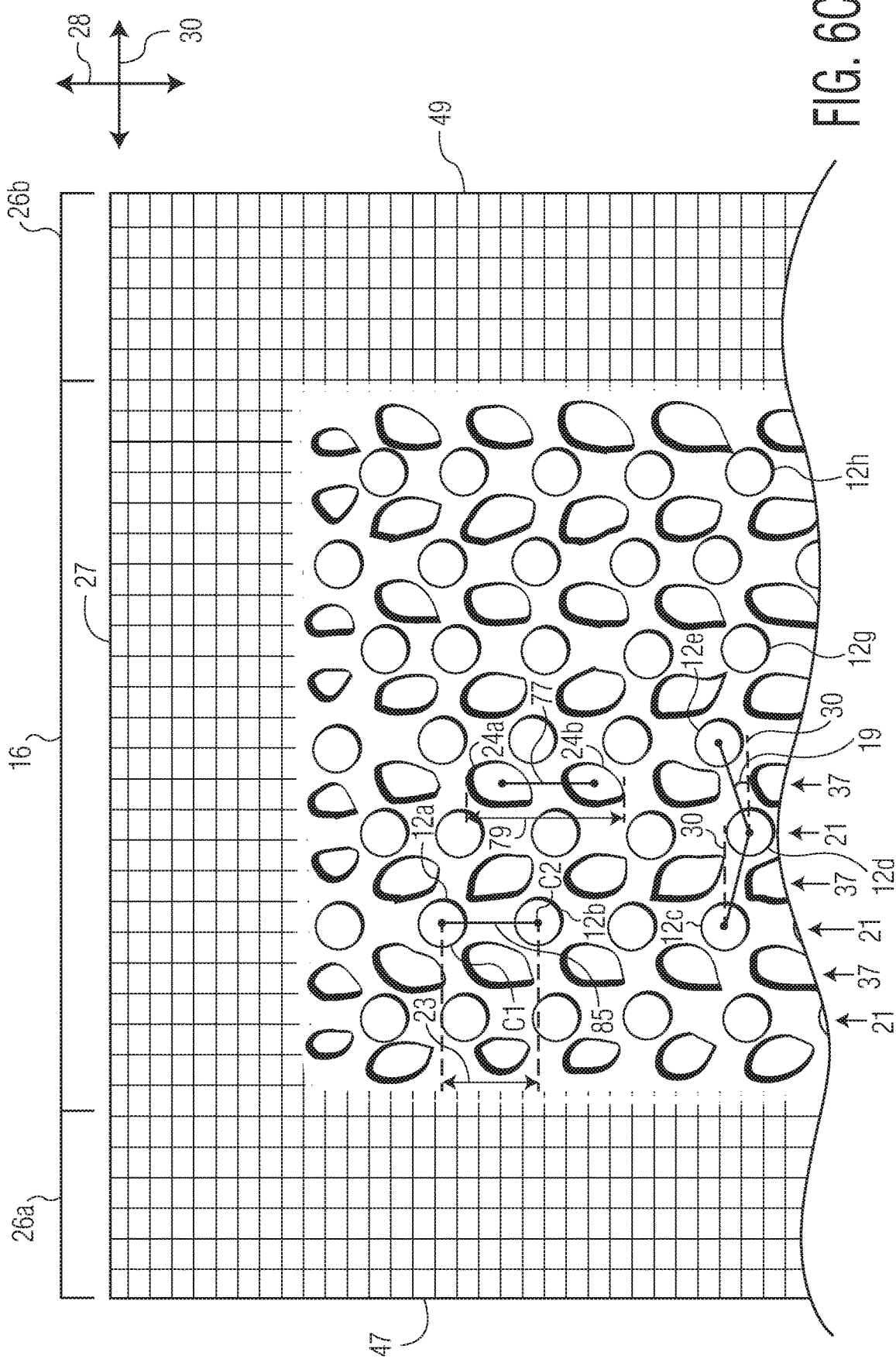
FIG. 6C is a detailed view of a portion of the material of FIG. 6A.
Figure 6D:
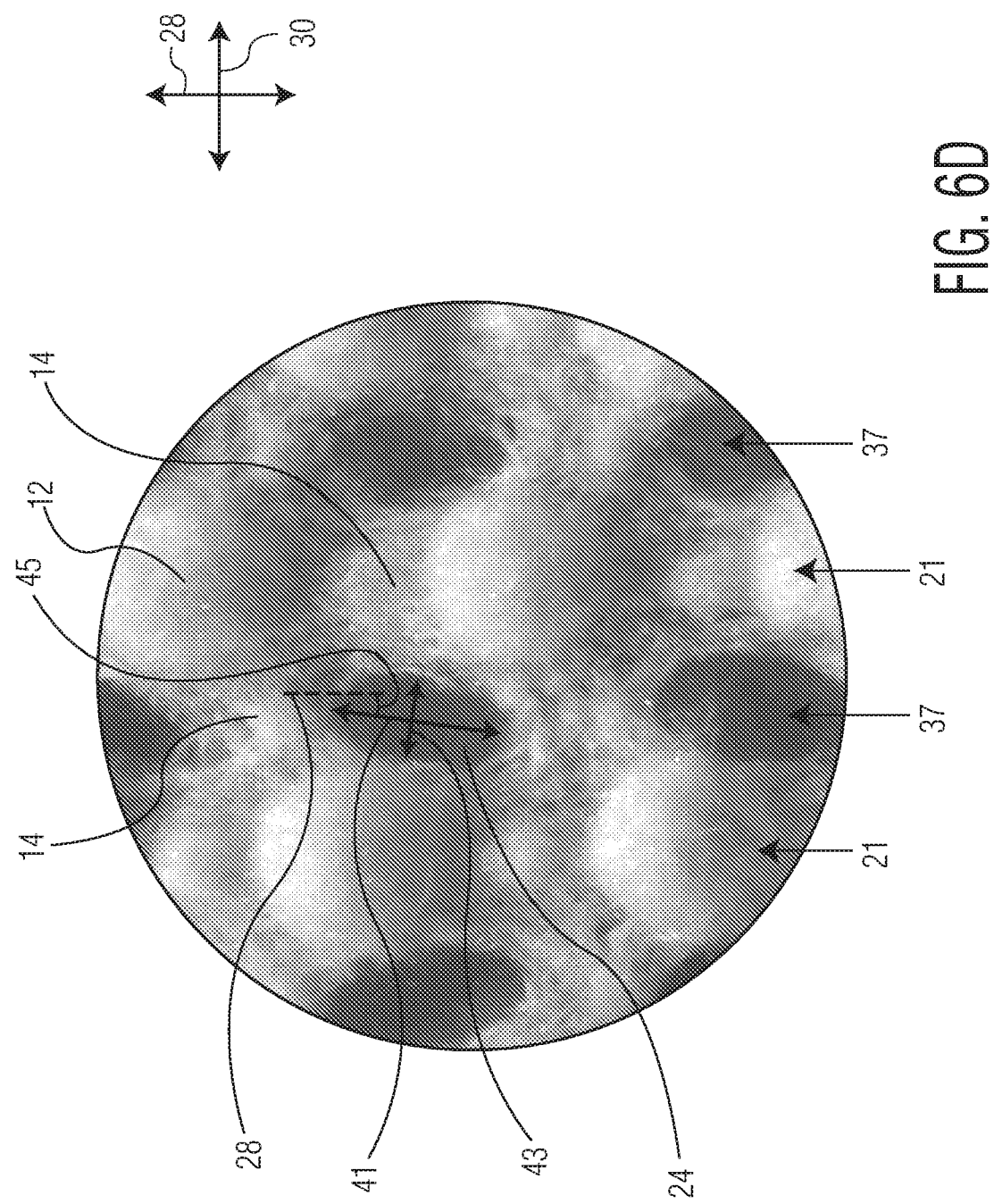
FIG. 6D is an optical image of a portion of the material of FIG. 6A.
Figure 6E:
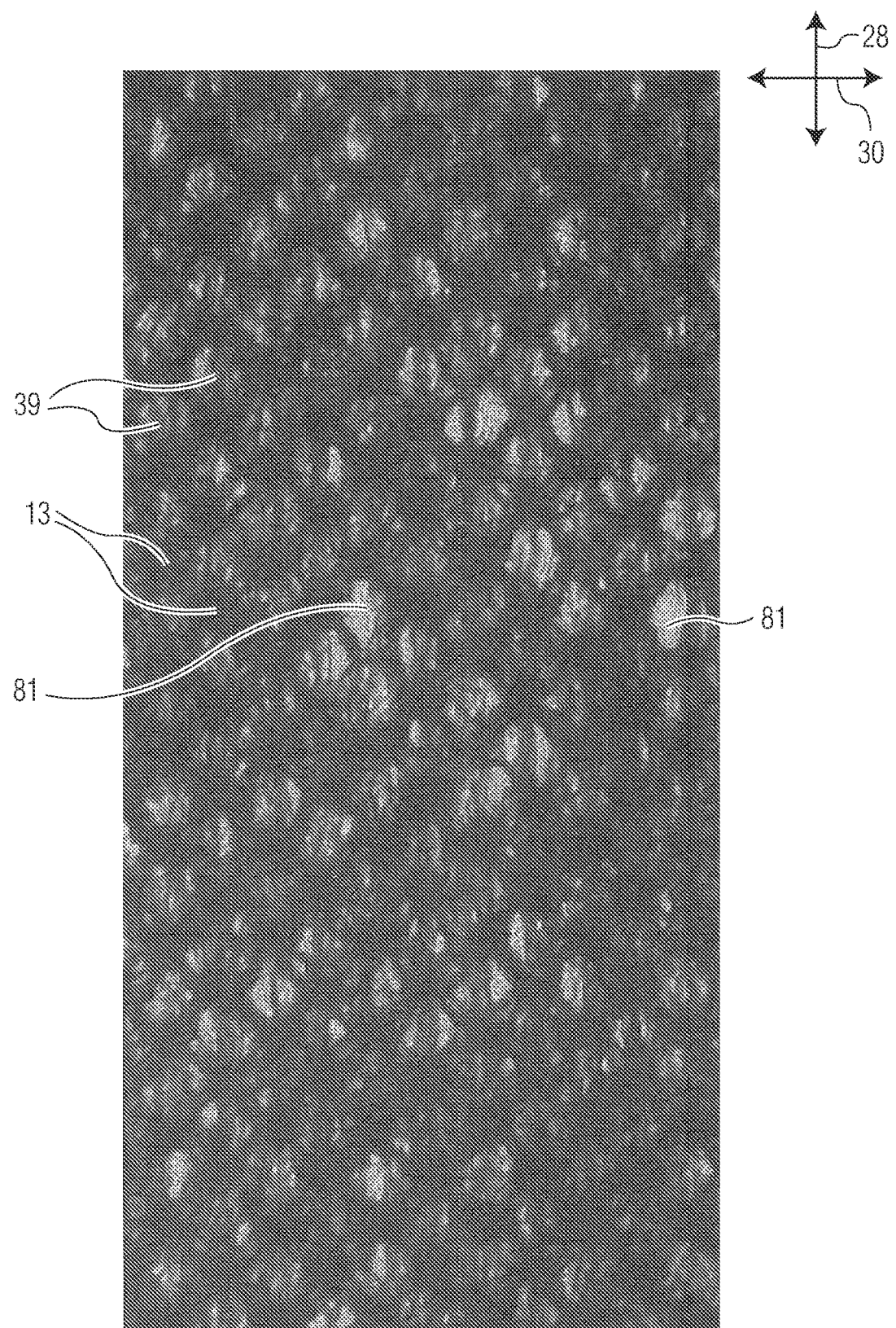
FIG. 6E is a detailed view taken from FIG. 6A illustrating the transmitted light utilized to calculate the percent open area of one exemplary side zone of the nonwoven material of FIG. 6A.

In some particular embodiments, the openings 24 may have a generally ovular shape. For example, as seen in FIGS. 6A, 6C, and 6D, the openings 24 are oblong with generally rounded sides. In at least some embodiments of the present disclosure, the openings 24 may have a major dimension 41 and a minor dimension 43, as shown in FIG. 6D. The major dimension 41 may be the greatest distance between two points on the material 110 surrounding an individual opening 24 while the minor dimension 43 may be the smallest distance between two points on the material 110 surrounding an individual opening 24 and which passes through a center of the opening 24. The center may be the geometric center. In some embodiments according to the present disclosure, it may be beneficial for the major dimension 41 to be oriented such that it extends substantially in the longitudinal direction 28. As used herein, the major dimension 41 is oriented to extend substantially in the longitudinal direction 28 when the major dimension 41 forms an angle 45 with respect to the longitudinal direction 28 of less than forty-five degrees. In some particular embodiments, a majority of the openings 24 may have their major dimension 41 extend substantially in the longitudinal direction 28. In further embodiments, all of the openings 24 may have their major dimension 41 extend substantially in the longitudinal direction 28.

Such embodiments where the major dimension 41 of the openings 24 of the material 110, and other materials of the present disclosure, extend substantially in the longitudinal direction 28 may perform better with respect to intake than other embodiments when used within an absorbent article. As liquid and/or semi-liquid insults impact materials such as material 10, the liquid and/or semi-liquid matter will tend to spread relatively more in the longitudinal direction 28 than the lateral direction 30. Accordingly, where the major dimension 41 of the openings 24 extend substantially in the longitudinal direction 28, there is more opportunity for the liquid and/or semi-liquid matter to transfer through the openings 24 and into any liquid management and holding systems present within the absorbent article (e.g. surge materials and/or absorbent bodies). Some additional benefits may be that the fibers of the surrounding the openings 24 may be oriented relatively more in the longitudinal direction 28, which can enhance a tensile strength of the material 10—an important factor in being able to process such materials in a high-speed converting process.

According to more particular embodiments of the present disclosure, the major dimension 41 of the openings 24 may form an angle 45 with respect to the longitudinal direction 28 of less than about thirty-five degrees, or less than about twenty-five degrees, or less than about fifteen degrees. Of course, it is not the case that all openings 24 may have their major dimension 41 oriented at exactly the same angle 45 with respect to the longitudinal direction 28. For example, even in embodiments where a majority, or more, of the openings 24 have their major dimension 41 extend substantially in the longitudinal direction 28, the specific angles 45 formed by the major dimension 41 of individual openings 24 may range between about zero degrees and about forty-five degrees.

In still further embodiments, different openings 24 may have their major dimension 41 extend substantially in the longitudinal direction 28 but be oriented in opposing lateral directions. For example, as can be seen in FIGS. 6A, 6C, and 6D, various of the openings 24 are depicted having their major dimension 41 oriented such that it extends substantially in the longitudinal direction 28 but toward a first lateral direction. As can be seen, other openings 24 which have their major dimension 41 extend substantially in the longitudinal direction 28 are oriented such that their major dimensions 41 extend toward a second lateral direction, opposite the first lateral direction.

Another feature of the material 110, and other materials contemplated by the present disclosure, is that the aspect ratios of the openings 24 may be contained within a certain range. In at least some embodiments of the present disclosure, an average aspect ratio of the openings of the materials of the present disclosure may be between about 1.3 and about 3.25, or between about 1.4 and about 3.0, or between about 1.3 and about 2.5, or between about 1.3 and about 2.0. These aspect ratio ranges of the openings 24 may help to facilitate intake of insulted bodily fluids, particularly in conjunction with the above described orientations of the openings 24, increasing the overall fluid-handling performance of such materials.

FIG. 6C shows a close-up of a region of the material 110 containing the back edge 27 depicting in greater detail the alignment and orientation of the nodes 12, connecting ligaments 14, and the openings 24 of the material 110. It has been found that particular alignments and orientations of the features 12, 14, and 24 are able to produce desirable properties within materials of the present disclosure. For example, particular alignments and orientations can help to produce desired tensile strength properties and/or desired necking properties for processability of the materials, while still allowing for a highly-open material and thus achieving beneficial fluid-handling properties. Although such alignments and orientations are described with respect to the specific pattern of material 110, it should be understood that other materials contemplated by the present disclosure may achieve such described alignments and orientations in other patterns and materials.

The pattern of nodes 12, connecting ligaments 14, and openings 24 of the material 110 produce series of longitudinally adjacent nodes 12 and laterally adjacent nodes 12. Nodes 12 are longitudinally adjacent, such as nodes 12a and 12b, if a line 85 drawn between centers C1 and C2 does not pass through any openings 24 or other nodes 12 and forms an angle with respect to the longitudinal direction 28 of less than forty-five degrees. Likewise, nodes 12 are laterally adjacent, such as nodes 12*c* and 12*d* (or nodes 12*d* and 12*e*), if a line drawn between centers of the nodes 12*c*, 12*d* does not pass through any openings 24 or any other nodes 12 and forms an angle with respect to the lateral direction 30 of less than forty-five degrees.

In some embodiments, it may be beneficial for the material 110 to have one or more lanes 21 of longitudinally adjacent nodes 12 which extend substantially in the longitudinal direction 28. Such lanes 21 extending substantially in the longitudinal direction 28 may help to enhance a tensile strength of the material 110, thus helping the material 110 to be able to withstand forces present in a high-speed manufacturing process. Lanes 21 which extend substantially in the longitudinal direction 28 may also help to provide beneficial necking performance of the material 110.

A lane 21 comprises a series of connected, longitudinally adjacent nodes 12. A lane 21 is considered to extend substantially in the longitudinal direction 28 where lines drawn between centers of longitudinally adjacent nodes 12 within a lane 21, such as line 85 drawn between centers C1, C2 of nodes 12*a*, 12*b*, form angles with respect to the longitudinal dimension 28 of less than about twenty degrees, more preferably less than about fifteen degrees, even more preferably less than about ten degrees, and still even more preferably less than about five degrees. No angle is shown in FIG. 6C because the angle formed by line 85 with respect to the longitudinal direction 28 is zero.

Where lines drawn between centers of two or more nodes 12 and a center of a connected, longitudinally adjacent reference node 12, each form an angle with respect to the longitudinal direction 28 of less than about twenty degrees, the connected, longitudinally adjacent node 12 which is considered to be in the lane 21 with the reference node 12 is the connected, longitudinally adjacent node 12 for which the line drawn between its center and the center of the reference node 12 forms the smaller angle. Where the lines drawn between the centers of the connected, longitudinally adjacent nodes 12 and a center of the reference node 12 form angles with respect to the longitudinal direction 28 which are equal, the lane 21 ends and none of the connected, longitudinally adjacent nodes 12 are considered to be part of that particular lane 21 with the reference node 12.

In some embodiments, it may be preferable for the material 110 to have at least three lanes 21 which extend substantially in the longitudinal direction 28, or at least four lanes 21 which extend substantially in the longitudinal direction 28, or at least five lanes 21 which extend substantially in the longitudinal direction 28, or at six lanes 21 which extend substantially in the longitudinal direction 28.

In further embodiments, it may be beneficial for the material 110 to have a minimum number of lanes 21 which extend substantially in the longitudinal direction 28 based on a width 33 of the apertured zone 16 of the material 110. To help determine as to whether a material such as material 110 has minimum desired number of lanes 21 which extend substantially in the longitudinal direction 28, a unitless lane number ratio has been developed. This lane number ratio's value is equal to the width 33 of the apertured zone 16 of the material 110, in millimeters, divided by the number of lanes 21 of the material 110 which extend substantially in the longitudinal direction 28. It has been found that materials 110 having a lane number ratio value of less than about 15 may have sufficient tensile strengths to be suitable for use in high-speed manufacturing processes. In more preferred embodiments, the lane number ratio may be less than about 12, or less than about 10, or less than about 8. Although not desired to encompass all suitable contemplated embodiments, the lane number ratio may generally be greater than about 3, or greater than about 4, or greater than about 5.

The lanes 21 which extend substantially in the longitudinally direction 28 have a length 23. The length 23 is the longitudinal length measured between centers of the nodes 12 of the lane 21 extending substantially in the longitudinal direction 28 which are disposed most proximate the back edge 27 and the front edge 25 of the material 10 within the lane 21. In general, it may be beneficial for the lane 21 extending substantially in the longitudinal direction 28 to extend for a length 23 that is greater than about 25% of the overall length L of the material 110, or greater than about 50%, or greater than about 75%, or greater than about 80%, or greater than about 90% of the overall length L of the material 110. In at least some embodiments, the lane 21 extending substantially in the longitudinal direction 28 may extend for the entire length L of the material 110. Although, it should be understood that not all lanes 21 which extend substantially in the longitudinal direction 28 need to extend for such lengths 23. Rather, it may be the case that a majority of the lanes 21 which extend substantially in the longitudinal direction 28 extend for lengths 23 that are greater than the above recited values.

Overall, the alignment of the nodes 12 in the above described manners may function to generally align connecting ligaments 14 in the longitudinal direction 28. For example, the lines 85 drawn between centers of longitudinally adjacent nodes 12 may approximate the location and directions of connecting ligaments 14 which connect such longitudinally adjacent nodes 12. By having such lanes 21 which extend substantially in the longitudinal direction 28, at least some of the connecting ligaments 14 of the material 110 may be substantially longitudinally aligned. These substantially longitudinally aligned connecting ligaments 14 may operate to provide the material 110 with the beneficial tensile strength and/or necking properties as discussed above.

The material 110 may further have one or more lanes 37 of openings 24 which extend substantially in the longitudinal direction 28. Like the lanes 21 of nodes 12, a lane 37 of openings 24 comprises a series of longitudinally adjacent openings 24. Openings 24 are longitudinally adjacent where a line drawn between centers of adjacent openings 24 spans only a single connecting ligament 13 and forms an angle with respect to the longitudinal direction 28 of less than about forty-five degrees. The centers of the openings 24 may be the geometric centers of the openings 24.

A lane 37 is considered to extend substantially in the longitudinal direction 28 where lines drawn between centers of longitudinally adjacent openings 24 within a lane 37, such line 77 drawn between centers of openings 24*a*, 24*b*, form angles with respect to the longitudinal dimension 28 of less than about twenty degrees, more preferably less than about fifteen degrees, even more preferably less than about ten degrees, and still even more preferably less than about five degrees. No angle is shown in FIG. 6C because the angle formed by line 77 with respect to the longitudinal direction 28 is zero degrees.

Where lines drawn between centers of two or more openings 24 and a center of a longitudinally adjacent reference opening 24, each form an angle with respect to the longitudinal direction 28 of less than about twenty degrees, the longitudinally adjacent opening 24 which is considered to be in the lane 37 with the reference opening 24 is the longitudinally adjacent opening 24 for which the line drawn between its center and the center of the reference opening 24 forms the smaller angle. Where the lines drawn between the centers of the longitudinally adjacent openings 24 and a center of the reference opening 24 form angles with respect to the longitudinal direction 28 which are equal, the lane 37 ends and none of the longitudinally adjacent openings 24 are considered to be part of that particular lane 37 with the reference opening 24.

As can be seen in FIG. 6C, the lanes 37 of longitudinally adjacent openings 24 are laterally offset from the lanes 21 of nodes 12 extending substantially in the longitudinal direction 28. That is, at least with respect to the lanes 21 of the nodes 12 extending substantially in the longitudinal direction 28 and lanes 37 of openings 24, there are no openings 24 disposed longitudinally between longitudinally adjacent nodes 12 and this configuration provides a plurality of connecting ligaments 14 that can extend substantially in the longitudinal direction 28 and provide the beneficial properties of nonwoven material 110 tensile strength and reduced necking noted above.

It may further be beneficial for material 110 where laterally adjacent nodes 12 maintain some degree of longitudinal offset. For example, it may be beneficial for lines drawn between centers of laterally adjacent nodes 12, such as nodes 12c and 12d or nodes 12d and 12e, to form angles 19 with respect to the lateral direction 30 of greater than about zero degrees. It may more preferable for the angle 19 to be greater than about ten degrees, or more preferably greater than about fifteen degrees, or more preferably greater than about twenty degrees. In these embodiments, the angle 19 may be less than about twenty-five degrees, or less than about twenty degrees, or less than about fifteen degrees. Of course, it is not necessary that all laterally adjacent nodes 12 within the material 110 have such a feature whereby a line drawn between centers of laterally adjacent nodes 12 forms an angle 19 within the described ranges. In some embodiments, only a majority of the laterally adjacent nodes 12 may have such a feature whereby a line drawn between centers of laterally adjacent nodes 12 forms an angle 19 within the described ranges.

Where the material 110 is a fluid-entangled material, one unique property of the material 110 is a difference in fiber orientation within connecting ligaments 14 which connect longitudinally adjacent nodes 12 and connecting ligaments 14 which connect laterally adjacent nodes 12. It has been found that the anisotropy, one measure of the fiber alignment within a connecting ligament 14, of the connecting ligaments 14 connecting longitudinally adjacent nodes 12 is generally greater than about 1.3, or greater than about 1.4, or greater than about 1.5, according to the Ligament Anisotropy Test Method. In contrast, the anisotropy of the connecting ligaments 14 connecting laterally adjacent nodes 12 is generally less than about than 1.1, or less than about 1.08, or less than about 1.05, according to the Ligament Anisotropy Test Method. These results indicate that the fibers within the connecting ligaments 14 connecting longitudinally adjacent nodes 12 are more generally aligned in a similar direction than the fibers within the connecting ligaments 14 connecting laterally adjacent nodes 12. This feature may further help to lend tensile strength to the material 110 in the longitudinal direction 28.

The nonwoven material 10 can be comprised of various fibers. In one embodiment, the nonwoven material 10 can include synthetic fibers and binder fibers. In preferred embodiments including synthetic fibers and binder fibers, the binder fibers can provide at least about 5% of the plurality of fibers by total weight of the nonwoven material 10, and more preferably, at least about 10% of the plurality of fibers by total weight of the nonwoven material 10. An example of the synthetic fibers that can be used include polyester fibers, polypropylene fiber, and/or bicomponent fibers of polypropylene and polyethylene, however, it can be appreciated that other fibers may be used without departing from the scope of this disclosure. Exemplary binder fibers that can be used are ESC233 binder fibers supplied by FiberVisions, which have a linear density of 3 denier, a cut length of 40 mm, and 18 crimps per inch and ESC215 binder fibers supplied by FiberVisions, which have a linear density of 1.5 denier, a cut length of 40 mm, and 18 crimps per inch. However, it is contemplated that other types of binder fibers may be used.

In some embodiments, the nonwoven material 10 can additionally or alternatively include natural fibers. The fibers of the nonwoven material 10 can be randomly deposited and may be staple length fibers, such as those that are used, for example, in carded webs, airlaid webs, coform webs, etc., and can have a fiber length less than 100 mm, and more typically in the range of 10-60 mm. Alternatively or additionally, the fibers of the nonwoven material can include more continuous fibers such as those that are found in, for example, meltblown or spunbond webs, and can have a fiber length greater than 100 mm.

In some embodiments, the nonwoven material 10 can be configured as a single-layered material. In other embodiments, the nonwoven material 10 can be configured as a laminate, with the laminate including a precursor material to which the nonwoven material 10 can be coupled. An exemplary precursor material, which will be described in relation to FIG. 7 in more detail below, can be a spunbond material.

Figure 6F:
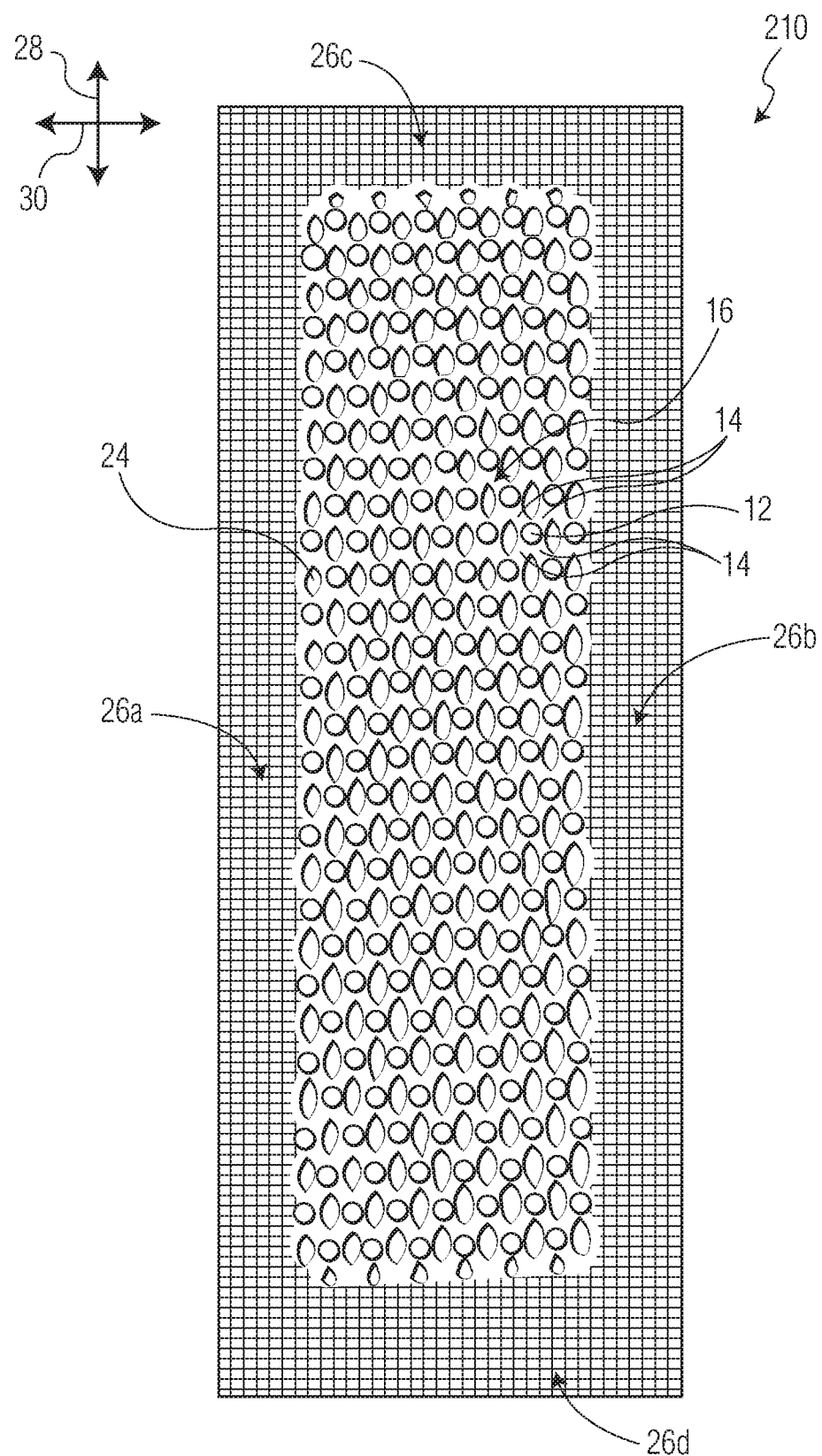
FIGS. 6F and 6G are top views of alternative embodiments of a three-dimensional nonwoven material.
Figure 6G:
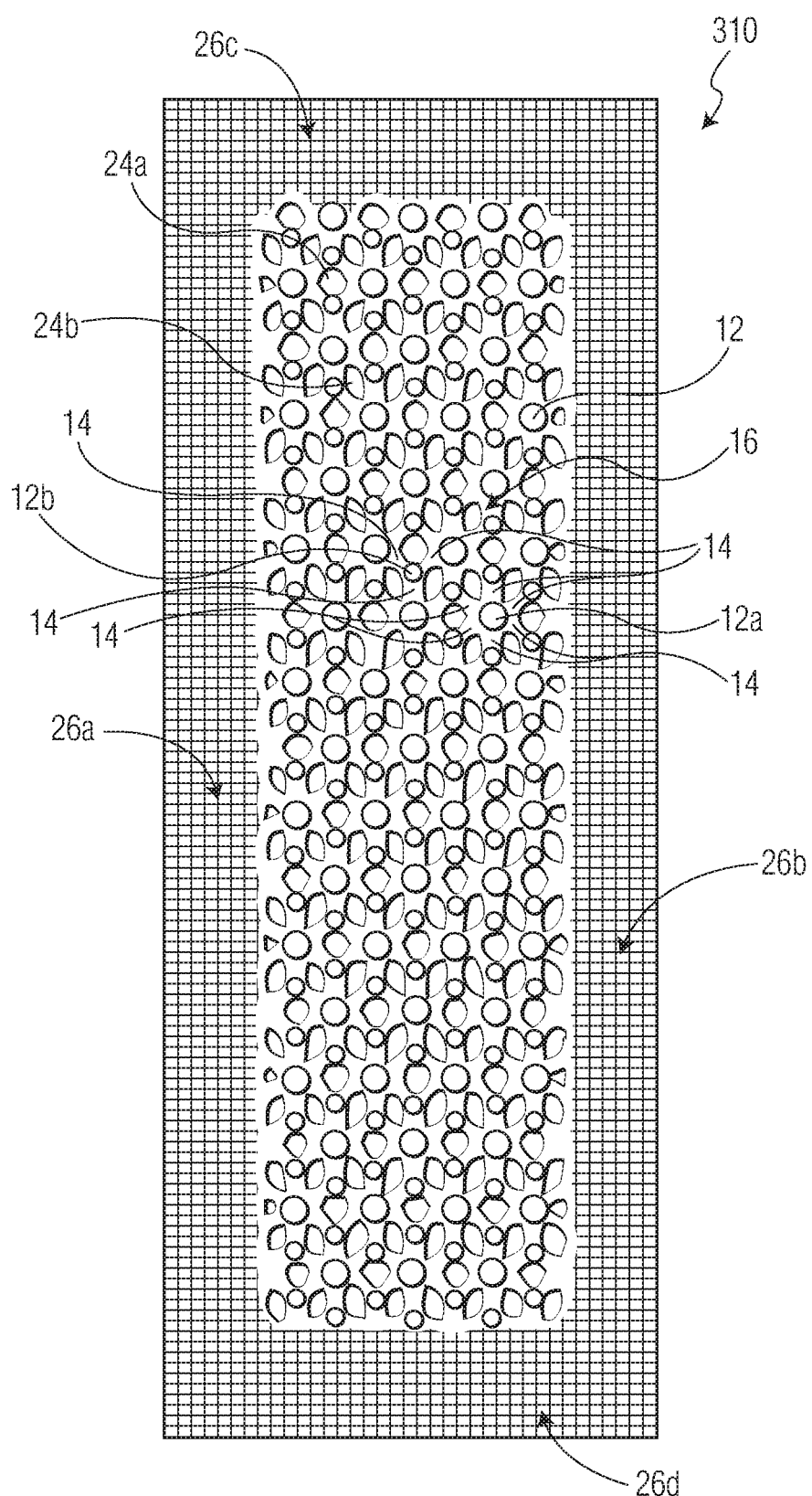

FIGS. 6F and 6G display alternative embodiments of the nonwoven material 210 and 310, respectively. The alternative embodiments demonstrate that the nonwoven material 10, 110, 210, 310 can include nodes 12, connecting ligaments 14, and openings 24 in a variety of configurations. The nonwoven materials 110, 210, 310 of FIGS. 6A-6G, respectively, each include an apertured zone 16 and side zones 26a, 26b, 26c, 26d. In the description of the nonwoven materials 110, 210, 310 of FIGS. 6A-6G, respectively, it is to be noted that not all of the nodes 12, connecting ligaments 14, and openings 24 are labeled for purposes of clarity.

FIG. 6F demonstrates a nonwoven material 210 that includes an apertured zone 16 that includes a plurality of nodes 12 that each have four connecting ligaments 14 connecting to adjacent nodes 12. Some of the openings 24 in the nonwoven material 210 can be configured generally in the shape of a diamond, or may include some curvature to appear in the shape of a lens (biconvex shape with two circular arcs joined at their endpoints) as illustrated in FIG. 6F. As depicted in FIG. 6F, the openings 24 can be configured in the same orientation with respect to one another.

Additionally, the embodiment of the nonwoven material 210 depicted in FIG. 6F may be less preferable in some material-handling respects as compared to the nonwoven material 110 depicted in FIGS. 6A-6D in that the nonwoven material 210 does not include lanes 21 of nodes 12 extending substantially in the longitudinal direction 28 because openings 24 are disposed between various nodes 12 preventing a series of nodes 12 to be configured in a lane 21 of nodes 12 extending substantially in the longitudinal direction 28.

FIG. 6G provides yet another exemplary alternative nonwoven material 310 that includes an apertured zone 16 that includes a plurality of nodes 12. The nonwoven material 310 is configured such that some of the nodes 12 (such as node 12a) have six connecting ligaments 14, while some of the nodes 12 (such as node 12b) have three connecting ligaments 14. As illustrated in FIG. 6G, the ligaments 14 can be of different thicknesses than one another. As also illustrated in FIG. 6G, some of the nodes 12 can be configured to have a different area than other nodes 12. The apertured zone 16 also includes a plurality of openings 24. The nonwoven material 310 is configured such that some of the openings 24 (such as opening 24a) are configured generally in the shape of a hexagon, while some of the openings 24 (such as opening 24b) are configured generally in the shape of a diamond, or with some curvature to appear in the shape of a lens. As illustrated in FIG. 6G, the openings 24 can be configured such that some of the openings 24 can provide different areas than one another.

Figure 7A:
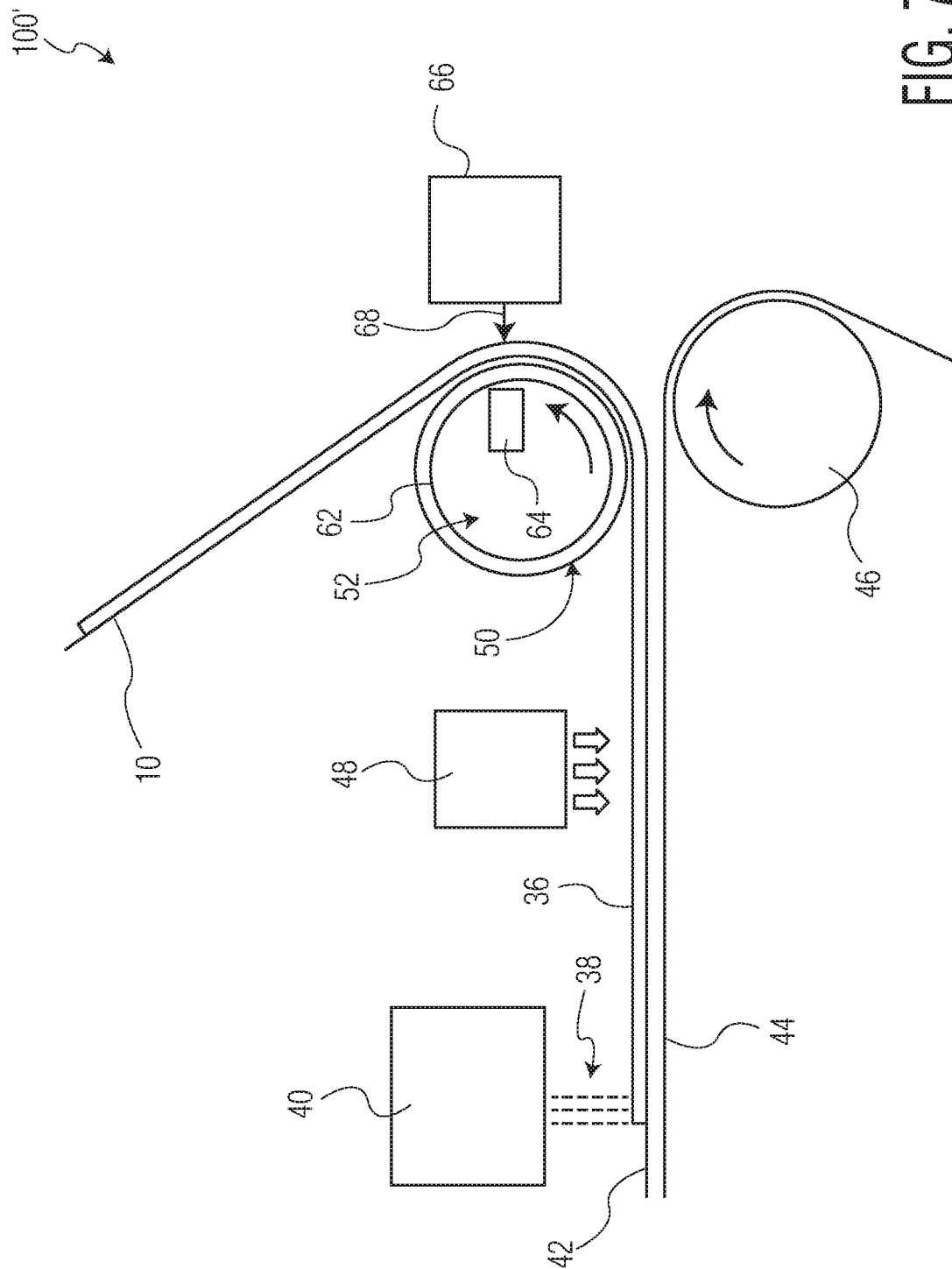
FIG. 7A is a schematic side view of an exemplary apparatus and process for manufacturing a three-dimensional nonwoven according to the present invention.

FIG. 7A illustrates an exemplary process and apparatus 100' for how the nonwoven material 10 of the present disclosure may be manufactured. In FIG. 7A, a precursor web 36 is provided that comprises a plurality of fibers. The precursor web 36 can be formed from a variety of techniques of web forming, such as, but not limited to a wet-laying, a foam-laying, or a carding process. In a preferred embodiment as depicted in FIG. 7A, the precursor web 36 can be formed by a wet-laying process through a fiber and water slurry 38 being deposited from a drum 40 on a precursor forming surface 42. The precursor forming surface 42 as shown in FIG. 7A can be a precursor material, such as a spunbond web. However, it is contemplated that the fiber and water slurry 38 can be deposited directly on a belt, screen, or other surface that provides a precursory forming surface 42. The precursor web 36 can be transferred by a belt 44 driven by a drive roll 46, or other transfer devices known by one of ordinary skill in the art. If the precursor web 36 is formed through a wet-laying process, the precursor web 36 can be dried through known techniques with a dryer 48.

Whether completed off-line or in-line, the precursor web 36 can be transferred to a forming surface 50. The forming surface 50 can be a surface of a texturizing drum 52, such as a forming screen, a portion of exemplary forming surface 50 being shown in greater detail in FIGS. 8A and 8B. The texturizing drum 52 can rotate as shown in FIG. 7A and can be driven by any suitable drive means (not shown) such as electric motors and gearing as are well known to those of ordinary skill in the art. The material forming the texturizing drum 52 may be any number of suitable materials commonly used for such forming drums including, but not limited to, sheet metal, plastics and other polymer materials, rubber, etc.

FIG. 8A provides a first exemplary embodiments of a portion of a forming surface 50. The forming surface 50 can include a plurality of forming holes 54, a plurality of projections 56, and a plurality of connecting ligament forming areas 69. The connecting ligament forming areas 69 can be disposed between the plurality of forming holes 54 and the plurality of projections 56 and can generally be areas of the forming surface 50 that are neither a forming hole 54 nor a projection 56.

As will be discussed in more detail below, the geometry, spacing, and orientation of the forming holes 54, the projections 56, and the connecting ligament forming areas 69 will correspond to the formation of the nodes 12, openings 24, and connecting ligaments 14 in the nonwoven material 10. In fact, the alignment and orientation of these forming holes 54, projections 56, and connecting ligament areas 69 can provide for beneficial properties in the formation of the nonwoven materials as described herein. For example, particular alignments and orientations can help to produce desired tensile strength properties and/or desired necking properties for processability of the materials, while still allowing for a highly-open material and thus achieving beneficial fluid-handling properties. Although such alignments and orientations are described with respect to the specific pattern of forming surface 50 in FIG. 8A and forming surface 50' in FIG. 8B, it should be understood that other forming surfaces contemplated by the present disclosure may achieve such described alignments and orientations in other patterns.

As depicted in FIG. 8A, the forming surface 50 can include a plurality of forming holes 54 that correspond to the shape and pattern of the desired nodes 12 of the nonwoven material 10. While the forming holes 54 depicted in FIG. 8 are round, it should be understood that any number of shapes and combination of shapes can be used depending on the end use application. Examples of additional or alternative possible forming hole 54 shapes include, but are not limited to, ovals, crosses, squares, rectangles, diamond shapes, hexagons and other polygons.

The forming holes 54 can be arranged in a plurality of lanes 55 (three lanes 55 labeled in FIG. 8A) that extend in the longitudinal direction 57 of the forming surface 50. The longitudinal direction 57 of the forming surface 50 can correspond to a circumferential direction, for example, if the forming surface 50 is part of a cylindrical texturizing drum 52. The lanes 55 of forming holes 54 can be formed of longitudinally adjacent forming holes 54. As discussed above with respect to the nodes 12 of the nonwoven material 110 depicted in FIGS. 6A and 6C, forming holes 54 are longitudinally adjacent if a line 63 drawn between centers of forming holes 54 does not pass through any projections 56 or any other forming holes 54 and forms an angle with respect to the longitudinal direction 57 of less than forty-five degrees. Similarly, the forming holes 54 can also be arranged in lanes that extend in the lateral direction 61 of the forming surface 50 if a line drawn between centers of forming holes 54 does not pass through any projections 56 or any other forming holes 54 and forms an angle with respect to the lateral direction 61 of the forming surface 50 of less than forty-five degrees.

Where lines drawn between centers of two or more forming holes 54 and a center of a connected, longitudinally adjacent forming hole 54, each form an angle with respect to the longitudinal direction 57 of the forming surface 50 of less than about twenty degrees, the connected, longitudinally adjacent forming hole 54 which is considered to be in the lane 55 with the reference forming hole 54 is the connected, longitudinally adjacent forming hole 54 for which the line drawn between its center and the center of the reference forming hole 54 forms the smaller angle. Where the lines drawn between the centers of the connected, longitudinally adjacent forming holes 54 and a center of the reference forming hole 54 form angles with respect to the longitudinal direction 57 of the forming surface 57 which are equal, the lane 55 ends and none of the connected, longitudinally adjacent forming holes 54 are considered to be part of that particular lane 55 with the reference forming hole 54.

A lane 55 of forming holes 54 includes a series of connected, longitudinally adjacent forming holes 54. It may be preferable for one or more lanes 55 of forming holes 54 to be configured to extend substantially in the longitudinal direction 57. A lane 55 is considered to extend in the longitudinal direction when lines (such as line 63) drawn between centers of longitudinally adjacent forming holes 54 forms an angle with respect to the longitudinal direction 57 of less than about twenty degrees, more preferably less than about fifteen degrees, even more preferably less than about ten degrees, and still even more preferably less than about five degrees. No angle is shown in FIG. 8A because the angle formed by line 63 with respect to the longitudinal direction 57 is zero degrees. In some preferred embodiments, a majority of the plurality of lanes 55 of forming holes 54 that are arranged in the longitudinal direction 57 can be configured to extend substantially in the longitudinal direction 57. Some embodiments, such as that depicted in FIG. 8A, may have all the lanes 55 of forming holes 54 on the forming surface 50 configured in such a fashion.

In some embodiments, it may be preferable for the forming surface 50 to have at least three lanes 55 of forming holes 54 which extend substantially in the longitudinal direction 57 of the forming surface 50, or at least four lanes 55 which extend substantially in the longitudinal direction 57, or at least five lanes 55 which extend substantially in the longitudinal direction 57, or at six lanes 55 which extend substantially in the longitudinal direction 57.

The lanes 55 of forming holes 54 that extend substantially in the longitudinal direction 57 of the forming surface 50 can have a length that spans the entire forming surface 50 or can form only a portion of the forming surface 50 length in the longitudinal direction 57 (such as a portion of the circumference of the forming surface 50). For example, in some embodiments, it is contemplated that a single lane 55 of forming holes 54 that extends substantially in the longitudinal direction 57 of the forming surface 50 can extend for 5%, or 10%, or 15% or 20%, or 25% or more of a length of the forming surface 50. In some embodiments, the lane 55 of forming holes 54 extending substantially in the longitudinal direction 57 of the forming surface can extend for less than 95%, or less than 90% or less than 85%, or less than 80%, or less than 75% of the length of the forming surface 50. The forming surface 50 can also include a plurality of projections 56 extending away from an outer surface 58 of the forming surface 50. As depicted in FIG. 8, the projections 56 can be configured in a pyramidal geometry, however, the projections 56 can be in various other geometries, cross-sectional shapes, spacings, and orientations. In some embodiments, the plurality of projections 56 can decrease in cross-sectional area as they extend further away from the outer surface 58 of the forming surface 50. For example, the pyramidal shape of the projections 56 depicted in FIG. 8 decrease in area the further the projection 56 extends away from the outer surface 58 of the forming surface 50.

Overall, the alignment of the forming holes 54 to form lanes 55 of forming holes 54 extending substantially in the longitudinal direction 57 can align connecting ligament forming areas 69 in the longitudinal direction 57. For example, the lines 63 drawn between centers of longitudinally adjacent forming holes 54 may approximate the location and directions of connecting ligament forming areas 69 which connect such longitudinally adjacent forming holes 54. By having such lanes 55 of forming holes 54 which extend substantially in the longitudinal direction 57, at least some of the connecting ligament forming areas 69 may be substantially longitudinally aligned. These substantially longitudinally aligned connecting ligament forming areas 69 can lead to a nonwoven material 110 such as discussed above that can provide beneficial tensile strength and/or necking properties yet maintain an adequate percent open area.

The projections 56 can be arranged in a plurality of lanes 59 (three lanes 59 labeled in FIG. 8A) that extend in the longitudinal direction 57 of the forming surface 50. The lanes 59 of projections 56 can be formed of a series of connected, longitudinally adjacent projections 56. As discussed above with respect to the openings 24 in the nonwoven material 110 depicted in FIGS. 6A and 6C, projections 56 are longitudinally adjacent where a line (such as line 65a or 65b in FIG. 8A) does not pass through any forming holes 54 or any other projections 56 and spans across only a single connecting ligament forming area 69 and forms an angle with respect to the longitudinal direction 57 of the forming surface 50 of less than about forty-five degrees. The centers of the projections 56 may be the geometric centers of the projections 56. Similarly, the projections 56 can also be laterally adjacent when if a line drawn between centers of projections 56 does not pass through any forming holes 54 or any other projections 56 and the line only spans across a single connecting ligament forming area 69 and forms an angle with respect to the lateral direction 61 of the forming surface 50 of less than forty-five degrees.

In some embodiments, a majority of the plurality of lanes 59 of projections 56 extending in the longitudinal direction 57 are laterally offset from a nearest adjacent lane 55 of forming holes 54 extending substantially in the longitudinal direction 57. With such a configuration, such as depicted in FIG. 8A (as well as in an alternative embodiment depicted in FIG. 8B), the connecting ligament forming areas 69 disposed between forming holes 54 can extend substantially in the longitudinal direction 57. As a result, nonwoven materials 10 formed from such a forming surface 50 can have connecting ligaments 14 that extend substantially in the longitudinal direction 28 of the nonwoven material 110, such as described above with respect to nonwoven material 110 in FIGS. 6A and 6C. As noted above, this can provide beneficial properties of improved tensile strength and reduced necking of the nonwoven material 110 while maintaining a desirable percent open area of the apertured zone 16 of the nonwoven material 110.

In some embodiments, the projections 56 within each lane 59 can be configured such that longitudinally adjacent projections 56 can form a line 65a or 65b that forms an angle 67a, 67b, respectively, with the longitudinal direction 57. In some embodiments, this angle 67a or 67b can be between 15 degrees to 60 degrees. As depicted in FIG. 8A, longitudinally adjacent projections 56 within a lane 59 of projections 56 can form a zig-zag type pattern in the longitudinal direction 57 such that each projection 56 within a single lane 59 of projections 56 is laterally offset in the lateral direction 61 from its prior projection 56 and its successive projection 56 in the lane 59 in the same lateral direction 61.

However, in some preferred embodiments such as the embodiment depicted in the detailed top view of an alternative forming surface 50' in FIG. 8B, the forming surface 50' can be configured to include one or more lanes 59 of projections 56 that extend substantially in the longitudinal direction 57. A lane 59 is considered to extend in the longitudinal direction when lines (such as line 65) drawn between centers of longitudinally adjacent projections 56 forms an angle with respect to the longitudinal direction 57 of less than about twenty degrees, more preferably less than about fifteen degrees, even more preferably less than about ten degrees, and still even more preferably less than about five degrees. No angle is shown in FIG. 8B because the angle formed by line 65 with respect to the longitudinal direction 57 is zero degrees. In some embodiments, a majority of the plurality of lanes 59 of projections 56 extending in the longitudinal direction 57 are configured to extend substantially in the longitudinal direction 57. And in some embodiments, substantially all or all of the plurality of lanes 59 of projections 56 can be configured in this manner.

Still referring to FIG. 8B, each projection 56 can include a length 73 and a width 75. The length 73 can also be referred to as the major dimension for the projection 56 and the width 75 can be referred to as the minor dimension for the projection 56. As noted above, the length 73 compared to the width 75 of the projection 56 can result in forming an aspect ratio for an opening 24 in the nonwoven material 110, as discussed above with respect FIG. 6D. Preferably, an aspect ratio of the length 73 to the width 75 of the projection 56 is greater than 1.0. In some embodiments, the aspect ratio of the length 73 to the width 75 of the projection 56 is from about 1.3 and about 3.25, or between about 1.4 and about 3.0, or between about 1.3 and about 2.5, or between about 1.3 and about 2.0 In some embodiments, the length 73 of the projection 56 can be oriented such that the length 75 extends substantially in the longitudinal direction 57 of the forming surface 50. As used herein, a projection 56 having its length 73 oriented in the longitudinal direction 57 is meant to encompass projections 56 having a direction of their length 73 form an angle of less than 45 degrees with the longitudinal direction 57 of the forming surface 50. In some embodiments, such as shown in FIG. 8B, a plurality of the projections 56 within a lane 59 can be configured in such a manner. In some embodiments, substantially all or all of the projections 56 within a lane 59 of projections 56 can be configured in such a manner. As also depicted in FIG. 8B, adjacent lanes 59 of projections 56 can be configured such that the angular orientation of the major dimension (or length 73) of projections 56 are oriented in different lateral directions. For example, the left-most lane 59 of projections 56 has projections 56 with their length 73 being oriented in a first lateral direction whereas the second lane 59 of projections 56 has projections 56 with their length 73 being oriented in a second lateral direction that is opposite the first lateral direction. In some embodiments, the projections 56 in adjacent lanes 59 of projections 56 can be configured to have the projections 56 oriented such that their lengths 73 extend in lateral directions that are mirror images of one another.

The forming surface 50 can also include one or more areas 60a, 60b that are substantially free from projections 56. The areas 60a, 60b, as will be discussed in further detail below, can correspond to the side zones 26a, 26b in the nonwoven material 10. In some embodiments, the areas 60a, 60b corresponding to the side zones 26a, 26b can include apertures 71. However, in preferred embodiments, if included, the apertures 71 in the areas 60a, 60b are smaller in cross-sectional area than the forming holes 54 in the forming surface 50 and can help with fluid removal during the fluid entangling process. For example, an average area of the apertures 71 in the areas 60a, 60b can be less than an average area of the forming holes 54 in the forming surface 50. The apertures 71 in the areas 60a, 60b can lead to formation of micro-bumps 13, as depicted in FIG. 6B. The area of the outer surface 58 of the forming surface 50 between the apertures 71 in zones 60a, 60b can form micro-apertures 81 and/or areas of lower fiber density 39.

Referring back to FIG. 7A, typically, the perforated forming surface 50 is removably fitted onto and over an optional porous inner drum shell 62 so that different forming surfaces 50 can be used for different end product designs. The porous inner drum shell 62 interfaces with a fluid removal system 64 which facilitates pulling the entangling fluid and fibers down into the forming holes 54 in the forming surface 50, thereby forming the nodes 12 in the nonwoven material 10. The porous inner drum shell 62 also acts as a barrier to retard further fiber movement down into the fluid removal system 60 and other portions of the equipment thereby reducing fouling of the equipment. The porous inner drum shell 62 rotates in the same direction and at the same speed as the texturizing drum 52. In addition, to further control the height of the nodes 12 on the nonwoven material 10, the distance between the inner drum shell 62 and the outer surface 58 of the forming surface 50 can be varied. Generally, the spacing between the outer surface 58 of the forming surface 50 and the outer surface of the inner drum shell 64 will range between about 0 and about 5 mm. Other ranges can be used depending on the particular end-use application and the desired features of the nonwoven material 10.

The depth of the forming holes 54 in the texturizing drum 52 or other projection forming surface 50 can be between 1 mm and 10 mm but preferably between around 3 mm and 6 mm to produce nodes 12 with the shape most useful in the expected common applications. The forming hole 54 cross-section diameter (or major dimension) may be between about 2 mm and 10 mm but it is preferably between 3 mm and 6 mm as measured along the major axis and the spacing of the forming holes 54 on a center-to-center basis can be between 3 mm and 10 mm but preferably between 4 mm and 7 mm. The pattern of the spacing between forming holes 54 may be varied and selected depending upon the particular end use. Some examples of patterns include, but are not limited to, aligned patterns of rows and/or columns, skewed patterns, hexagonal patterns, wavy patterns and patterns depicting pictures, figures and objects.

The cross-sectional dimensions of the forming holes 54 and their depth influence the cross-section and height of the nodes 12 produced in the nonwoven material 10. Generally, forming hole 54 shapes with sharp or narrow corners at the leading edge of the forming holes 54 as viewed in the machine direction should be avoided as they can sometimes impair the ability to safely remove the nonwoven material 10 from the forming surface 50 without damage to the nodes 12. In addition, the thickness/hole depth in the forming surface 50 will generally tend to correspond to the depth or height of the nodes 12 in the nonwoven material 10. It should be noted, however, that each of the hole depth, spacing, size, shape and other parameters may be varied independently of one another and may be varied based upon the particular end use of the nonwoven material 10 being formed.

Not to be bound by theory, but it is believed that specific aspect ratios of the depth of the forming holes 54 to the diameter (or major dimension) of the forming holes 54 contribute to increased anisotropy of the nodes 12 in the nonwoven material 10. The term "major dimension" is used in the context if the forming holes 54 are not circular in shape, for example, if the forming holes 54 are shaped as an ellipse, the major dimension would be the length of the ellipse along its major axis. It is believed that an aspect ratio of the depth of a forming hole 54 to the diameter (or major dimension) of the forming hole 54 greater than 1.0 is believed to lead to increased anisotropy of the nodes 12 of the nonwoven material 10. In some preferred embodiments, the aspect ratio of the depth of the forming holes 54 to the diameter (or major dimension) of the forming holes 54 can be between from 1.0 to 1.2. As noted above, increased anisotropy in the nodes 12 in the nonwoven material 10 can provide improved compression properties of the nonwoven material 10.

In the embodiment depicted in FIG. 7A, the forming surface 50 is shown in the form of a forming screen placed on a texturizing drum 52. It should be appreciated however that other means may be used to create the forming surface 50. For example, a foraminous belt or wire (not shown) may be used which includes forming holes 54 formed in the belt or wire at appropriate locations. Alternatively, flexible rubberized belts (not shown) which are impervious to the pressurized fluid entangling streams except in the location of the forming holes 54 may be used. Such belts and wires are well known to those of ordinary skill in the art as are the means for driving and controlling the speed of such belts and wires. A texturizing drum 52 is more advantageous for formation of the nonwoven material 10 according to the present disclosure because it can be made with an outer surface 58 between the forming holes 54 and projections 56 that is smooth and impervious to entangling fluid, and which does not leave a wire weave pattern on the nonwoven material 10 as wire belts tend to do.

In embodiments where the forming surface 50 forms a portion of a texturizing drum 52 as a forming screen, the forming surface 50 and its features can be achieved through using a variety of techniques. For example, the forming surface 50 and its features of forming holes 54 and projections 56 can be formed by casting, molding, punching, stamping, machining, laser-cutting, water jet cutting, and 3D printing, or any other suitable methodology.

The exemplary apparatus and method 100' can also include one or more fluid entangling devices 66. The most common fluid used in this regard is referred to as spunlace or hydroentangling technology which uses pressurized water as the fluid for entanglement. As such, the fluid entangling device 66 can include a plurality of high pressure fluid jets (not shown) to emit a plurality of pressurized fluid streams 68. These fluid streams 68, which are preferably water, can be directed towards the precursor web 36 on the forming surface 50 and can cause the fibers to be further entangled within nonwoven material 10 and/or the precursor forming surface 42 (in the case the precursor forming surface is an underlying web of material). The fluid streams 68 can also cause the fibers in the precursor web 36 to be directed into the forming holes 54 and out of the base plane 18 of the first surface 20 of the nonwoven material 10 and into the Z-direction 38 perpendicular to the base plane 18 to form the nodes 12 in the nonwoven material 10 (see FIGS. 2 and 3). The fluid streams 68 can also provide for at least a majority of the plurality of nodes 12 to be configured such that they have an anisotropy value greater than 1.0, as previously discussed above. The fluid streams 68 can also cause the fibers in the precursor web 36 to be directed around the projections 56 on the forming surface 50 into the connecting ligament forming areas 69 to form the plurality of connecting ligaments 14 and the plurality of openings 24 on the nonwoven material 10.

In FIG. 7A a single fluid entangling device 66 is shown, however, depending on the level of entanglement needed and the particular dimensions and qualities of the nonwoven material 10 desired, a plurality of such fluid entangling devices 66 can be used. The entangling fluid streams 68 of the fluid entangling devices 66 emanates from injectors via jet packs or strips (not shown) consisting of a row or rows of pressurized fluid jets with small apertures of a diameter usually between 0.08 and 0.15 mm and spacing of around 0.5 mm in the cross-machine direction. The pressure in the jets can be between about 5 bar and about 400 bar but typically is less than 200 bar except for heavy nonwoven materials 10 and when fibrillation is required. Other jet sizes, spacings, numbers of jets and jet pressures can be used depending upon the particular end application. Such fluid entangling devices 66 are well known to those of ordinary skill in the art and are readily available from such manufacturers as Fleissner of Germany and Andritz-Perfojet of France.

The fluid entangling devices 66 will typically have the jet orifices positioned or spaced between about 5 mm and about 20 mm, and more typically between about 5 and about 10 mm from the forming surface 50 though the actual spacing can vary depending on the basis weights of the materials being acted upon, the fluid pressure, the number of individual jets being used, the amount of vacuum being used via the fluid removal system 64 and the speed at which the equipment is being run.

In the embodiment shown in FIG. 7A, the fluid entangling device 66 is a conventional hydroentangling device the construction and operation of which is well known to those of ordinary skill in the art, such as, for example, U.S. Pat. No. 3,485,706 to Evans, the contents of which is incorporated herein by reference in its entirety for all purposes. Also see the description of the hydraulic entanglement equipment described by Honeycomb Systems, Inc., Biddeford, Me., in the article entitled "Rotary Hydraulic Entanglement of Nonwovens", reprinted from INSIGHT '86 INTERNATIONAL ADVANCED FORMING/BONDING Conference, the contents of which is incorporated herein by reference in its entirety for all purposes.

The speed of the rotation of the drive roll 46 and the texturizing drum 52 can be set at various speeds with respect to one another. In some embodiments, the speed of the rotation of the drive roll 46 and the texturizing drum 52 can be the same. In other embodiments, the speed of the rotation of the drive roll 46 and the texturizing drum 52 can be different. For example, in some embodiments, the speed of the texturizing drum 52 may be less than the speed of the drive roll 46 to provide for overfeeding of the precursor web 36 on the forming surface 50 on the texturizing drum 52. Such overfeeding can be used to provide varied properties in the nonwoven material 10, such as, improved formation of nodes 12 in the nonwoven material 10 and increased height of the nodes 12.

After the fluid entanglement occurs from the fluid entangling streams 68 by the fluid entanglement device 66, the precursor web 36 becomes a hydroentangled web forming the nonwoven material 10 described above that includes a plurality of nodes 12, a plurality of connecting ligaments 14 interconnecting the plurality of nodes 12, and a plurality of openings 24 as described above. The apparatus 100' and process can further include removing the hydroentangled web of nonwoven material 10 from the forming surface 50 and drying the hydroentangled web to provide a three-dimensional nonwoven material 10. Drying of the nonwoven material 10 can occur through known techniques by one of ordinary skill in the art. In embodiments where the precursory web includes binder fibers, the drying of the nonwoven material 10 can activate the binder fibers. Activating the binder fibers can assist with the preservation of the three-dimensionality of the nonwoven material 10 by helping to preserve the geometry and height of the nodes 12 that extend away from the base plane 18 on the first surface 20 of the nonwoven material 10 (as depicted in FIGS. 2 and 3).

Figure 7B:
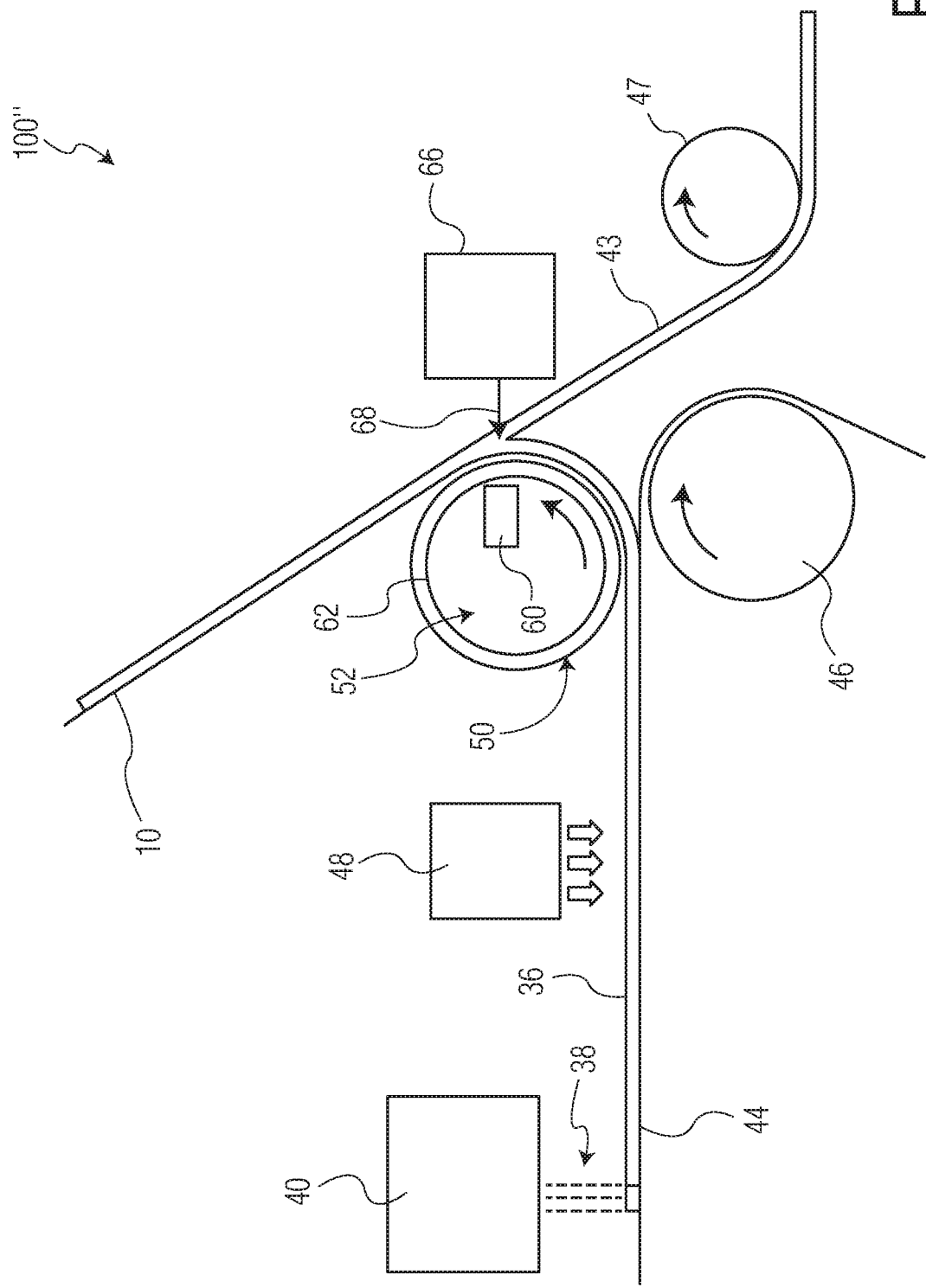
FIG. 7B is a schematic side view of an alternative exemplary apparatus and process for manufacturing a three-dimensional nonwoven according to the present invention.

FIG. 7B provides an alternative configuration of an apparatus and method 100" for manufacturing the nonwoven material 10 as described herein. In FIG. 7B, the apparatus and method 100" can include a support web 43 that is brought into contact with the precursor web 36 prior to the fluid-entangling unit 66. By separating the precursor web 36 from the support web 43, different feeding options of the precursor web 36 and the support web 43 can be achieved. For example, the precursor web 36 can be overfed to the fluid-entangling unit 66 through sizes and speeds of drive roll 46 in comparison to the texturizing drum 52, whereas the support web 43 can be supplied to the fluid-entangling unit 66 at a match speed of the texturizing drum 52 through drive roll 47. This is further described in U.S. Pat. No. 9,474,660 invented by Kirby, Scott S. C. et al., which is incorporated herein in its entirety to the extent not contradictory herewith.

Figure 7C:
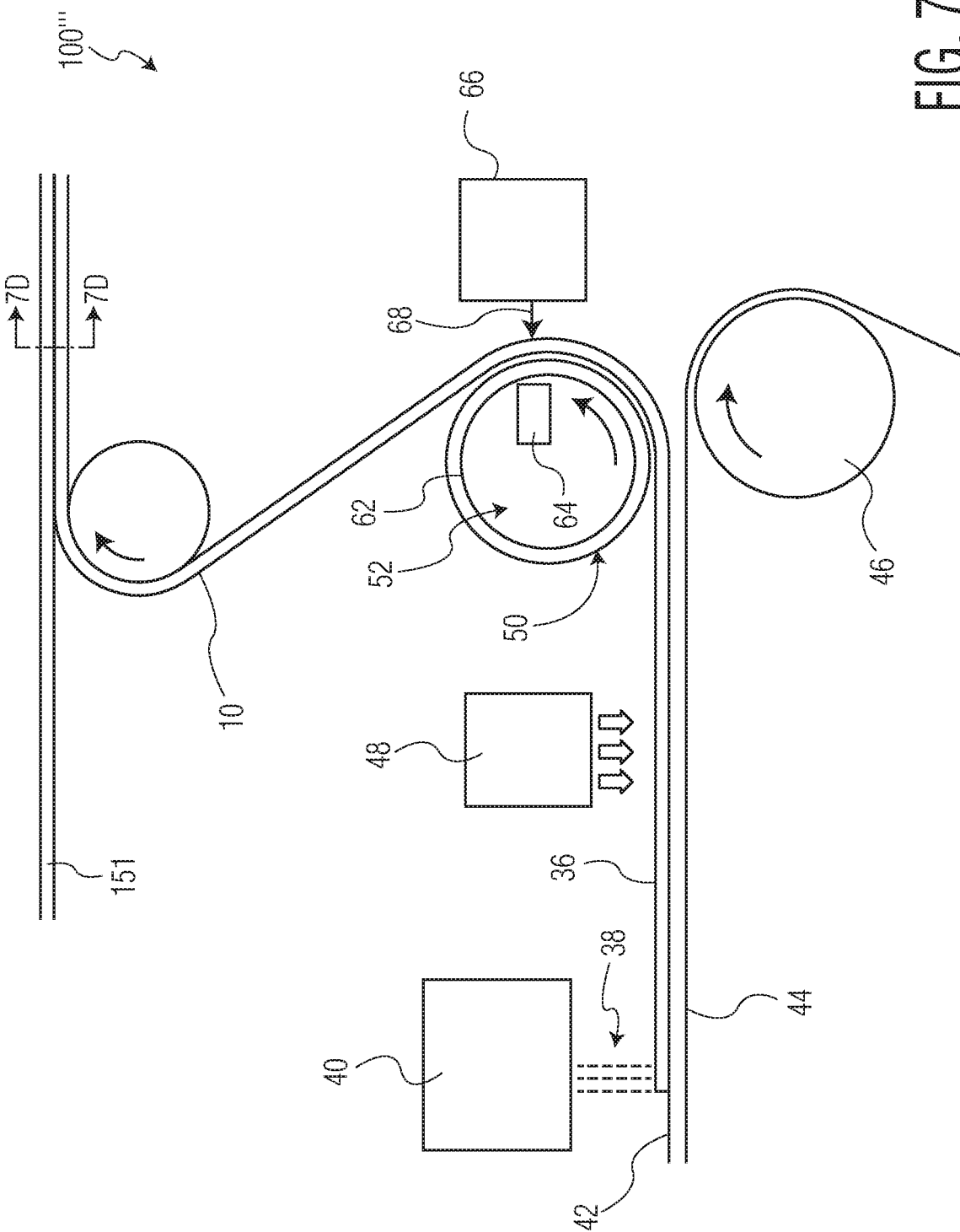
FIG. 7C is a schematics side view of yet another alternative exemplary apparatus and process for manufacturing a three-dimensional nonwoven according to the present invention.

As also depicted in FIG. 7C, in some embodiments, the nonwoven material 10 can be combined with an additional web, such as a carrier material 151. The carrier material 151 can be coupled to the nonwoven material 10 through any suitable coupling mechanism, such as by adhesive bonding or mechanical bonding, for example, ultrasonic bonding, pressure bonding, thermal bonding, or any other suitable bonding mechanism. In some preferred embodiments, the carrier material 151 is bonded to the nonwoven material 10 in the first and second side zones 26a, 26b of the nonwoven material 10, but not in the apertured zone 16 of the nonwoven material. The carrier material 151 can be coupled to the nonwoven material 10 after the fluid-entangling unit 66. In some embodiments, the carrier material 151 can be coupled to the nonwoven material 10 after the nonwoven material 10 is dried. In other embodiments, the carrier material 151 can be coupled to the nonwoven material 10 before the nonwoven material 10 is dried. The carrier material 151 can provide additional tensile strength to the nonwoven material 10 and can improve its handling in high speed converting and/or manufacturing environments. The carrier material 151 is preferably a liquid permeable material and is coupled to the nonwoven material 10 such that the carrier material 151 adjoins the first surface 20 of the nonwoven material 10 including the nodes 12, as shown best in FIG. 7D. It is also noted that a carrier material 151 could be added to the apparatus 100" and process as depicted and described with respect to FIG. 7B in which a support web 43 is supplied to the fluid entangling unit 66 separate from the precursor web 36.

Figure 7D:
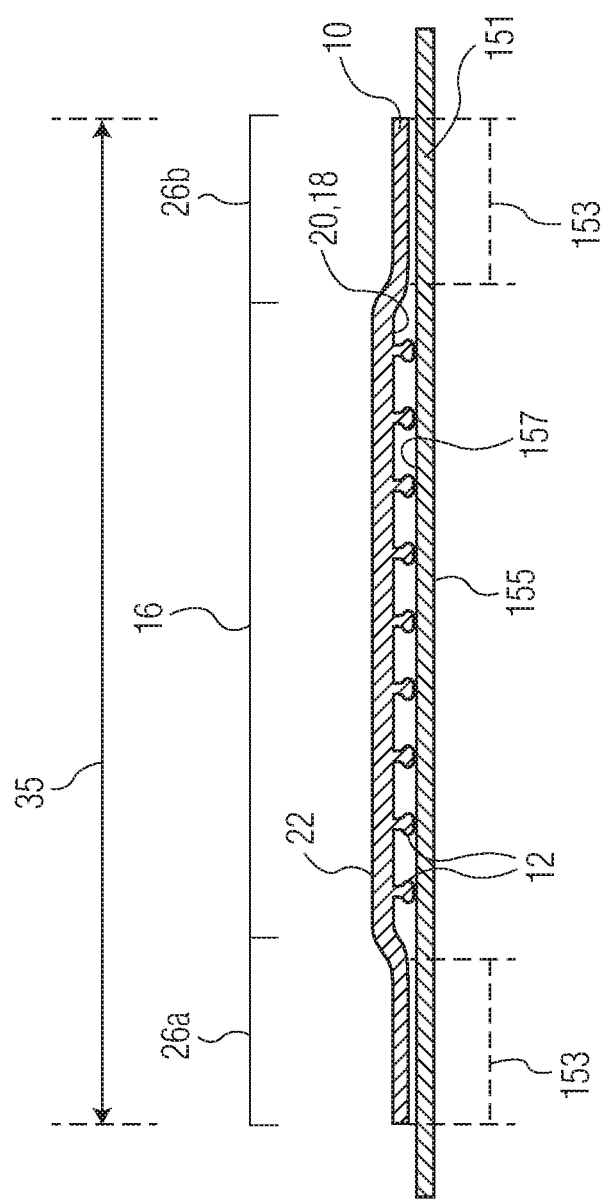
FIG. 7D is a cross-section of the nonwoven material and carrier material taken along line 7D-7D from FIG. 7C.

FIG. 7D depicts a cross-section of the nonwoven material 10 and carrier material 151 as viewed along line 7D-7D of FIG. 7C. As shown in FIG. 7D, the nonwoven material 10 coupled to the carrier material 151 can have a first surface 155 and a second surface 157. In the particular embodiment shown in FIG. 7D, the material 10 is coupled to the carrier sheet 151 in an orientation where the nodes 12 of the material 10 extend from a base plane 18 of the material 10, such as from the first surface 20, toward the second surface 157 of the carrier material 10. However, in other embodiments, other orientations of the material 10 and the carrier material 151 are contemplated.

In some embodiments, the carrier material 151 may have a width that is greater than the width 35 of the material 10, such as shown in FIG. 7D. Such configurations may be desirable where the laminate of the material 10 and the carrier material 151 is used as a liner in an absorbent article. In such embodiments, the material 10 can be localized over an absorbent body of the article, while the carrier material 151 may span fully between the edges of a chassis of the absorbent article. However, in other embodiments, the width of the carrier material 151 may be equal to the width of the material 10. Various configurations of the nonwoven material of the present disclosure, such as material 10, and the secondary material, such as carrier material 151, disposed within an absorbent article are described in more detail below with respect to FIGS. 11A-14.

The carrier material 151 can comprise any suitable nonwoven material, such as a spunbond material, a meltblown material, a spunbond-meltblown-spunbond (SMS) material, a spunlace material, or the like. The carrier material 151 may generally have a basis weight of between about 30 gsm and about 100 gsm. Combined, the carrier material 151 may provide the material 10 with increased strength to allow the material 10 to be processed in high-speed manufacturing processes. In at least some embodiments the carrier material 151 may contribute beneficially to fluid handling properties of the material 10.

The carrier material 151 may be coupled to the material 10 within bonding regions 153. In at least some embodiments, the material 10 is coupled to the carrier material 151 only within the bonding regions 153. As seen, these bonding regions 153 can be disposed within the side zones 26a, 26b of the material 10. In some embodiments the bonding regions 153 can be co-extensive with the side zones 26a, 26b. Although, in other embodiments, such as shown in FIG. 7D, the bonding regions 153 can be narrower than the side zones 26a, 26b. The material 10 and the carrier material 151 may be bonded through mechanical bonding methods such as heat bonding, ultrasonic bonding, pressure bonding, or the like. Alternatively, the material 10 and the carrier material 151 may be bonded with adhesive.

However, in other embodiments, the material 10 may be further bonded to the carrier material 151 within bonding regions 153 as well as within the apertured zone 16 of the material 10. For example, adhesive maybe applied to the carrier material 151 in regions which come into contact with the apertured zoned 16 of the material 10. In such embodiments, the nodes 12 of the material 10 may additionally be bonded to the carrier sheet 151 along with at least portions of the side zones 26a, 26b.

Although FIGS. 7A-7C display exemplary apparatuses 100', 100", and 100'" and methods of fluid entanglement for manufacturing the nonwoven material 10, it is contemplated that variances from these apparatuses 100', 100", and 100' and fluid entanglement processes can be used. For example, as mentioned previously, the precursor web 36 can be provided utilizing various techniques other than a wet-laying process, such as being formed by a foam-laying process or a carding process. Additionally, the precursor web 36 can be provided on a separate line and wound onto core rolls (not shown) and then transported to a separate manufacturing line to engage in the fluid entanglement process by a fluid entangling device 66 as discussed above.

Figure 9:
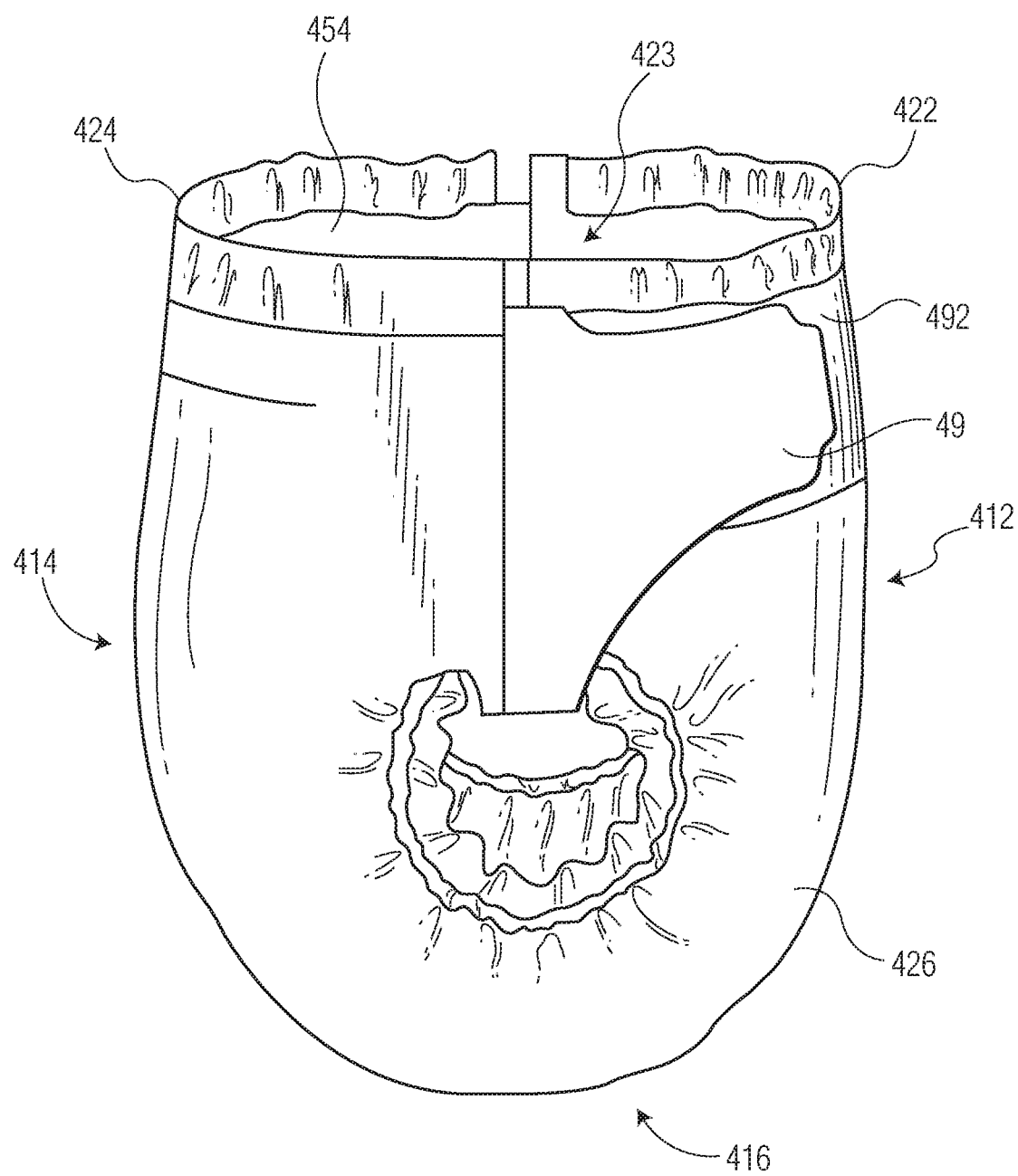
FIG. 9 is a perspective side view of an embodiment of an absorbent article including a three-dimensional nonwoven material according to the present invention.
Figure 10:
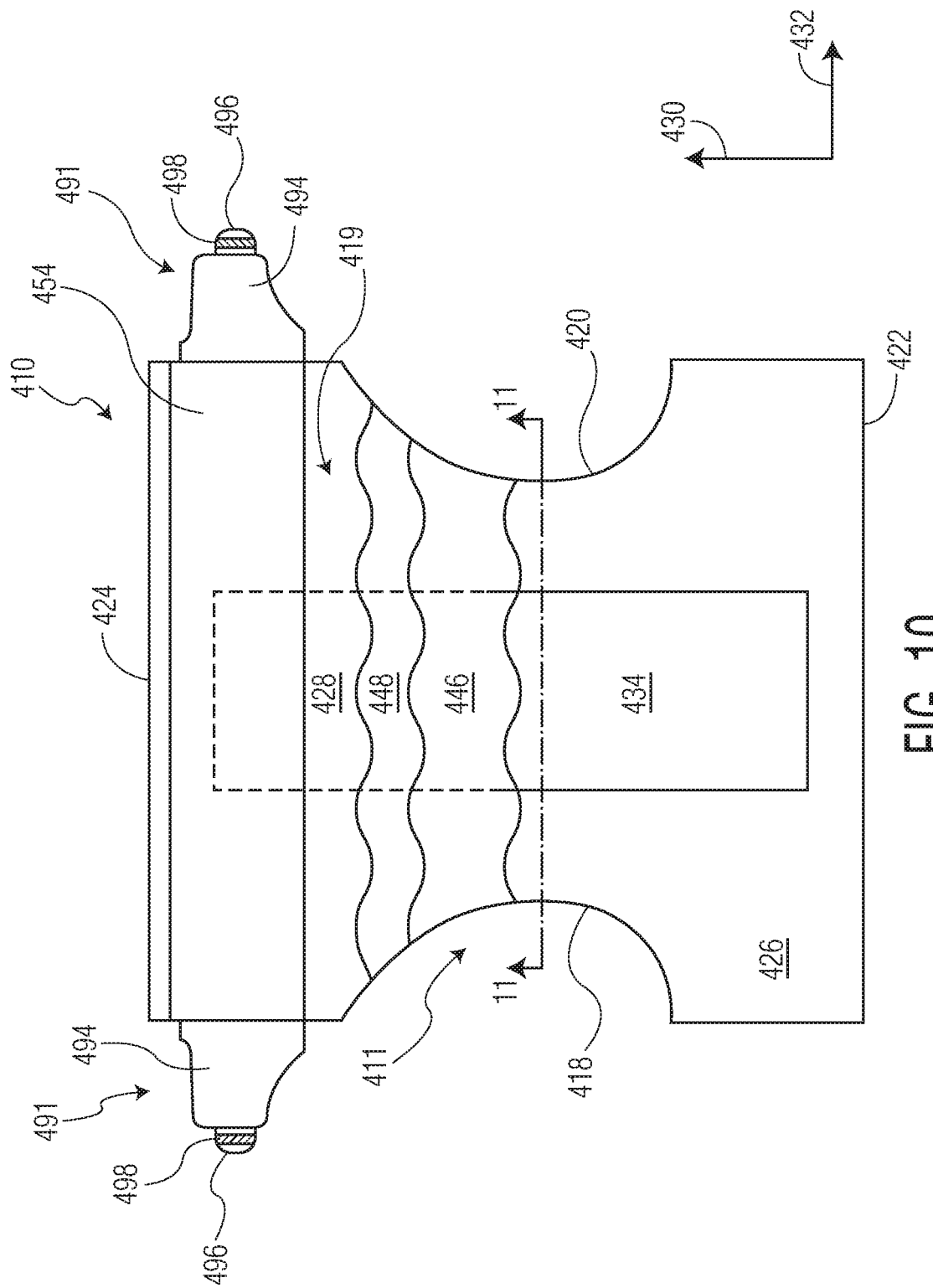
FIG. 10 is a top plan view of the absorbent article of FIG. 9 with portions cut away for clarity.

Absorbent Article:

In one of its many potential uses, the nonwoven material 10 as described above may be incorporated into an absorbent article 410. Referring to FIGS. 9-11, a non-limiting illustration of an absorbent article 410, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The nonwoven material 10 of the present disclosure can form one or more components, or one or more portions of components, of the absorbent article 410 as described below. In the exemplary embodiment described below and illustrated in FIGS. 9-11, the nonwoven material 10 can form the bodyside liner 428 of the absorbent article 410. However, as stated above, it is contemplated that the nonwoven material 10 can additionally or alternatively form other components, or other portions of components of the absorbent article 410, including, but not limited to, the outer cover 426, a fluid transfer layer 446, a fluid acquisition layer 448, a waist containment member 454, and/or a component of the fastening system, such as a front fastener 492.

The absorbent article 410 illustrated in FIG. 9 can include a chassis 11. The absorbent article 410 can include a front waist region 412, a rear waist region 414, and a crotch region 416 disposed between the front waist region 412 and the rear waist region 414 and interconnecting the front and rear waist regions, 412, 414, respectively. The front waist region 412 can be referred to as the front end region, the rear waist region 414 can be referred to as the rear end region, and the crotch region 416 can be referred to as the intermediate region.

As illustrated in FIGS. 9 and 10, the absorbent article 410 can have a pair of longitudinal side edges 418, 420, and a pair of opposite waist edges, respectively designated front waist edge 422 and rear waist edge 424. The front waist region 412 can be contiguous with the front waist edge 422 and the rear waist region 414 can be contiguous with the rear waist edge 424. The longitudinal side edges 418, 420 can extend from the front waist edge 422 to the rear waist edge 424. The longitudinal side edges 418, 420 can have portions that are curved between the front waist edge 422 and the rear waist edge 424 as depicted in FIG. 10, while in other embodiments may be configured to extend in a direction parallel to the longitudinal direction 430 for their entire length.

The front waist region 412 can include the portion of the absorbent article 410 that, when worn, is positioned at least in part on the front of the wearer while the rear waist region 414 can include the portion of the absorbent article 410 that, when worn, is positioned at least in part on the back of the wearer. The crotch region 416 of the absorbent article 410 can include the portion of the absorbent article 410 that, when worn, is positioned between the legs of the wearer and can partially cover the lower torso of the wearer. The waist edges, 422 and 424, of the absorbent article 410 are configured to encircle the waist of the wearer and together define a central waist opening 423 (as labeled in FIG. 9) for the waist of the wearer. Portions of the longitudinal side edges 418, 420 in the crotch region 416 can generally define leg openings for the legs of the wearer when the absorbent article 410 is worn.

The absorbent article 410 can include an outer cover 426 and a bodyside liner 428. The outer cover 426 and the bodyside liner 428 can form a portion of the chassis 411. In an embodiment, the bodyside liner 428 can be bonded to the outer cover 426 in a superposed relation by any suitable means such as, but not limited to, adhesives, ultrasonic bonds, thermal bonds, pressure bonds, or other conventional techniques. The outer cover 426 can define a length in a longitudinal direction 430, and a width in the lateral direction 432, which, in the illustrated embodiment, can coincide with the length and width of the absorbent article 410.

The chassis 411 can include an absorbent body 434. The absorbent body 434 can be disposed between the outer cover 426 and the bodyside liner 428. In an embodiment, the absorbent body 434 can have a length and width that are the same as or less than the length and width of the absorbent article 410. The bodyside liner 428, the outer cover 426, and the absorbent body 434 can form part of an absorbent assembly 444. The absorbent assembly 444 can also include a fluid transfer layer 446 (shown in FIGS. 10 and 11) and a fluid acquisition layer 448 (shown in FIGS. 10 and 11) between the bodyside liner 428 and the absorbent body 434. In some embodiments, if a fluid transfer layer 446 is present, the acquisition layer 448 can be between the bodyside liner 428 and the fluid transfer layer 446 as is known in the art. The absorbent assembly 444 can also include a spacer layer (not shown) disposed between the absorbent body 434 and the outer cover 426 as is known in the art. The absorbent assembly 444 can include other components in some embodiments. It is also contemplated that some embodiments may not include a fluid transfer layer 446, and/or an acquisition layer 448, and/or a spacer layer.

The absorbent article 10 can be configured to contain and/or absorb liquid, solid, and semi-solid body exudates discharged from the wearer. In some embodiments, a pair of containment flaps (not shown) can be configured to provide a barrier to the lateral flow of body exudates. In some embodiments, the absorbent article 410 can further include leg elastic members (not shown) as are known to those skilled in the art. In some embodiments, the absorbent article 10 can include a waist containment member 454. The waist containment member 454 can be disposed in the rear waist region 414 of the absorbent article 410. Although not depicted herein, it is contemplated that the waist containment member 454 can be additionally or alternatively disposed in the front waist region 412 of the absorbent article 410.

Additional details regarding each of these elements of the absorbent article 10 described herein can be found below and with reference to the FIGS. 1 through 7.

Outer Cover:

The outer cover 426 and/or portions thereof can be breathable and/or liquid impermeable. The outer cover 426 and/or portions thereof can be elastic, stretchable, or non-stretchable. The outer cover 426 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 426 can be constructed of a microporous polymeric film, such as polyethylene or polypropylene.

In an embodiment, the outer cover 426 can be a single layer of a liquid impermeable material, such as a polymeric film. In an embodiment, the outer cover 426 can be suitably stretchable, and more suitably elastic, in at least the lateral direction 432 of the absorbent article 410. In an embodiment, the outer cover 26 can be stretchable, and more suitably elastic, in both the lateral 432 and the longitudinal 430 directions. In an embodiment, the outer cover 426 can be a multi-layered laminate in which at least one of the layers is liquid impermeable. In some embodiments, the outer cover 426 can be a two layer construction, which two layers can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 426 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 426 can be a 20 gsm spunbond polypropylene non-woven web. The outer layer may also be constructed of the same materials from which the bodyside liner 428 can be constructed as described herein.

The liquid impermeable inner layer of the outer cover 426 (or the liquid impermeable outer cover 426 where the outer cover 426 is of a single-layer construction) can be either vapor permeable (i.e., "breathable") or vapor impermeable. The liquid impermeable inner layer (or the liquid impermeable outer cover 426 where the outer cover 426 is of a single-layer construction) can be manufactured from a thin plastic film. The liquid impermeable inner layer (or the liquid impermeable outer cover 426 where the outer cover 426 is of a single-layer construction) can inhibit liquid body exudates from leaking out of the absorbent article 410 and wetting articles, such as bed sheets and clothing, as well as the wearer and caregiver.

In some embodiments, where the outer cover 426 is of a single layer construction, it can be embossed and/or matte finished to provide a more cloth-like texture or appearance. The outer cover 426 can permit vapors to escape from the absorbent article 410 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 434 can be suitably constructed to be generally compressible, conformable, pliable, non-irritating to the wearer's skin and capable of absorbing and retaining liquid body exudates. The absorbent body 434 can be manufactured in a wide variety of sizes and shapes (for example, rectangular, trapezoidal, T-shape, I-shape, hourglass shape, etc.) and from a wide variety of materials. The size and the absorbent capacity of the absorbent body 434 should be compatible with the size of the intended wearer (infants to adults) and the liquid loading imparted by the intended use of the absorbent article 410. The absorbent body 434 can have a length and width that can be less than or equal to the length and width of the absorbent article 410.

The absorbent body 434 includes absorbent material. In an embodiment, the absorbent body 434 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 434 can be a matrix of cellulosic fluff and superabsorbent material. In an embodiment, the absorbent body 434 may be constructed of a single layer of materials, or in the alternative, may be constructed of two or more layers of materials.

Various types of wettable, hydrophilic fibers can be used in the absorbent body 434. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 434 can be free of superabsorbent material.

If a spacer layer is present, the absorbent body 434 can be disposed on the spacer layer and superposed over the outer cover 426. The spacer layer can be bonded to the outer cover 426, for example, by adhesive. In some embodiments, a spacer layer may not be present and the absorbent body 434 can directly contact the outer cover 426 and can be directly bonded to the outer cover 426. However, it is to be understood that the absorbent body 434 may be in contact with, and not bonded with, the outer cover 426 and remain within the scope of this disclosure. In an embodiment, the outer cover 426 can be composed of a single layer and the absorbent body 434 can be in contact with the singer layer of the outer cover 426. In some embodiments, at least a portion of a layer, such as but not limited to, a fluid transfer layer 446 and/or a spacer layer, can be positioned between the absorbent body 434 and the outer cover 426. The absorbent body 434 can be bonded to the fluid transfer layer 446 and/or the spacer layer.

Bodyside Liner:

The bodyside liner 428 of the absorbent article 410 can overlay the absorbent body 434 and the outer cover 426 and can be configured to receive insults of exudates from the wearer and can isolate the wearer's skin from liquid waste retained by the absorbent body 434. The bodyside liner 428 can from at least a part of the body facing surface 419 of the chassis 411 configured to be against a wearer's skin.

In various embodiments, a fluid transfer layer 446 can be positioned between the bodyside liner 428 and the absorbent body 434 (as shown in FIG. 11). In various embodiments, an acquisition layer 448 can be positioned between the bodyside liner 428 and the absorbent body 434 or a fluid transfer layer 446, if present (as shown in FIG. 11). In various embodiments, the bodyside liner 428 can be bonded to the acquisition layer 448, or to the fluid transfer layer 446 if no acquisition layer 448 is present, via adhesive and/or by a point fusion bonding. The point fusion bonding may be selected from ultrasonic, thermal, pressure bonding, and combinations thereof.

In an embodiment, the bodyside liner 428 can extend beyond the absorbent body 434 and/or a fluid transfer layer 446, if present, and/or an acquisition layer 448, if present, and/or a spacer layer, if present, to overlay a portion of the outer cover 426 and can be bonded thereto by any method deemed suitable, such as, for example, by being bonded thereto by adhesive, to substantially enclose the absorbent body 434 between the outer cover 426 and the bodyside liner 428. In some embodiments, the bodyside liner 428 and the outer cover 426 may be of the same dimensions in width and length. In some embodiments, however, the bodyside liner 428 may be narrower than the outer cover 426 and/or shorter than the outer cover 426. In some embodiments, the length of the bodyside liner 428 can range from 50%-100% of the length of the absorbent article 410 as measured in a direction parallel to the longitudinal direction 430. In some embodiments, the bodyside liner 428 can be of greater width than the outer cover 426. It is also contemplated that the bodyside liner 428 may not extend beyond the absorbent body 434 and/or may not be secured to the outer cover 426. In some embodiments, the bodyside liner 428 can wrap at least a portion of the absorbent body 434, including wrapping around both longitudinal edges of the absorbent body 434, and/or one or more of the end edges of the absorbent body 434. It is further contemplated that the bodyside liner 428 may be composed of more than one segment of material.

The bodyside liner 428 can be of different shapes, including rectangular, hourglass, or any other shape. The bodyside liner 428 can be suitably compliant, soft feeling, and non-irritating to the wearer's skin and can be the same as or less hydrophilic than the absorbent body 434 to permit body exudates to readily penetrate through to the absorbent body 434 and provide a relatively dry surface to the wearer.

The bodyside liner 428 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 428. The bodyside liner 428 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 428 need not be a unitary layer structure, and thus, can include more than one layer of fabrics, films, and/or webs, as well as combinations thereof. For example, the bodyside liner 428 can include a support layer and a projection layer that can be hydroentangled. The projection layer can include hollow projections, such as those disclosed in U.S. Pat. No. 9,474,660 invented by Kirby, Scott S. C. et al., and as depicted in FIG. 8.

For example, the bodyside liner 428 can be composed of a meltblown or spunbond web of polyolefin fibers. Alternatively, the bodyside liner 428 can be a bonded-carded web composed of natural and/or synthetic fibers. The bodyside liner 428 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 428 or it can be selectively applied to particular sections of the bodyside liner 428.

In an embodiment, a bodyside liner 428 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 428 can be a spunbond substrate with a basis weight from about 10 or 12 to about 15 or 20 gsm. In an embodiment, a bodyside liner 428 can be a 12 gsm spunbond-meltblown-spunbond substrate having 10% meltblown content applied between the two spunbond layers.

Although the outer cover 426 and bodyside liner 428 can include elastomeric materials, it is contemplated that the outer cover 426 and the bodyside liner 428 can be composed of materials which are generally non-elastomeric. In an embodiment, the bodyside liner 428 can be stretchable, and more suitably elastic. In an embodiment, the bodyside liner 428 can be suitably stretchable and more suitably elastic in at least the lateral or circumferential direction of the absorbent article 410. In other aspects, the bodyside liner 428 can be stretchable, and more suitably elastic, in both the lateral and the longitudinal directions 432, 430, respectively.

In the exemplary embodiment depicted in FIGS. 9-11B, the hydroentangled nonwoven material 10 described above can be used for the bodyside liner 428. As illustrated in FIG. 11A, the nonwoven material 10 of the present disclosure can be oriented such that the plurality of nodes 12 extend from the base plane 18 on the first surface 20 towards the absorbent body 434. In other words, the second surface 22 of the nonwoven material 10 can form at least a portion of the body facing surface 419 of the chassis 411 configured to be against a wearer's skin. The apertured zone 16 of the nonwoven material 10 can be configured to allow exudates to flow through the plurality of openings 24 in the nonwoven material 10 to lower-laying structures of the absorbent assembly 444, such as the fluid acquisition layer 448, the fluid transfer layer 446 and the absorbent body 434.

By having nonwoven material 10 configured such that the nodes 12 extend toward the absorbent body 434, the nodes 12 can help provide additional void volume for exudates to be contained while they are being acquired and transferred to and throughout the absorbent assembly 444, yet remain away from the body facing surface 419 of the chassis 411 of the absorbent article 410. In such an orientation, the nonwoven material 10 can create void volume for exudates between the nonwoven material 10 and any lower structures in the absorbent article 10 due to nodes 12 of the nonwoven material 10 creating space between the base plane 18 of the first surface 20 and any such lower structure. The void volume for exudates created by the nonwoven material 10 can vary based on the height of the nodes 12, the node 12 density, and the area of the apertured zone 16 of the nonwoven material 10 and can be designed to adequately suit various step sizes of absorbent articles 410 and absorbent articles 410 designed for handling different exudates. By creating void volume of this nature, the nonwoven material 10 can intake exudates with minimal spreading of exudates on the body facing surface 419 of the chassis 411 of the absorbent article 410. In doing so, the nonwoven material 10 can help reduce the area of contact of exudates against a wearer's skin, reducing potential for irritation of a wearer's skin.

Figure 11A:
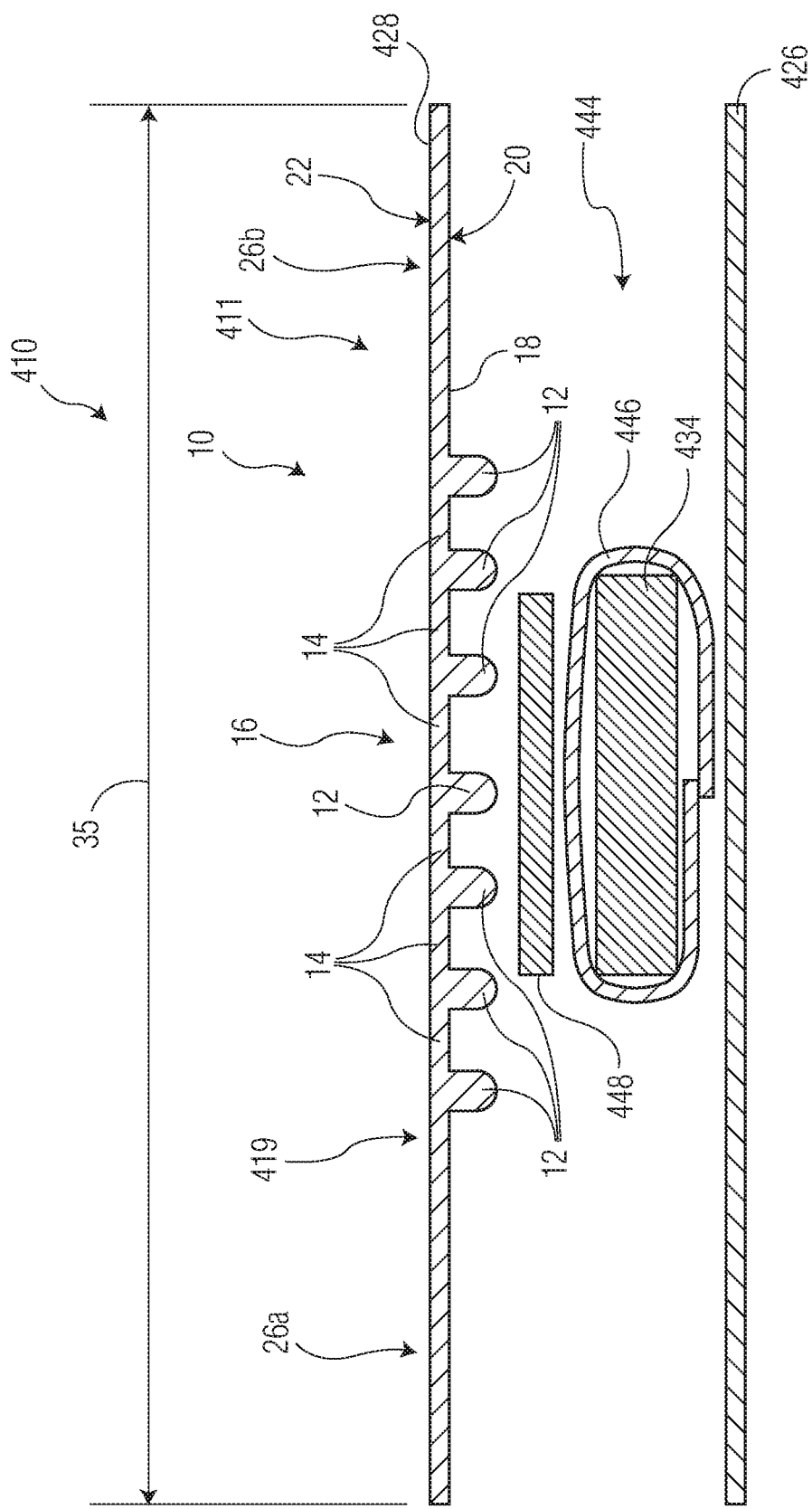
FIG. 11A is a cross-section view from FIG. 10 taken along line 11-11.

FIG. 11A depicts the nonwoven material 10 forming a bodyside liner 428 for the absorbent article 410. In such a configuration, the nonwoven material 10 can have a width that is substantially similar to a width of the outer cover 426. The second surface 22 of the nonwoven material 10 can form a body-facing surface 419 for the absorbent article 410 and can be configured to contact a wearer's skin.

Figure 11B:
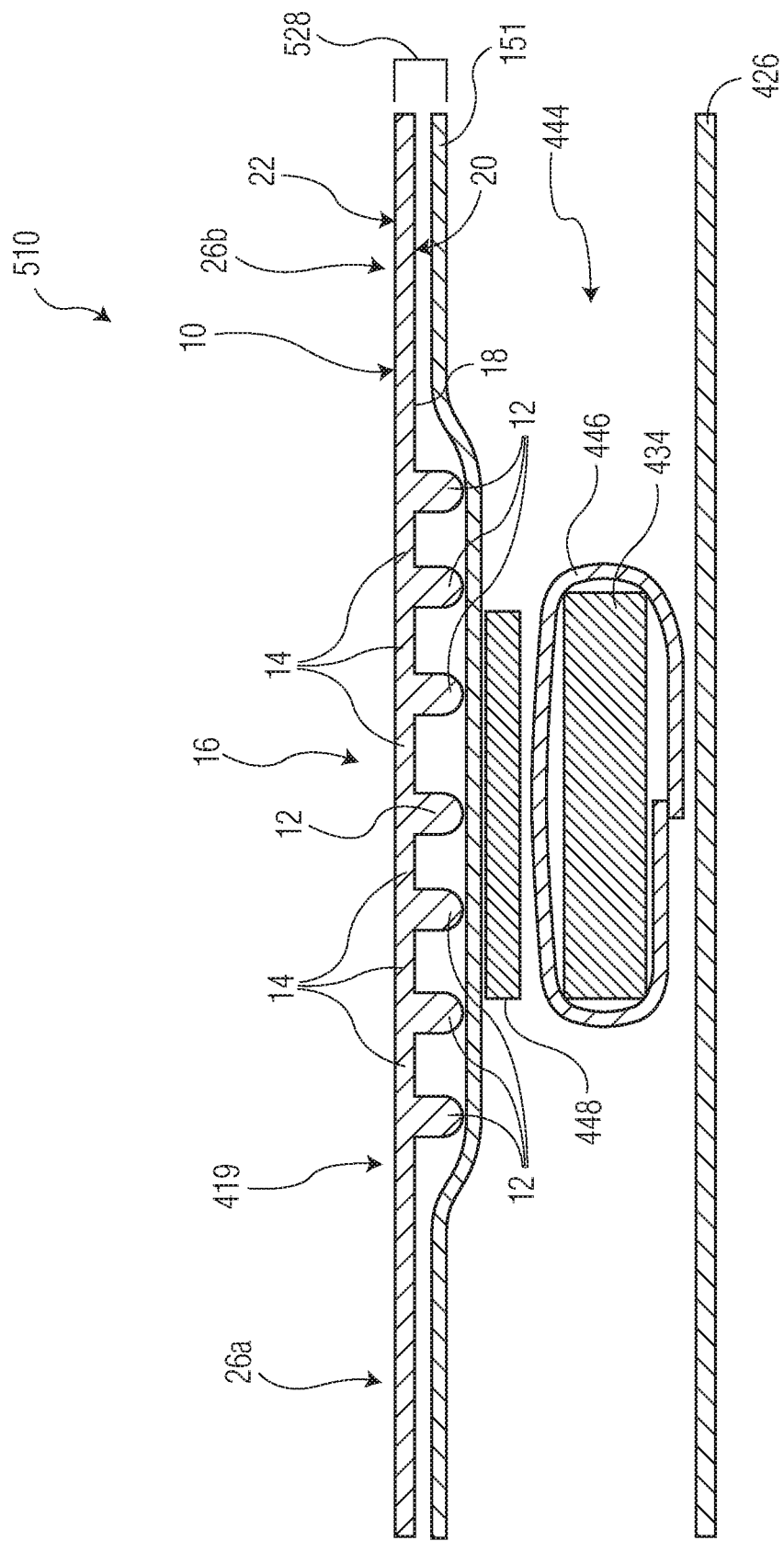
FIG. 11B is a cross-section view similar to FIG. 11A but of an alternative embodiment of an absorbent article.

FIG. 11B provides an alternative embodiment of an absorbent article 510, similar to the absorbent article 410 described in FIG. 11A unless otherwise noted herein. In FIG. 11B, the absorbent article 510 can include a nonwoven material 10 coupled to a carrier material 151 to form the bodyside liner 528. The carrier material 151 can be combined with the nonwoven material 10, for example, in process 100' described above with respect to FIG. 7C. The carrier material 151 can be coupled to the first side 20 of the nonwoven material 10. The carrier material 151 can be disposed between the nonwoven material and the absorbent body 434. In the embodiment shown in FIG. 11B, the carrier material 151 can be disposed between the nonwoven material 10 and the fluid acquisition material 448.

Figure 11C:
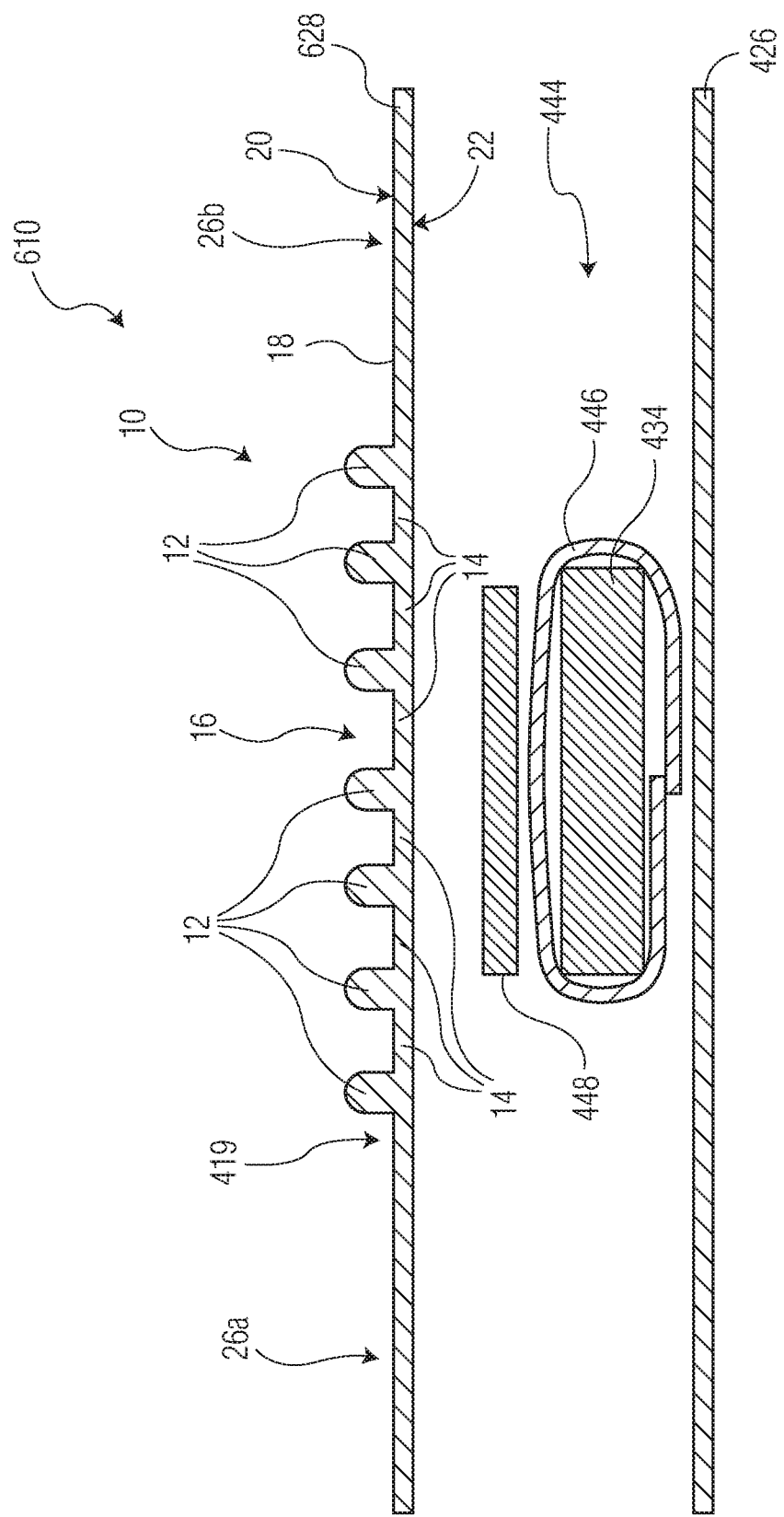
FIG. 11C is a cross-section view similar to FIGS. 11A and 11B but of yet another alternative embodiment of an absorbent article.

Other orientations and variations of the nonwoven material 10 within an absorbent article are also within the scope of this disclosure. For example, while the nonwoven material 10 is shown in FIGS. 11A and 11B as being oriented with the nodes 12 extending from the base plane 18 of the first surface 20 toward the absorbent body 434, it is also contemplated that the nonwoven material 10 can be oriented such that the nodes 12 extend from the base plane 18 of the first surface 20 away from the absorbent body 434, such as illustrated in FIG. 11C. In the embodiment of the absorbent article 610 depicted in FIG. 11C, the nonwoven material 10 can form the bodyside liner 628 with the first surface 20 providing a body facing surface 419 configured to be against a wearer's skin. In such an embodiment, the nodes 12 can provide separation from body exudates that may be on the base plane 18 of the first surface 20 of the nonwoven material 10. Additionally, the nodes 12 can provide barriers to the spreading of body exudates, such as BM, on the first surface 20 of the nonwoven material 10. By reducing the spreading of exudates on the nonwoven material 10, the nonwoven material 10 can help reduce irritation of a wearer's skin and can help reduce the likelihood of exudates leaking from the absorbent article 610.

Figure 12:
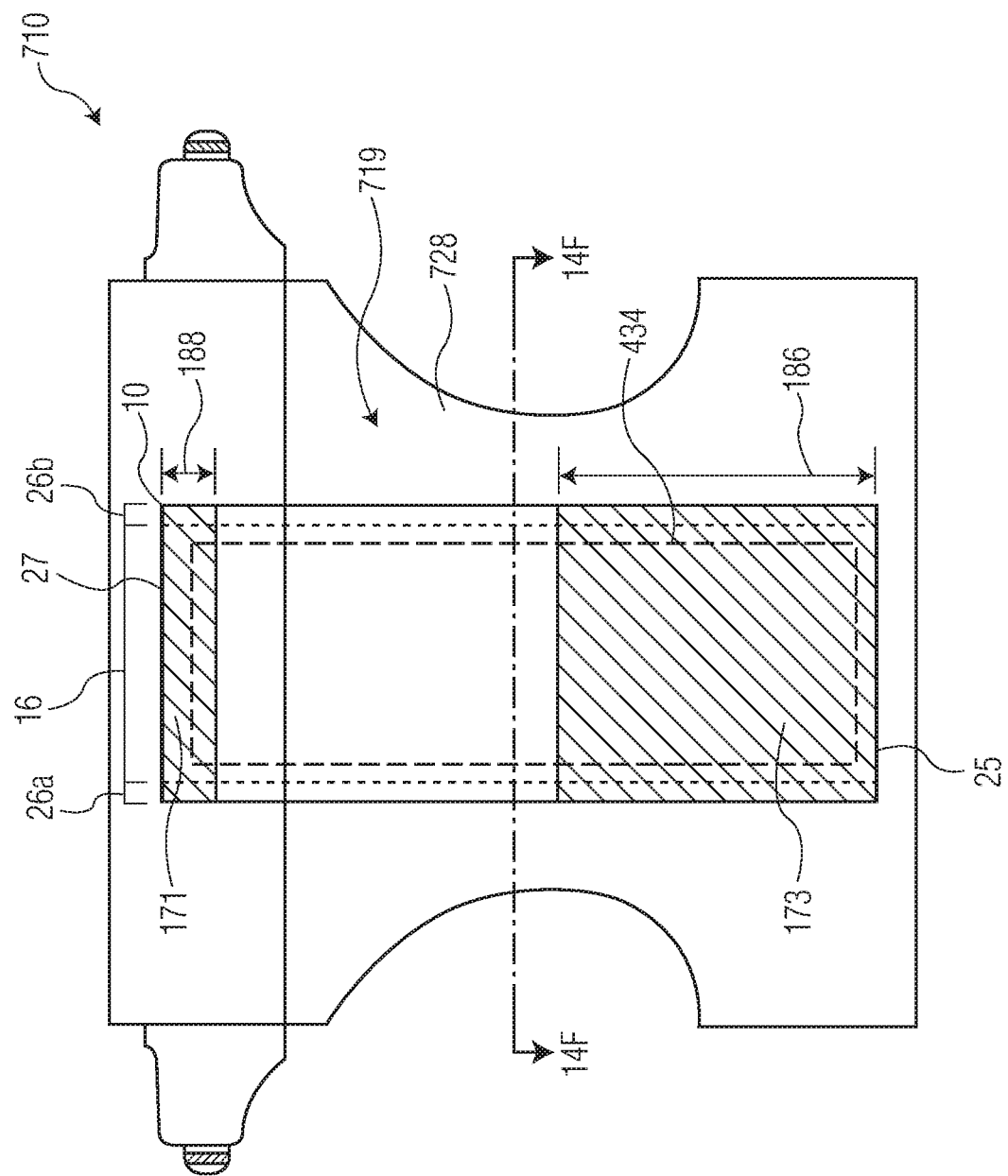
FIG. 12 is a top plan view of an alternative embodiment of the absorbent article of FIG. 9.

FIG. 12 depicts an absorbent article 710, similar to absorbent articles 410, 510, and 610. In the embodiment of FIG. 12, the article 710 may include a nonwoven material according to the present disclosure, such as material 10. As can be seen more clearly in FIG. 14, which depicts a cross-section of the article 710 as viewed along line 14F-14F of FIG. 12, the nonwoven material 10 may be disposed on top of bodyside liner 728. In some exemplary embodiments, the bodyside liner 728 may be a material such as the carrier material 151 described with respect to process 100''' of FIG. 7C.

In the embodiment of FIG. 12, the material 10 may have a width (width 35 described in FIG. 1) that is generally less than the width of the bodyside liner 728. In such embodiments, the material 10 may be positioned on the chassis 719 of the article 710 so as to be disposed generally above the absorbent body 434. In some embodiments, the apertured zone 16 of the material 10 may entirely cover the absorbent body 434. In such embodiments, the side zones 26a, 26b may be disposed completely outboard of the absorbent body 434. However, in other embodiments, the side zones 26a, 26b can at least partially overlap the absorbent body 434.

The material 10 may be bonded to the chassis 719 at least throughout a front waist bonding region 173 and throughout a rear waist bonding region 171. The front waist bonding region 173 may generally be disposed proximate the front edge 25 of the material 10. The front waist bonding region 173 also extends throughout the apertured zone 16 of the material 10 and may extend at least partially through the side zones 26 and/or 26b in some embodiments, such as shown in FIG. 12. The front waist bonding region 173 may have a length 186 that is greater than about 20% of an overall length of the material 10, or is greater than about 30%, or is greater than about 35%, or greater than about 40%, or greater than about 45%, or greater than about 50% of the overall length of the material 10. In some preferred embodiments, the length 186 may be less than about 60%, or less than about 55%, or less than about 50%, of the overall length of the material 10. In at least some embodiments, the front waist bonding region 173 may be generally formed by mechanical bonding means, for example by heat bonding, ultrasonic bonding, pressure bonding, or the like. However, in other embodiments, the front waist bonding region 173 may be formed by adhesive bonding.

The large area that the front waist bonding region 173 covers may be especially preferable where the average areas of the openings 24 of the material 10 within the apertured zone 16 are greater than about 17 mm$^2$, or more preferably where the average areas are greater than about 20 mm$^2$. With such large average areas of the openings 24, a risk of penile strangulation increases for male wearers of an article 710 including such a material 10. By bonding a large portion of a front region of the material 10 to the chassis 719, the openings 24 in the front portion of the article 710 are prevented from becoming wrapped around a penis of a male wearer.

The rear waist bonding region 171 is disposed proximate the rear edge 27 of the material 10 and bonds the material 10 to the chassis 719. Like the front waist bonding region 173, the rear waist bonding region 171 may extend throughout the apertured zone 16 of the material 10 and may further extend at least partially through the side zones 26 and/or 26b in some embodiments. The rear waist bonding region 171 may be generally formed by mechanical bonding means, for example by heat bonding, ultrasonic bonding, pressure bonding, or the like. Although, in other embodiments, the rear waist bonding region 171 may be formed by adhesive bonding.

The rear waist bonding region 171 contrasts with the front waist bonding region 173 as the rear waist bonding region 171 has a length 188 that is much smaller than the length 186 of the front waist bonding region 173. In the rear portion of the article 719, it is desired that the material 10 is generally un-adhered to the chassis 719 so that the material 10 may provide a void volume, by way of the nodes 12 facing the chassis 719, to provide enhanced intake and storage qualities for fecal matter which is generally exuded into a rear region of the article 719 proximate the rear edge 27 of the material 10. Accordingly, the length 188 is preferably less than about 10% of the overall length of the material 10, or more preferably less than about 7.5%, or less than about 5%, or less than about 2.5% of the overall length of the material 10. In some preferred embodiments, the length 188 is preferably greater than about 2% of the overall length of the material 10. The rear waist bonding region 171 generally operates to ensure that the rear edge 27 of the material 10 is adhered to the chassis 719.

Figure 13:
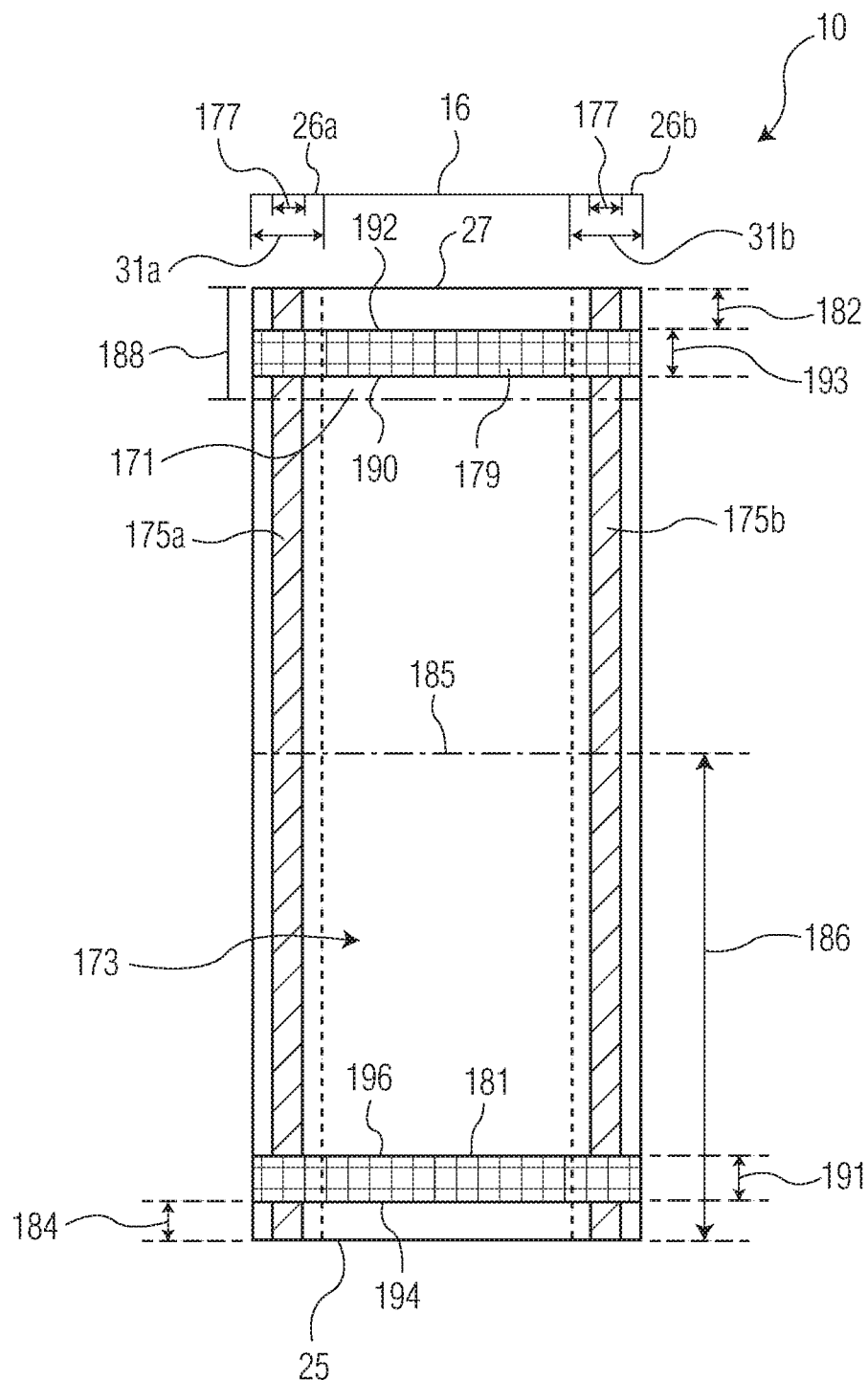
FIG. 13 is a top plan view of an exemplary nonwoven material from the absorbent article of FIG. 12 with an exemplary bonding configuration depicted with respect to the nonwoven material.
Figure 14:
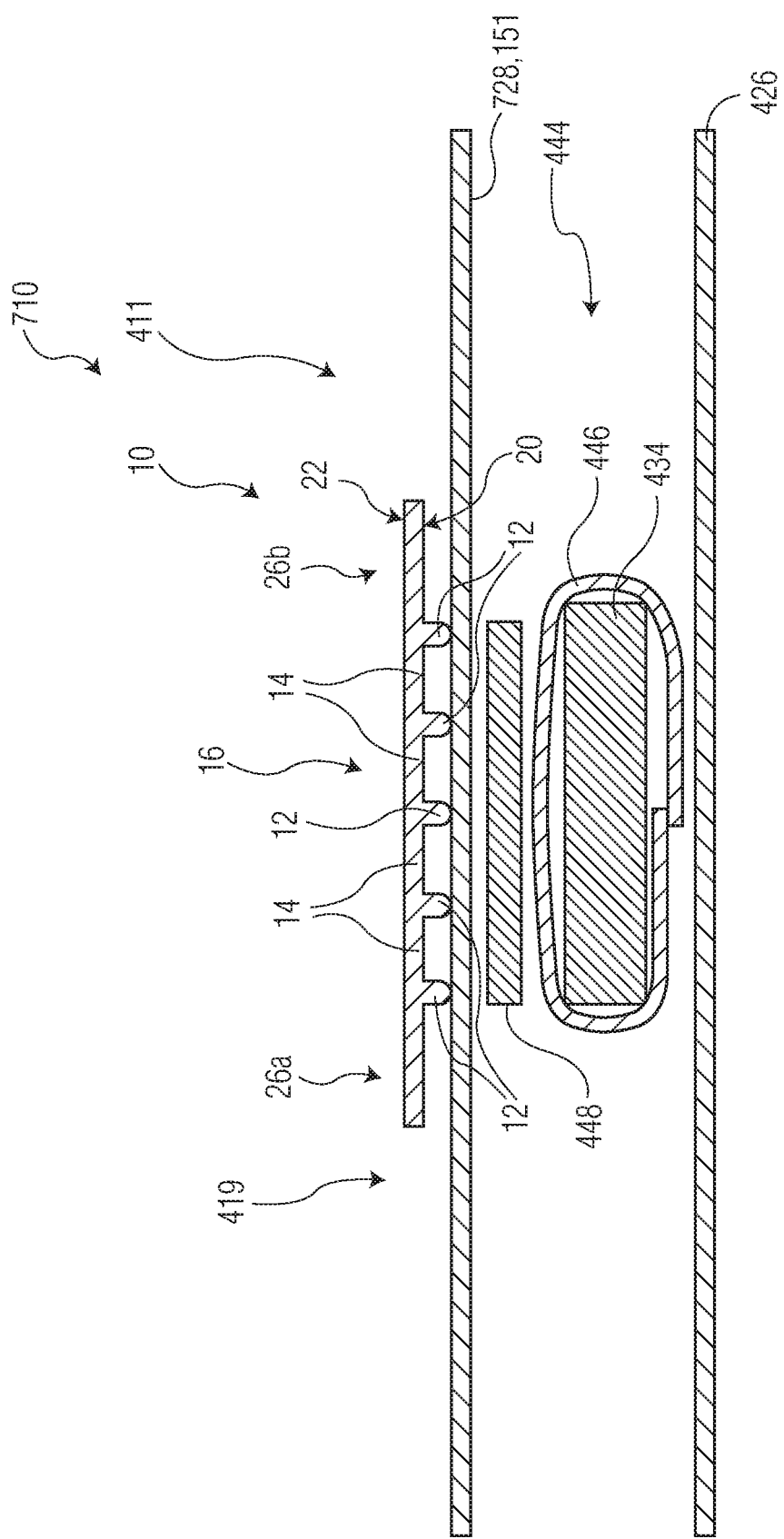
FIG. 14 is a cross-section view from FIG. 12 taken along line 14F-14F.

FIG. 13 depicts the material 10 in isolation from the article 710 and further illustrates an exemplary bonding configuration which may be used to bond the material 10 to the chassis 719 of the absorbent article 710. As shown in FIG. 13, in addition to the boning regions 171, 173 (both regions 171 and 173 are shown in FIG. 13 without shading to more clearly illustrate other features within FIG. 13), the material 10 may be further bonded to the bodyside liner 728 within the side zones 26a, 26b by adhesive bonds 175a, 175b.

In some manufacturing processes of forming the article 710 including the material 10, adhesive may be applied to the bodyside liner 728 before the material 10 is brought to the liner 728 to form the bonds 175a, 175. Accordingly, in such embodiments it may be important for the adhesive bonds 175a, 175b to have widths 177 which are generally smaller than the widths 31a, 31b of the side zones 26a, 26b of the material 10. According to some embodiments, the widths 177 may be between about 50% and about 90%, or between about 60% and about 80% of the widths 31a, 31b of the side zones 26a, 26b. Although shown as extending for the full length of the material 10, the adhesive bonds 175a, 175b can extend for only between about 80% and about 97.5%, or between about 85% and about 95% of the overall length of the material 10.

The width 177 being smaller than the widths 31a, 31b allows for some inaccuracy in a desired placement of the material 10 as it is brought to bond with the liner 728 with respect to the alignment of the side zones 26a, 26b and the adhesive applied to the liner 728 which forms the bonds 175a, 175b. If the widths 177 are too great, normal process variations can cause a large enough misalignment of the material 10 with respect to the liner 728 to cause the adhesive used to form the bonds 175a, 175b applied to the liner 728 to overlap with the apertured zone 16 of the material 10 or be uncovered by the side zones 26a and/or 26b of the material 10. Such an overlap or uncovered exposure of this adhesive can result in the adhesive being exposed, through the openings 24 or otherwise, which can further result in such adhesive undesirably bonding to portions of the article 710 other than the material 10.

It is also important to balance the adhesive add-on amount of the adhesive forming the bonds 175a, 175b to ensure adequate lamination strength between the material 10 and the liner 728 but also not have adhesive bleed-through due to the relatively open nature of the side zones 26a, 26b. It has been found that adhesive add-on amounts used to form the adhesive bonds 175a, 175b should be greater than about 6.0 gsm, or greater than about 6.5 gsm, and less than about 13 gsm, or less than about 12 gsm. These ranges of adhesive add-on amounts have been found to ensure sufficient lamination strength between the material 10 and the liner 728 such that the material 10 does not delaminate from the liner 728 during manufacture or in use and that adhesive bleed-through does not occur in the side zones 26a, 26b.

In some particular embodiments, the material 10 may be coupled to the liner 728 at least through adhesive bonds 175a, 175b before the front and/or rear waist bonding regions 173, 171 are formed. For example, the material 10 may be adhesively bonded to the liner 728 by bonds 175a, 175b prior to the laminate of materials 10 and 728 being bonded together throughout bonding regions 171, 173. This may be the case where the bonding regions 171, 173 are formed by mechanical bonds.

In at least some of these embodiments, one or more additional bonds may need to be formed prior to the bonding regions 171, 173 being formed. As one example, where the material 10 is bonded to the liner 728 in a high-speed manufacturing process through bonds 175a, 175b prior to the bonding regions 171, 173 being formed, a leading edge 25 or 27 of the material 10 in the process direction may undesirably fold backward prior to the bonding regions 171, 173 being formed.

For these reasons, some contemplated bonding configurations which couple the material 10 to the liner 728 include at least one additional bond 179 or 181. In some embodiments, only one of bond 179 or 181 may be formed, depending on which end 25 or 27 of the material 10 is the leading end in a process direction. In other embodiments, both bonds 179 and 181 may be formed. According to some embodiments, the bonds 179 and/or 181 may be formed along with the adhesive bonds 175a, 175b, or at least prior to the forming of the bonding regions 171 and/or 173. Such additional bonds 179 and/or 181 help to ensure that the leading edge 25 or 27 of the material 10 is flat against the liner 728 as the bonding regions 171, 173 are formed, or both the rear edge and the front edge 25 and 27 in the process direction where both bonds 179 and 181 are formed.

In some embodiments, the additional bond or bonds 179 and/or 181 may be adhesive bonds. According to some embodiments, the bonds 179 and/or 181 may at least partially overlap the respective front waist or rear waist bonding regions 173, 171. In further embodiments, the bonds 179 and/or 181 may completely overlap the front waist and/or rear waist bonding regions 173, 171.

Where the bonds 179 and/or 181 are present, the bonds 179 and/or 181 may have front and rear edges 190, 192 and 194, 196, respectively. The bonds 179 and/or 181 may also have lengths 193 and 191, respectively. In general, the bond 179 or 181 may primarily operate to tack the leading edge 25 or 27 in the process direction to the liner 728 to allow for the bonding region 171 of 173 to be successfully formed. Although where both bonds 179 and 181 are present, the bonds 179, 181 may operate to tack both the leading and trailing edges of the material 10 in the process direction, e.g. edges 25 and 27, to the liner 27 prior to the bonding regions 171, 173 being formed. Accordingly, the lengths 191, 193 can be relatively short. According to some embodiments, the lengths 191 and/or 193 may be between about 1.0 mm and about 5.0 mm, or between about 2.0 mm and about 5.0 mm, or between about 3.0 mm and about 5.0 mm. Such relatively short lengths 191 and/or 193 may be particularly beneficial where the bonds 179 and/or 181 are adhesive bonds.

Where the bonds 179 and/or 181 are adhesive bonds, the rear and/or front edges 192, 194 of the bonds 179, 181, respectively, may be positioned distances 182, 184, respectively, from the rear edge 27 and the front edge 25 of the material 10, as shown in FIG. 13. Although it may be desirable for the distances 182 and/or 184 to be as small as possible, the distances 182 and/or 184 may generally be between about 2.0 mm and about 5.0 mm, or between about 2.5 mm and about 5.0 mm, or between about 2.5 mm and about 4.0 mm. Where the bonds 179 and/or 181 are adhesive bonds, such offsets from the rear and front edges 27, 25 of the material 10 helps to ensure that normal alignment variations within a high-speed absorbent article manufacturing process do not result in the adhesive forming the bonds 179 and/or 181 becoming undesirably exposed beyond the edges 25 and/or 27 of the material 10.

As shown in FIG. 13, the bonds 179, 181 extend through the apertured zone 16 of the material 10. Where the bonds 179, 181 are adhesive bonds, it is important for the add-on amounts of the adhesive to be relatively low in order to prevent adhesive from bleeding through the openings 24 of the apertured zone 16. Such adhesive bleed-through can cause undesired bonding between portions of the article 710. It has been found that the adhesive add-on amount for the adhesive bonds 179 and/or 181 should be between about 10 gsm and about 40 gsm, or between about 10 gsm and about 35 gsm, or between about 15 gsm and about 35 gsm.

Although, in embodiments where both the bonds 179, 181 are formed, the bond 179 or 181 which bonds the leading edge 25 or 27 of the material 10 in the manufacturing process to the liner 728 may have a higher add-on amount than the other of the bonds 179, 181. For instance, the leading edge 25 or 27 of the material 10 is subjected to higher forces in a high speed manufacturing process than the trailing edge 25 or 27. Accordingly, the bond 179, 181 which bonds the leading edge 25 or 27 to the liner 728 may need to be relatively stronger than the bond 179, 181 which bonds the trailing edge 25 or 27 to the liner 728. In these embodiments, the bond 179 or 181 which bonds the leading edge 25 or 27 to the liner 728 may have an add-on amount of between about 15 gsm and about 40 gsm, or between about 25 gsm about 35 gsm. In contrast, the other of the bonds 179, 181 which bod the trialing edge 25 or 27 of the material 10 to the liner 728 may have an add-on amount that is greater than about 5 gsm but less than about 15 gsm.

Other contemplated bonding configurations may include a configuration comprising bonds 173, 175a, and 175b along with just bonding region 173 or with just bond 179. Further contemplated bonding configurations may include a configuration comprising bonds 175a and 175b along with bonding region 173 and just bond 181. Still further contemplated bonding configurations may include a configuration comprising bonds 175a and 175b along with both bonds 179 and 181, but without bonding regions 171, 173.

Waist Containment Member:

In an embodiment, the absorbent article 410 can have one or more waist containment members 454. FIGS. 9 and 10 illustrate a preferred embodiment of a waist containment member 454 on an absorbent article 410, such as a diaper where the waist containment member 454 can be disposed in the rear waist region 414. In some embodiments, the waist containment member 454 can be disposed in the front waist region 412. The waist containment member 454 can be disposed on the body facing surface 419 of the chassis 411. The waist containment member 454 can be coupled to the chassis 411 such that a portion of the waist containment member 454 is free to move with respect to the chassis 411 and can form a pocket to help contain body exudates.

The waist containment member 454 can be comprised of a variety of materials. In a preferred embodiment, the waist containment member 454 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 454 can be comprised of a laminate of more than one of these exemplary materials, or other materials. In some embodiments, the waist containment member 454 can be comprised of a liquid impermeable material. In some embodiments, the waist containment member 454 can be comprised of a material coated with a hydrophobic coating. In some embodiments, the waist containment member 54 can include an elastic material to provide additional fit and containment properties to the absorbent article 10. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist containment member 454 may be omitted from the absorbent article 410 without departing from the scope of this disclosure.

Fastening System:

In an embodiment, the absorbent article 410 can include a fastening system. The fastening system can include one or more back fasteners 491 and one or more front fasteners 492. The embodiments shown in FIGS. 9 and 10 depict an embodiment with one front fastener 492. Portions of the fastening system may be included in the front waist region 412, rear waist region 414, or both.

The fastening system can be configured to secure the absorbent article 410 about the waist of the wearer in a fastened condition as shown in FIG. 9 and help maintain the absorbent article 410 in place during use. In an embodiment, the back fasteners 491 can include one or more materials bonded together to form a composite ear as is known in the art. For example, the composite fastener may be composed of a stretch component 494, a nonwoven carrier or hook base 496, and a fastening component 498, as labeled in FIG. 10.

Test Methods

Node Analysis Test Method

The anisotropy of fibers in the nodes 12 can be determined by using the image analysis measurement method described herein. This test method can also measure node height as well as the percentage of fibers and voids within a node 12.

In this context, fiber anisotropy is considered for a plurality of nodes 12 from each respective material. Generally, the image analysis method determines a numeric value of anisotropy from a cross-sectional image of a node 12 via a specific image analysis measurement parameter named anisotropy. The anisotropy of a node 12 can be measured by using x-ray Micro-computed Tomography (a.k.a. Micro-CT) to non-destructively acquire images with subsequent image analysis techniques to detect fiber components and then measuring the anisotropy of said components within the node 12 regions only. The image analysis algorithm performs detection, image processing and measurement and also transmits data digitally to a spreadsheet database. The resulting measurement data are used to compare the anisotropy of differing structures possessing fibrous node 12 components.

The method for determining the anisotropy in each structures nodes' fibers includes the first step of acquiring digital x-ray Micro-CT images of a sample. These images are acquired using a SkyScan 1272 Micro-CT system available from Bruker microCT (2550 Kontich, Belgium). The sample is attached to a mounting apparatus, supplied by Bruker with the SkyScan 1272 system, so that it will not move under its own weight during the scanning process. The following SkyScan 1272 conditions are used during the scanning process:

Camera Pixel Size (um)=9.0
Source Voltage (kV)=35
Source Current (uA)=225
Image Pixel Size (um)=6.0
Image Format=TIFF
Depth (bits)=16
Rotation Step (deg.)=0.10
Use 360 Rotation=NO
Frame Averaging=ON (6)
Random Movement=ON (1)
Flat Field Correction=ON
Filter=No Filter After sample scanning is completed, the resulting image set is then reconstructed using the NRecon program provided with the SkyScan 1272 Micro-CT system. While reconstruction parameters can be somewhat sample dependent, and should be known to those skilled in the art, the following parameters should provide a basic guideline to an analyst:

Image File Type=JPG
Pixel Size (um)=6.00
Smoothing=1 (Gaussian)
Ring Artifact Correction=10
Beam Hardening Correction (%)=10

After reconstruction is completed, the resulting image data set is now ready for extraction of cross-sectional image slices using the Bruker SkyScan software package called DataViewer. After downloading the entire reconstructed image data set into DataViewer, the analyst, skilled in the art of Micro-CT technologies, must then select and extract cross-sectional image slices which reside at or near the center of nodes present in each respective sample. One centered node 12 should be obtained for each image selected. For a typical specimen, this process will result in 4-6 images and from which 4-6 nodes 12 will be available for analysis. The analyst should then re-number the images sequentially (e.g. 1, 2, 3, etc.) by changing the image file suffix numbers.

Once a set of cross-sectional Micro-CT images have been acquired and re-numbered from each specimen, anisotropy measurements can now be made using image analysis software.

The image analysis software platform used to perform the anisotropy measurements is a QWIN Pro (Version 3.5.1) available from Leica Microsystems, having an office in Heerbrugg, Switzerland.

Thus, the method for determining the anisotropy of a given sample includes the step of performing several anisotropy measurements on the Micro-CT image set. Specifically, an image analysis algorithm is used to read and process images as well as perform measurements using Quantimet User Interactive Programming System (QUIPS) language. The image analysis algorithm is reproduced below.

Define Variables & Open Files

```
The following line designates the computer location where data is sent to
Open File (C:\Data\94054 - Nhan (patent)\z-micro-ct data.xls, channel #1)
PauseText ("Enter the number of the final image in the set.")
Input (IMAGES)
SAMPLE ID AND SET UP
Enter Results Header
File Results Header (channel #1)
File Line (channel #1)
Measure frame (x 31, y 61, Width 1737, Height 793)
Image frame ( x 0, y 0, Width 1768, Height 854 )
    -- Calvalue 6.0 um/pixel
CALVALUE = 6.0
Calibrate (CALVALUE CALUNITS$ per pixel)
    -- Enter image prefix name of set of images to analyze
PauseText ( "Enter image file prefix name." )
Input ( TITLE$ )
File ( "Rep. #", channel #1 )
File ( "% Fiber", channel #1 )
File ( "% Voids", channel #1 )
File ( "Height (um)", channel #1 )
File ( "Anisotropy", channel #1 )
File Line ( channel #1 )
For ( REPLICATE = 1 to IMAGES, step 1 )
    Clear Accepts
    IMAGE ACQUISITION AND DETECTION
    ACQOUTPUT = 0
The following two lines indicate the computer location of the Micro-CT images to be read during the
image analysis process.
    ACQFILE$ = "C:\Images\94054 - Nhan\Z-slices\"+TITLE$+""+STR$(REPLICATE)+".jpg"
    Read image ( from file ACQFILE$ into ACQOUTPUT )
    Colour Transform ( Mono Mode )
    Grey Transform ( WSharpen from Image0 to Image1, cycles 3, operator Disc )
    Detect ( whiter than 64, from Image1 into Binary0 )
    IMAGE PROCESSING
    PauseText ( "Select region of interest for analysis." )
    Binary Edit [PAUSE] ( Accept from Binary0 to Binary1, nib Fill, width 2 )
    Binary Amend ( Close from Binary1 to Binary2, cycles 30, operator Disc, edge erode on )
    Binary Identify ( FillHoles from Binary2 to Binary3 )
    Binary Amend ( Open from Binary3 to Binary4, cycles 40, operator Disc, edge erode on )
    PauseText ( "Clean up any over extended ROI areas." )
    Binary Edit [PAUSE] ( Reject from Binary4 to Binary5, nib Fill, width 2 )
    PauseText ( "Draw vertical lline thru the thickest region binary." )
    Binary Edit [PAUSE] ( Accept from Binary5 to Binary7, nib Rect, width 2 )
    Binary Logical ( C = A AND B : C Binary6, A Binary1, B Binary5 )
        MEASURE ANALYSIS REGIONS
     -- Analysis Region Fiber Area
    MFLDIMAGE = 6
    Measure field ( plane MFLDIMAGE, into FLDRESULTS(2), statistics into FLDSTATS(7,2) )
        Selected parameters: Area, Anisotropy
    FIBERAREA = FLDRESULTS(1)
    ANISOTROPY = FLDRESULTS(2)
     -- Analysis Region Area
    MFLDIMAGE = 5
    Measure field ( plane MFLDIMAGE, into FLDRESULTS(1), statistics into FLDSTATS(7,1) )
        Selected parameters: Area
```

```
    ROIAREA = FLDRESULTS(1)
    PERCFIBER = FIBERAREA/ROIAREA*100
    PERCVOIDS = 100-PERCFIBER
      -- Measure Node Height
    Measure feature ( plane Binary7, 8 ferets, minimum area: 24, grey image: Image0 )
        Selected parameters: X FCP, Y FCP, Length
      LENGTH = Field Sum of ( PLENGTH(FTR) )
        OUTPUT DATA
      File ( REPLICATE, channel #1, 0 digits after '.' )
      File ( PERCFIBER, channel #1, 1 digit after '.' )
      File ( PERCVOIDS, channel #1, 1 digit after '.' )
      File ( LENGTH, channel #1, 1 digit after '.' )
      File ( ANISOTROPY, channel #1, 2 digits after '.' )
      File Line ( channel #1 )
  Next ( REPLICATE )
  Close File (channel #1)
  END
```

The QUIPS algorithm is executed using the QWIN Pro software platform. The analyst is initially prompted to enter the number of images in the set for a particular specimen. Next, the analyst is prompted to enter specimen identification information which is sent to the EXCEL file.

The analyst is next prompted by an interactive command window and an input window to enter the image file prefix of the Micro-CT images to be analyzed. After this step, all subsequent images for a given sample will be read automatically by the image analysis algorithm described above.

The analyst is next prompted to manually select, with the computer mouse, the node region of interest for analysis. Care should be taken to select the entire node so as to include the tapered sections just down to base plane 18 of the material.

After several steps of image processing that will occur automatically, the analyst will again be prompted to clean up any over-extended region of interest (ROI) areas. This is done using the computer mouse as well as toggling the overlying binary image on and off by simultaneously using the 'control' and 'b' keys on the computer keyboard. After this step, the binary should only be covering the node.

Lastly, the analyst will be prompted to use the computer mouse to draw a vertical line thru the tallest region of the binary image. This line will be used by the computer algorithm to measure the height of the node 12.

The process of selecting the node 12 region of interest, clean up of over-extended regions, and drawing a vertical line thru the tallest region of the node 12 will repeat until all the images for a particular specimen have been analyzed.

After all images have been analyzed, the following measurement parameter data will be located in the corresponding EXCEL file:

| |
|---|
| Replicate # |
| % Fiber |
| % Voids |
| Height |
| Anisotropy |

There will be 4-6 values listed in columns for each of these parameters. For the purposes of comparing anisotropy values between specimens, the data in the column labeled 'Anisotropy' can be compared between different specimens by performing a Student's T analysis at the 90% confidence level.

Material Sample Analysis Test Method

The Material Sample Analysis Test Method as described herein can be used for determining the percent open area in a given sample nonwoven material 10. In this context, the percent open area is considered as the percent of an area of the nonwoven material in which light transmitted from a light source passes directly through unhindered. Generally, this image analysis method determines a numeric value of percent open area for a material via specific image analysis measurement parameters such as area. This test method and equipment also provide the ability to measure the size of an opening 24, the roundness of an opening 24, the aspect ratio for an opening 24, the two-dimensional area of a node 12, and node 12 density and spacing. This test method involves obtaining two separate digital images of the sample.

Material Apertured Zone Sample Analysis Set-Up and Determination

Figure 15:
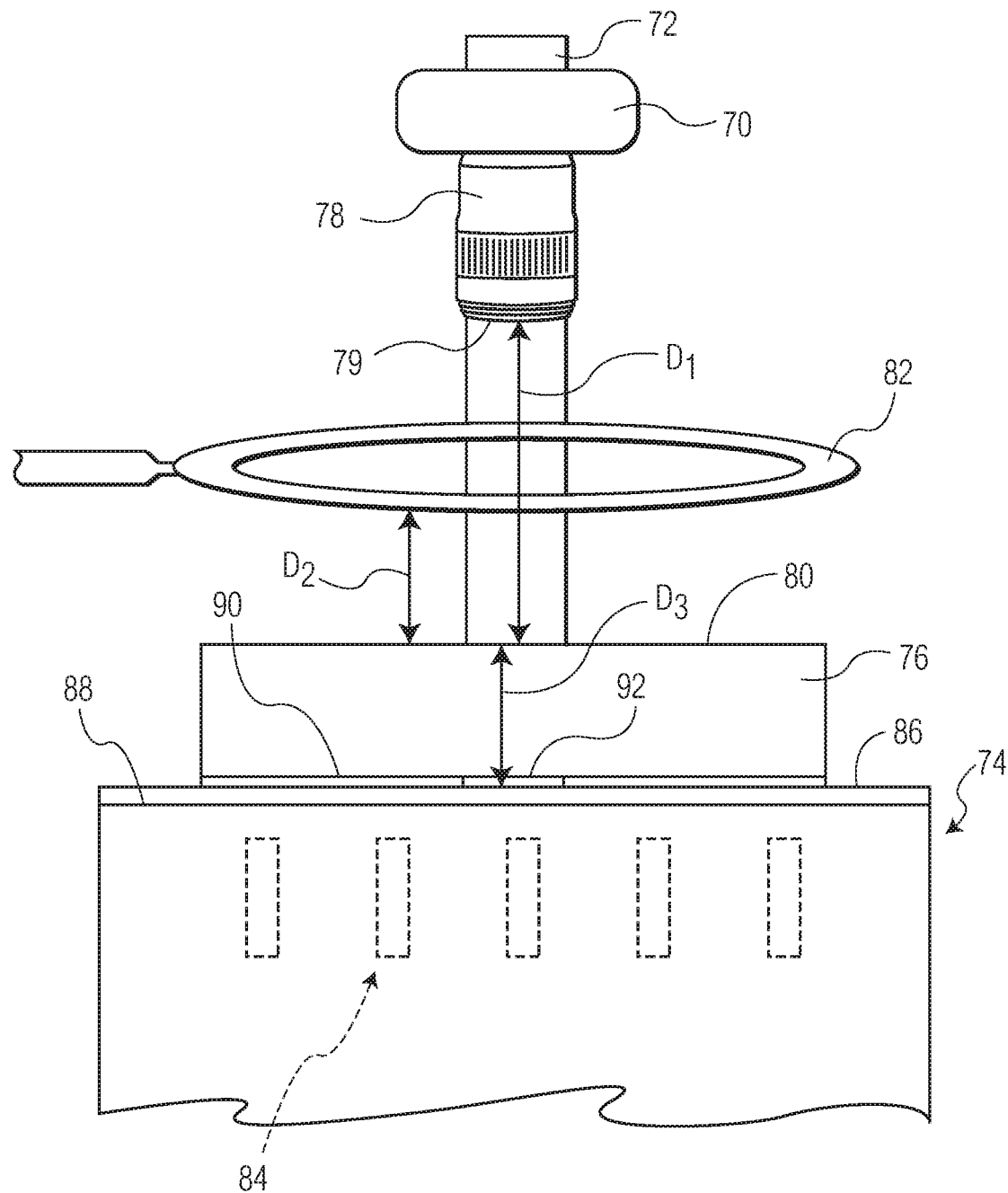
FIG. 15 is a perspective view of exemplary equipment and set-up to perform the Material Sample Analysis Test Method as described herein.

An exemplary setup for acquiring the images of the apertured zone is representatively illustrated in FIG. 15. Specifically, a CCD video camera 70 (e.g., a Leica DFC 300 FX video camera available from Leica Microsystems of Heerbrugg, Switzerland) is mounted on a standard support 72 such as a Polaroid MP-4 Land Camera standard support formerly available from Polaroid Resource Center in Cambridge, MS, and now potentially available from a resource such as eBay. The standard support 72 is attached to a macro-viewer 74 such as a KREONITE macro-viewer available from Dunning Photo Equipment, Inc., having an office in Bixby, Oklahoma. An auto stage 76 is placed on the upper surface of the macro-viewer 74. The auto stage 76 is used to automatically move the position of a given sample for viewing by the camera. A suitable auto stage 76 is Model H112, available from Prior Scientific Inc., having an office in Rockland, MA.

The specimen (not shown in FIG. 15) is placed on the auto stage 76 of a Leica Microsystems QWIN Pro Image Analysis system, under the optical axis of a 60 mm lens 78 having an f-stop setting of 4, such as a Nikon AF Micro Nikkor, manufactured by Nikon Corporation, having an office in Tokyo, Japan. The lens 78 is attached to the camera 70 using a c-mount adaptor. The distance from the front face of the lens 78 to the sample is approximately 55 cm. The sample is laid flat on the auto stage surface 80 and any wrinkles removed by gentle stretching and/or fastening it to the auto stage surface 80 using transparent adhesive tape at its outer edges. The sample surface is illuminated with incident fluorescent lighting provided by a 16 inch diameter, 40 watt, Circline fluorescent light 82, such as that manufactured by General Electric Company, having an office in Boston, MA The light 82 is contained in a fixture that is positioned so it is centered over the sample and is approximately 3 cm above the sample surface. The illumination level of the light 82 is controlled with a Variable Auto-transformer (not shown), type 3PN1010, available from Staco Energy Products Co. having an office in Dayton, OH. Transmitted light is also provided to the sample from beneath the auto stage by a bank of four, 2-foot, EMC, Double-End Powered LED tube lights 84 which are dimmable and available from Fulight Optoelectronic Materials, LLC. The LED lights 84 are covered with a diffusing plate 86. The diffusing plate 86 is inset into, and forms a portion of, the upper surface 88 of the macro-viewer 74. This illumination source is overlaid with black mask 90 possessing a 3-inch by 3-inch opening 92. The opening 92 is positioned so that it is centered under the optical axis of the camera 70 and lens 78 system. The distance D3 from the fluorescent light opening 92 to the surface 80 of the auto stage 76 is approximately 17 cm. The illumination level of the fluorescent light bank is also controlled with a separate power control box (not shown) configured for dimmable LED lights.

The image analysis software platform used to perform the percent open area and aperture size measurements is a QWIN Pro (Version 3.5.1) available from Leica Microsystems, having an office in Heerbrugg, Switzerland. Alternatively, LAS Macro Editor, the next generation of software following QWIN Pro, could be used to perform the analysis. The system and images are also accurately calibrated using the QWIN software and a standard ruler with metric markings at least as small as one millimeter. The calibration is performed in the horizontal dimension of the video camera image. Units of millimeters per pixel are used for the calibration.

Thus, the method for determining the percent open area and opening size of a given specimen includes the step of performing measurements on the transmitted light image. Specifically, an image analysis algorithm is used to acquire and process images as well as perform measurements using Quantimet User Interactive Programming System (QUIPS) language. The image analysis algorithm is reproduced below. For purposes of clarity, the references in the algorithm to "bumps" or "projections" refers to nodes 12 for the nonwoven material 10 and the references to "open areas" or "apertures" refers to openings 24 for the nonwoven material 10.

Define Variables & Open Files

```
The following line designates the computer location where data is sent to
Open File (C:\Data\94054 - Nhan (patent)\data.xls, channel #1)
TOTCOUNT = 0
TOTFIELDS = 0
MFRAMEH = 875
MFRAMEW = 1249
SAMPLE ID AND SET UP
Configure (Image Store 1392 x 1040, Grey Images 81, Binaries 24 )
Enter Results Header
File Results Header ( channel #1 )
File Line ( channel #1 )
PauseText ( "Enter sample image prefix name now." )
Input ( TITLE$ )
PauseText ( "Set sample into position." )
Image Setup DC Twain [PAUSE] ( Camera 1, AutoExposure Off, Gain 0.00, ExposureTime 34.23
msec, Brightness 0, Lamp 38.83 )
   Measure frame ( x 74, y 110, Width 1249, Height 875 )
   Image frame ( x 0, y 0, Width 1392, Height 1040 )
      -- Calvalue = 0.0377 mm/px
CALVALUE = 0.0377
Calibrate ( CALVALUE CALUNITS$ per pixel )
FRMAREA = MFRAMEH*MFRAMEW*(CALVALUE**2)
Clear Accepts
For ( SAMPLE = 1 to 1, step 1 )
   Clear Accepts
   File ( "Field No.", channel #1, field width: 9, left justified )
   File ( "% Open Area", channel #1, field width: 7, left justified )
   File ( "Bump Density", channel #1, field width: 13, left justified )
   File ( "Bump Spacing", channel #1, field width: 15, left justified )
   File Line ( channel #1 )
   Stage ( Define Origin )
   Stage ( Scan Pattern, 1 x 5 fields, size 82500.000000 x 39000.000000 )
   IMAGE ACQUISITION I - Projection isolation
   For ( FIELD = 1 to 5, step 1 )
      Measure frame ( x 74, y 110, Width 1249, Height 875 )
      Display ( Image0 (on), frames (on,on), planes (off,off,off,off,off,off), lut 0, x 0, y 0, z 1, Reduction
off )
      PauseText ( "Ensure incident lighting is correct (WL = 0.88 - 0.94) and acquire image." )
      Image Setup DC Twain [PAUSE] ( Camera 1, AutoExposure Off, Gain 0.00, ExposureTime 34.23
msec, Brightness 0, Lamp 38.83 )
      Acquire ( into Image0 )
      DETECT - Projections only
      PauseText ( "Ensure that threshold is set at least to the right of the left gray-level histogram peak
which corresponds to the 'land' region." )
      Detect [PAUSE] ( whiter than 129, from Image0 into Binary0 delineated )
      BINARY IMAGE PROCESSING
      Binary Amend ( Close from Binary0 to Binary1, cycles 10, operator Disc, edge erode on )
      Binary Identify ( FillHoles from Binary1 to Binary1 )
      Binary Amend ( Open from Binary1 to Binary2, cycles 20, operator Disc, edge erode on )
```

```
        Binary Amend ( Close from Binary2 to Binary3, cycles 8, operator Disc, edge erode on )
        PauseText ( "Toggle <control> and <b> keys to check projection detection and correct if
necessary." )
        Binary Edit [PAUSE] ( Reject from Binary3 to Binary3, nib Fill, width 2 )
        Binary Logical ( copy Binary3, inverted to Binary4 )
        IMAGE ACQUISITION 2 - % Open Area & Aperture Size
        Measure frame ( x 74, y 110, Width 1249, Height 875 )
        Display ( Image0 (on), frames (on,on), planes (off,off,off,off,off,off), lut 0, x 0, y 0, z 1, Reduction
off )
        PauseText ( "Turn off incident light & ensure transmitted lighting is correct (WL = 0.95) and
acquire image." )
        Image Setup DC Twain [PAUSE] ( Camera 1, AutoExposure Off, Gain 0.00, ExposureTime 34.23
msec, Brightness 0, Lamp 38.83 )
        Acquire ( into Image0 )
        ACQFILES = "C:\Images\94054 - Nhan\"+TITLE$+"_"+STR$(FIELD)+".jpg"
        Write image ( from ACQOUTPUT into file ACQFILE$ )
        DETECT - Open areas only
        Detect ( whiter than 127, from Image0 into Binary10 delineated )
        BINARY IMAGE PROCESSING
        Binary Amend ( Close from Binary10 to Binary11, cycles 5, operator Disc, edge erode on )
        Binary Identify ( FillHoles from Binary11 to Binary12 )
        Binary Amend ( Open from Binary12 to Binary13, cycles 10, operator Disc, edge erode on )
        Binary Identify ( EdgeFeat from Binary13 to Binary14 )
        PauseText ( "Ensure apertures are detected accurately." )
        Binary Edit [PAUSE] ( Reject from Binary14 to Binary14, nib Fill, width 2 )
        FIELD MEASUREMENTS - % Open Area, Bump Density & Spacing
          -- % open area
        MFLDIMAGE =10
        Measure field ( plane MFLDIMAGE, into FLDRESULTS(1), statistics into FLDSTATS(7,1) )
            Selected parameters: Area %
        Field Histogram #1 ( Y Param Number, X Param Area %, from 0. to 60., linear, 20 bins )
        PERCOPENAREA = FLDRESULTS(1)
          -- bump density & spacing
        MFLDIMAGE = 3
        Measure field ( plane MFLDIMAGE, into FLDRESULTS(5), statistics into FLDSTATS(7,5) )
            Selected parameters: Area, Intercept H, Intercept V, Area %,
            Count/Area
        BUMPDENSITY = FLDRESULTS(5)
        MNSPACE1 = (FRMAREA−FLDRESULTS(1))/(FLDRESULTS(2)+FLDRESULTS(3))/2
        Field Histogram #2 ( Y Param Number, X Param MNSPACE1, from 0. to 50., linear, 25 bins )
        File ( FIELD, channel #1, 0 digits after '.' )
        File ( PERCOPENAREA, channel #1, 1 digit after '.' )
        File ( BUMPDENSITY, channel #1, 1 digit after '.' )
        File ( MNSPACE1, channel #1, 1 digit after '.' )
        File Line ( channel #1 )
        FEATURE MEASUREMENTS - Aperture and bump sizes
          -- Bump Size
        Measure feature ( plane Binary3, 8 ferets, minimum area: 24, grey image: Image0 )
            Selected parameters: Area, X FCP, Y FCP, EquivDiam
        Feature Histogram #1 ( Y Param Number, X Param Area, from 1. to 100., logarithmic, 20 bins )
        Feature Histogram #2 ( Y Param Number, X Param EquivDiam, from 1. to 100., logarithmic, 20
bins )
          -- Aperture Size
        Measure feature ( plane Binary14, 8 ferets, minimum area: 24, grey image: Image0 )
            Selected parameters: Area, X FCP, Y FCP, Roundness, AspectRatio,
            EquivDiam
        Feature Histogram #3 ( Y Param Number, X Param Area, from 1. to 100., logarithmic, 20 bins )
        Feature Histogram #4 ( Y Param Number, X Param EquivDiam, from 1. to 100., logarithmic, 20
bins )
        Feature Histogram #5 ( Y Param Number, X Param Roundness, from 0.8999999762 to
2.900000095, linear, 20 bins )
        Feature Histogram #6 ( Y Param Number, X Param AspectRatio, from 1. to 3., linear, 20 bins )
        Stage ( Step, Wait until stopped + 1100 msecs )
    Next ( FIELD )
  Next ( SAMPLE )
  File Line ( channel #1 )
  File Line ( channel #1 )
  OUTPUT FEATURE HISTOGRAMS
  File ( "Bump Size (area - sq. mm)", channel #1 )
  File Line ( channel #1 )
  File Feature Histogram Results ( #1, differential, statistics, bin details, channel #1 )
  File Line ( channel #1 )
  File Line ( channel #1 )
  File ( "Bump Size (ECD - mm)", channel #1 )
  File Line ( channel #1 )
  File Feature Histogram Results ( #2, differential, statistics, bin details, channel #1 )
  File Line ( channel #1 )
  File Line ( channel #1 )
  File ( "Aperture Size (area - sq. mm)", channel #1 )
```

```
File Line ( channel #1 )
File Feature Histogram Results ( #3, differential, statistics, bin details, channel #1 )
File Line ( channel #1 )
File Line ( channel #1 )
File ( "Aperture Size (ECD - mm)", channel #1 )
File Line ( channel #1 )
File Feature Histogram Results ( #4, differential, statistics, bin details, channel #1 )
File Line ( channel #1 )
File Line ( channel #1 )
File ( "Aperture Roundness", channel #1 )
File Line ( channel #1 )
File Feature Histogram Results ( #5, differential, statistics, bin details, channel #1 )
File Line ( channel #1 )
File Line ( channel #1 )
File ( "Aperture Aspect Ratio", channel #1 )
File Line ( channel #1 )
File Feature Histogram Results ( #6, differential, statistics, bin details, channel #1 )
File Line ( channel #1 )
File Line ( channel #1 )
Close File ( channel #1 )
END
```

The QUIPS algorithm is executed using the QWIN Pro software platform. The analyst is initially prompted to enter the specimen set information which is sent to the EXCEL file.

The analyst then enters an image file prefix name corresponding to the specimen identification. This will be used by the algorithm to save images acquired during the analysis to a specified file location. The analyst is next prompted by a live image set up window on the computer monitor screen to place a specimen onto the auto-stage. The sample should be laid flat and gentle force applied at its edges to remove any macro-wrinkles that may be present. At this time, the Circline fluorescent light 82 can be on to assist in positioning the specimen. Next, the analyst is prompted to adjust the incident Circline fluorescent incident light 82 via the Variable Auto-transformer to a white level reading of approximately 0.9. The sub-stage transmitted light should either be turned off at this time or masked using a piece of light-blocking, black construction paper placed over the 3 inch by 3 inch opening 92.

The analyst is now prompted to ensure that the detection threshold is set to the proper level for detection of the nodes 12 using the Detection window which is displayed on the computer monitor screen. Typically, the threshold is set using the white mode at a point approximately near the middle of the 8-bit gray-level range (e.g. 127). If necessary, the threshold level can be adjusted up or down so that the resulting detected binary will optimally encompass the nodes 12 shown in the acquired image.

After the algorithm automatically performs several binary image processing steps on the detected binary of the nodes 12, the analyst will be given an opportunity to re-check node detection and correct any inaccuracies. The analyst can toggle both the 'control' and 'b' keys simultaneously to re-check node detection against the underlying acquired gray-scale image. If necessary, the analyst can select from a set of binary editing tools (e.g. draw, reject, etc.) to make any minor adjustments. If care is taken to ensure proper illumination and detection in the previously described steps, little or no correction at this point should be necessary.

Next, the analyst is prompted to turn off the incident Circline fluorescent light 82 and either turn on the sub-stage transmitted light or remove the light blocking mask. The sub-stage transmitted light is adjusted by the LED power controller to a white level reading of approximately 0.95. At this point, the image focus can be optimized for the apertured zone 16 of the material 10 including openings 24.

The algorithm, after performing additional operations on the resulting separate binary images for openings 24, will then prompt the analyst to re-check opening 24 detection against the underlying gray-scale image. If necessary, the analyst can select from a set of binary editing tools (e.g. draw, reject, etc.) to make any minor adjustments.

The algorithm will then automatically perform measurements and output the data into a designated EXCEL spreadsheet file.

Following the transfer of data, the algorithm will direct the auto-stage to move to the next field-of-view and the process of turning on the incident, Circline fluorescent light 82 and blocking the transmitted sub-stage lighting will begin again. This process will repeat four times so that there will be five sets of data from five separate field-of-view images per single sampling replicate.

After completion of the analysis, the following measurement parameter data will be located in the EXCEL file after measurements and data transfer has occurred:

Percent Open Area
  Node Density (No. per sq. metre)
  Node Spacing (mm)
  Node Size (One histogram for area in $mm^2$ and one histogram for equivalent circular diameter in mm)
  Aperture Size (One histogram for area in $mm^2$ and one histogram for equivalent circular diameter in mm)
Aperture Roundness
Aperture Aspect Ratio The final specimen mean spread value is usually based on an N=5 analysis from five, separate, specimen subsample replicates. A comparison of the percent open area, opening 24 (aperture) size and other parameters acquired by the algorithm between different specimens can be performed using a Student's T analysis at the 90% confidence level.

Material Side Zone Percent Open Area Set-Up and Determination

The setup for acquiring the images of the material side zones is similar to the set-up for acquiring images of the material apertured zone, with a few minor differences, as detailed below.

The camera and lens, the support, and the stage used to capture the images of the material side zones, and settings for the same, are all the same as used in the Material Apertured Zone Sample Analysis Set-up and Determination. However, in the present set-up, no macro-viewer was used. The test material side zone sample is prepared and placed onto the auto-stage surface 80 as in the Material Apertured Zone Sample Analysis Set-up and Determination. However, instead of illuminating the sample surface with incident fluorescent lighting provided by a Circline fluorescent light, light was transmitted to the sample from under the sample by a ChromaPro 45 device, formerly available from Circle S in Tempe, AZ, that had a 3-inch by 3-inch sized opening black mask overlaid on its surface.

As with the Material Apertured Zone Sample Analysis Set-up and Determination, the image analysis software platform used to perform the percent open area measurement for the material side zones is the QWIN Pro (Version 3.5.1) available from Leica Microsystems. Alternatively, LAS Macro Editor, the next generation of software following QWIN Pro, could be used to perform the analysis. The system and images are also accurately calibrated using the QWIN software and a standard ruler with metric markings at least as small as one millimeter. The calibration is performed in the horizontal dimension of the video camera image. Units of millimeters per pixel are used for the calibration.

In the Material Side Zone Percent Open Area Set-up and Determination, upon running the QWIN Pro program, the light level was set at 0.95 using the white level function in the QWIN Pro program to adjust the light output of the ChromaPro light output. The QWIN Pro program was further configured to move the Prior auto-stage so that six images were automatically acquired and measured from each side of the sample material, resulting in twelve total measurements.

Thus, the method for determining the percent open area of a side zone includes the step of performing measurements on the transmitted light image. Specifically, an image analysis algorithm is used to acquire and process images as well as perform measurements using Quantimet User Interactive Programming System (QUIPS) language. The image analysis algorithm is reproduced below.

Define Variables & Open Files

```
The following line designates the computer location where data is sent to
Open File ( D:\Data\103470 - Nhan\data.xls, channel #1 )
   TOTCOUNT = 0
   TOTFIELDS = 0
   MFRAMEH = 875
   MFRAMEW = 1249
   SAMPLE ID AND SET UP
   Configure ( Image Store 1392 x 1040, Grey Images 81, Binaries 24 )
   Enter Results Header
   File Results Header ( channel #1 )
   File Line ( channel #1 )
   PauseText ( "Enter sample image prefix name now." )
   Input ( TITLE$ )
   Measure frame ( x 511, y 50, Width 446, Height 940 )
   Image frame ( x 0, y 0, Width 1392, Height 1040 )
   PauseText ( "Set sample into position." )
   Image Setup DC Twain [PAUSE] ( Camera 1, AutoExposure Off, Gain 0.00, ExposureTime 34.23 msec, Brightness 0, Lamp 38.83 )
   -- Calvalue = 0.0333 mm/px
   CALVALUE = 0.0333
   Calibrate ( CALVALUE CALUNITS$ per pixel )
   FRMAREA = MFRAMEH*MFRAMEW*(CALVALUE**2)
   File ( "Field No.", channel #1, field width: 9, left justified )
   File ( "% Open Area", channel #1, field width: 7, left justified )
   File Line ( channel #1 )
   For ( SAMPLE = 1 to 2, step 1 )
      Clear Accepts
      Stage ( Define Origin )
      Stage ( Scan Pattern, 1 x 6 fields, size 82500.000000 x 39000.000000 )
      For ( FIELD = 1 to FIELDS, step 1 )
         IMAGE ACQUISITION
         ACQOUTPUT = 0
         Measure frame ( x 511, y 50, Width 446, Height 940 )
         Display ( Image0 (on), frames (on,on), planes (off,off,off,off,off,off), lut 0, x 0, y 0, z 1, Reduction off )
         PauseText ( "Turn off incident light & ensure transmitted lighting is correct (WL = 0.95) and acquire image." )
         Image Setup DC Twain [PAUSE] ( Camera 1, AutoExposure Off, Gain 0.00, ExposureTime 34.23 msec, Brightness 0, Lamp 38.83 )
            Acquire ( into Image0 )
            ACQFILE$ = "D:\Images\103470 - Nhan\"+TITLE$+"_"+STR$(FIELD)+".jpg"
            Write image ( from ACQOUTPUT into file ACQFILE$ )
            DETECT - Open areas only
            Detect ( whiter than 164, from Image0 into Binary10 )
            BINARY IMAGE PROCESSING
            Binary Amend ( Close from Binary10 to Binary11, cycles 1, operator Disc, edge erode on )
            Binary Identify ( FillHoles from Binary11 to Binary12 )
            Binary Identify ( EdgeFeat from Binary12 to Binary13 )
            FIELD MEASUREMENTS
            -- % open area
            MFLDIMAGE = 13
```

```
    Measure field ( plane MFLDIMAGE, into FLDRESULTS(1), statistics into FLDSTATS(7,1) )
        Selected parameters: Area%
        Field Histogram #1 ( Y Param Number, X Param Area%, from 0. to 5., linear, 20 bins )
        Display Field Histogram Results ( #1, horizontal, differential, bins + graph (Y axis linear), statistics
)
        Data Window ( 1449, 599, 423, 270 )
        PERCOPENAREA = FLDRESULTS(1)
        File ( FIELD, channel #1, 0 digits after '.' )
        File ( PERCOPENAREA, channel #1, 1 digit after '.' )
        File Line ( channel #1 )
        FEATURE MEASUREMENTS
        -- Aperture Size
        Stage ( Step, Wait until stopped + 1100 msecs )
    Next ( FIELD )
    File Line ( channel #1 )
    PauseText ( "Load next replicate now." )
    Image Setup DC Twain [PAUSE] ( Camera 1, AutoExposure Off, Gain 0.00, ExposureTime 23.16
msec, Brightness 0, Lamp 38.83 )
    Next ( SAMPLE )
    File Line ( channel #1 )
    OUTPUT FEATURE HISTOGRAMS
    File ( "% Area Histogram", channel #1 )
    File Line ( channel #1 )
    File Line ( channel #1 )
    File Field Histogram Results ( #1, differential, statistics, bin details, channel #1 )
    Close File ( channel #1 )
END
```

In the Material Side Zone Percent Open Area Set-up and Determination, the QUIPS algorithm is executed using the QWIN Pro software platform. The analyst is initially prompted to enter the specimen set information which is sent to the EXCEL file.

The analyst then enters an image file prefix name corresponding to the specimen identification. This will be used by the algorithm to save images acquired during the analysis to a specified file location. The analyst is next prompted by a live image set up window on the computer monitor screen to place a specimen onto the auto-stage. The sample should be laid flat and gentle force applied at its edges to remove any macro-wrinkles that may be present. At this point, the light level should be set at 0.95 using the white level function in the QWIN Pro program to adjust the light output of the ChromaPro light output, if not already done so. At this point, the image focus can be optimized for the side zone 26a, or 26b of the material 10 including micro-apertures 81 and/or regions of greatly reduced fiber density 39.

The algorithm, after performing additional operations on the resulting separate binary images for micro-apertures 81 and/or regions of greatly reduced fiber density 39, will then prompt the analyst to re-check detection of the micro-apertures 81 and/or regions of greatly reduced fiber density 39 against the underlying gray-scale image. If necessary, the analyst can select from a set of binary editing tools (e.g. draw, reject, etc.) to make any minor adjustments.

The algorithm will then automatically perform measurements and output the data into a designated EXCEL spreadsheet file.

Following the transfer of data, the algorithm will direct the auto-stage to move to the next field-of-view. This process will repeat six times along each edge of the material side zone sample so that there will be twelve sets of data from twelve separate field-of-view images per single sampling replicate.

After completion of the analysis, the following measurement parameter data will be located in the EXCEL file after measurements and data transfer has occurred:

Percent Open Area

The final specimen mean spread value is usually based on an N=5 analysis from five, separate, specimen subsample replicates. A comparison of the percent open area acquired by the algorithm between different specimens can be performed using a Student's T analysis at the 90% confidence level.

Compression Energy Test

The Compression Energy test utilized herein is a three-cycle compression test can be performed to measure the compression resiliency of projections on single layer projection layer. Compression resiliency is measured by measuring compression energy. Generally, compression energy refers to the energy required to compress the projection layer from its initial thickness at 5 grams force (about 0.027 kPa) down to its final thickness at about 1830 grams force (about 10 kPa). Compression energy is calculated as the area under the compression stress (force/area) versus linear thickness curve define by initial contact pressure (5 grams force) and finial contact pressure at about 1830 grams force (about 10 kPa).

1. If the nonwoven material desired to be tested forms part of a composite or absorbent article, use "freeze off" spray to carefully remove the nonwoven material.
2. From the nonwoven material, cut a circular test sample using a 47.8 mm diameter cutting die.
3. The upper and lower platens made of stainless steel are attached to a tensile tester.
4. The top platen has a diameter of 89 mm while the lower platen has a diameter of 152 mm. The upper platen is connected to a 100 N load cell while the lower platen is attached to the base of the tensile tester.
5. TestWorks Version 4 software program provided by MTS is used to control the movement of the upper platen and record the load and the distance between the two platens.
6. The upper platen is activated to slowly move downward and touch the lower platen until the compression load reaches around 5000 g. At this point, the distance between the two platens is zero.

7. The upper platen is then set to move upward (away from the lower platen) until the distance between the two platens reaches 15 mm.
8. The crosshead reading shown on TestWorks Version 4 software program is set to zero.
9. A test sample is placed on the center of the lower platen with the nodes facing toward the upper platen.
10. The upper platen is activated to descend toward the lower platen and compress the test sample at a speed of 10 mm/min. The distance that the upper platen travels is indicated by the crosshead reading. This is a loading process.
11. The compression should continue until the load exceeds 1830 grams force (about 10 kPa), at which point the platen should reverse direction and travel up at a rate of 10 mm/minute until the force decreases below 5 grams force. The platen should then reverse direction and be in a second compression cycle at a rate of 10 mm/minute until a load of 1830 grams force (about 10 kPa) is exceeded. Once the load exceeds 1830 grams force (about 10 kPa), at which points the platen should reverse direction and travel up at a rate of 10 mm/minute until the force decreases below 5 grams force. The platen should then reverse direction again and be in a third compression cycle at a rate of 10 mm/minute until a load of 1830 grams force (about 10 kPa) is exceeded. At that point, the upper platen stops moving downward and returns at a speed of 10 mm/min to its initial position where the distance between the two platens is 15 mm.
12. The compression load and the corresponding distance between the two platens during the loading and unloading are recorded on a computer using TestWorks Version 4 software program provided by MTS.
13. The compression load is converted to the compression stress by dividing the compression force by the area of the test sample, which is 17.94 cm$^2$.
14. The distance between the two platens at a given compression stress represents the thickness under that particular compression stress.
15. A total of six test samples are tested for each test sample code to get representative loading and unloading curves for each test sample code.

Compression Linearity Test

Compression Linearity is measured using the Kawabata Evaluation System KES model FB-3, again available from Kato Tech Company.

The instrument is designed to measure the compression properties of materials by compressing the sample between two plungers. To measure the compression properties, the top plunger is brought down on the sample at a constant rate until it reaches the maximum preset force. The displacement of the plunger is detected by a potentiometer. The amount of pressure taken to compress the sample (P, gf/cm2) vs. thickness (displacement) of the material (T, mm) is plotted on the computer screen. For all the materials in this study, the following instrument settings were used:
  Sensitivity=2×5
  Gear (speed)=1 mm/50 sec
  Fm set=5.0
  Stroke select=Max 5 mm
  Compression area=2 cm$^2$
  Time lag=standard
  Max compression force=50 gf The KES algorithm calculates the following compression characteristic values and displays them on a computer screen:
  Compression Linearity (LC).
  5 measurements were taken on each sample.

Tensile Strength Test Method

The Tensile Strength Test Method utilized herein is performed to measure the compression tensile strength of each of the side zones 26a, 26b and the apertured region of the materials of the present disclosure. The tensile strengths are generally reported as a lbs force value (grams force) at a given strain.

1. If the nonwoven material desired to be tested forms part of a composite or absorbent article, "freeze off" spray should be used to carefully remove the nonwoven material.
2. From the nonwoven material, the side zones are cut from the apertured zone using a paper cutter along the machine direction. There should be about 1 mm of the side zone left on each side of the apertured zone after cutting. The three pieces (side Zone 1, side Zone 2, and apertured zone) are tested separately on a tensile frame.
3. The upper and lower grips should be wider than width of a test samples. The upper grip is connected to a 100 N load cell while the lower grip is attached to the base of the tensile tester.
4. TestWorks Version 4 software program provided by MTS is used to control the movement of the upper grip and record the load and the distance between the two grips. Test setting are:
  Gauge length=76.2 mm
  Crosshead speed=305 mm/min
  Slack Pre-load=25 grams force
5. A test sample with the longitudinal direction oriented vertically is placed on the center of the lower grips
6. The upper grip is activated to pull upward at a speed of 305 mm/min. The distance that the upper grip travels is indicated by the crosshead reading.
7. The tensile load and the corresponding distance the upper grip travels during the test are recorded on a computer using TestWorks Version 4 software program provided by MTS.
8. The travel distance of the upper grip is converted to percent strain by dividing the travel distance by the gauge length and multiply by 100.

Once the data has been recorded, a Tensile Strength Ratio parameter can be calculated. The Tensile Strength Ratio is determined in the following manner. With the results of the Tensile Strength Test Method, for each of the side zones 1 and 2 and the apertured zone 16, a strain common to each of the side zone 1, side zone 2, and the apertured zone samples is found at which the total load (load of side zone 1 at the common strain+load of side zone 2 at the common strain+load of the apertured zone at the common strain) is equal to 1.2 pound force (544.3 grams force). Where there is no common strain for which the combined load is equal to 1.2 lbs force, a common strain for which the combined load is as close to 1.2 lbs force as possible is chosen. However, the combined load should still be within +/−10% of 1.2 lbs force. Once this common strain value has been found, the Tensile Strength Ratio parameter may be determined according to the below equation (1).

Ratio=(load of side zone 1 at the common strain+ load of side zone 2 at the common strain)/(load of apertured zone at the common strain)  (1)

Poisson's Ratio Test Method

The Possion's Ratio Test Method can be used to determine an amount of necking a material may experience when placed under longitudinal tension. More specifically, Poisson's ratio is a measure of the transverse strain of a material divided by the longitudinal strain. Poisson's ratios herein are reported as a ratio at a given longitudinal strain.

The steps of the Poisson's Ratio Test Method begin the same as the steps 1-5 of the Tensile Strength Test Method, with the sample being the apertured zone of the sample material. The following steps are specific to the Poisson's Ratio Test Method:

6. The width of the sample apertured zone material is marked at mid-point of the sample material between the upper and lower grips with a felt-tipped marker or other marking device, and the width of the sample material is measured along the marked section and recorded.
7. The upper grip is activated to pull upward at a speed of 305 mm/min until 1% longitudinal strain of the sample material is achieved. Once 1% longitudinal strain is achieved, the upper grip is stopped.
8. The width of the sample material is measured along the marked section and recorded.
9. The steps 7 and 8 are repeated for 2%, 3%, 4%, and 5% longitudinal strain.
10. Transverse strain values for the sample material are calculated at each of the achieved longitudinal strains.
11. The Poisson's ratio is then determined for the sample material at each recorded longitudinal strain by dividing the determined transverse strain values by their associated longitudinal strain value.

Ligament Anisotropy Test Method

The anisotropy of fibers in the connecting ligaments 14 extending between longitudinally adjacent nodes 12 and the connecting ligaments 14 extending between laterally adjacent nodes 12 can be determined by using the image analysis measurement method described herein.

In this context, fiber anisotropy is considered for a plurality connecting ligaments 14 within an apertured zone 16 of a material, for each respective material. Generally, the image analysis method determines a numeric value of anisotropy from approximately eight cross-sectional (coronal) images of a connecting ligament 14 via a specific image analysis measurement parameter named anisotropy. The anisotropy of a connecting ligament 14 can be measured by using x-ray Micro-computed Tomography (a.k.a. Micro-CT) to non-destructively acquire images with subsequent image analysis techniques to detect fiber components and then measuring the anisotropy of said components within the connecting ligament 14 regions only. The image analysis algorithm performs detection, image processing and measurement and also transmits data digitally to a spreadsheet database. The resulting measurement data are used to compare the anisotropy of connecting ligaments 14 extending between longitudinally adjacent nodes 12 and connecting ligaments 14 extending between laterally adjacent nodes 12.

The method for determining the anisotropy in each connecting ligaments' fibers includes the first step of acquiring digital x-ray Micro-CT images of a sample. These images are acquired using a SkyScan 1272 Micro-CT system available from Bruker microCT (2550 Kontich, Belgium). The sample is attached to a mounting apparatus, supplied by Bruker with the SkyScan 1272 system, so that it will not move under its own weight during the scanning process. The following SkyScan 1272 conditions are used during the scanning process:

Camera Pixel Size (um)=9.0
  Source Voltage (kV)=35
  Source Current (uA)=225
  Image Pixel Size (um)=6.0
  Image Format=TIFF
  Depth (bits)=16
  Rotation Step (deg.)=0.10
  Use 360 Rotation=NO
  Frame Averaging=ON (6)
  Random Movement=ON (1)
  Flat Field Correction=ON
  Filter=No Filter After sample scanning is completed, the resulting image set is then reconstructed using the NRecon program provided with the SkyScan 1272 Micro-CT system. While reconstruction parameters can be somewhat sample dependent, and should be known to those skilled in the art, the following parameters should provide a basic guideline to an analyst:

Image File Type=JPG
  Pixel Size (um)=6.00
  Smoothing=1 (Gaussian)
  Ring Artifact Correction=10
  Beam Hardening Correction (%)=10

After reconstruction is completed, the resulting image data set is now ready for extraction of cross-sectional image slices using the Bruker SkyScan software package called DataViewer (v. 1.5.6.3). After downloading the entire reconstructed image data set into DataViewer, the analyst, skilled in the art of Micro-CT technologies, must then select and extract cross-sectional (coronal) image slices at eight different locations along each examined connecting ligament 14. In a typical process, six different connecting ligaments 14 of each type (e.g. connecting ligaments 14 extending between longitudinally adjacent nodes 12 and connecting ligaments 14 extending between laterally adjacent nodes 12) are analyzed. Once a set of cross-sectional Micro-CT images have been acquired for each desired connecting ligament 14, anisotropy measurements can now be made using image analysis software.

The image analysis software platform used to perform the anisotropy measurements is a QWIN Pro (Version 3.5.1) available from Leica Microsystems, having an office in Heerbrugg, Switzerland.

Thus, the method for determining the anisotropy of a given sample includes the step of performing several anisotropy measurements on the Micro-CT image set. Specifically, an image analysis algorithm is used to read and process images as well as perform measurements using Quantimet User Interactive Programming System (QUIPS) language. The image analysis algorithm is reproduced below.

Open Data Files & Set Variables

```
The following line designates the computer location where data is sent to
   Open File ( C:\Data\103470 - Nhan\data.xls, channel #1 )
   ACQOUTPUT = 0
   SET-UP AND CALIBRATION
   Configure ( Image Store 1504 x 1250, Grey Images 102, Binaries 32 )
     -- Pixel calibration value = 6.00 um/px
```

```
CALVALUE = 6.00
Calibration ( Local )
Image frame ( x 0, y 0, Width 1504, Height 1250 )
Measure frame ( x 31, y 61, Width 1442, Height 1188 )
Enter Results Header
File Results Header ( channel #1 )
File Line ( channel #1 )
File Line ( channel #1 )
   -- Enter image file information
PauseText ( "Enter image file prefix name." )
Input ( TITLE$ )
Clear Feature Histogram #1
Clear Feature Histogram #2
Clear Field Histogram #1
FIELD/ANALYSIS LOOP
For ( FIELD = 440 to 480, step 5 )
   IMAGE ACQUISITION & DETECTION
      -- Image File location
   ACQFILE$ = "C:\Images\103470 - Nhan\Coronal Images\Rep #3\"+TITLE$+""+STR$(FIELD)+".jpg"
   Read image ( from file ACQFILE$ into ACQOUTPUT )
   DETECTION OF FIBERS
   Clear Feature Histogram #1
   Clear Feature Histogram #2
   Detect ( whiter than 55, from Image0 into Binary0 delineated )
   IMAGE PROCESSING
   Binary Amend ( Close from Binary0 to Binary1, cycles 1, operator Disc, edge erode on )
   Binary Amend ( White Exh. Skeleton from Binary1 to Binary2, cycles 1, operator Disc, edge erode
on, alg. 'L' Type )
   Binary Identify ( Remove White Triples from Binary2 to Binary3 )
   Display ( Image0 (on), frames (on,on), planes (off,off,off,3,off,off), lut 0, x 0, y 0, z 1, Reduction off )
   MEASURE FIELD ANISOTROPY
   PauseText ( "Set measure frame region now." )
   Measure frame [PAUSE] ( x 1296, y 255, Width 506, Height 497 )
   MFLDIMAGE = 3
   Measure field ( plane MFLDIMAGE, into FLDRESULTS(1), statistics into FLDSTATS(7,1) )
      Selected parameters: Anisotropy
   ANISOT = FLDRESULTS(1)
   MEASURE FEATURE ORIENTATION
   Clear Accepts
   Measure feature ( plane Binary3, 64 ferets, minimum area: 10, grey image: Image0 )
      Selected parameters: X FCP, Y FCP, VertProj, HorizProj, Length,
         Perimeter, UserDef1, UserDef2, DerivOrient
   Feature Expression ( UserDef1 ( all features ), title Orient = PHPROJ(FTR)/PVPROJ(FTR) )
   Feature Expression ( UserDef2 ( all features ), title Length = PPERIMETER(FTR)/2 )
   Feature Histogram #1 ( Y Param UserDef2, X Param DerivOrient, from 0. to 180., linear, 20 bins )
   Feature Histogram #2 ( Y Param UserDef2, X Param UserDef1, from 1.999999955e-002 to 200.,
logarithmic, 20 bins )
   Display Feature Histogram Results ( #1, horizontal, differential, bins + graph (Y axis linear),
statistics )
      Data Window ( 1336, 117, 341, 454 )
   Display Feature Histogram Results ( #2, horizontal, differential, bins + graph (Y axis linear),
statistics )
      Data Window ( 1329, 566, 341, 454 )
      -- Output data to spreadsheet
   File Feature Histogram Results ( #1, differential, statistics, bin details, channel #1 )
   File Line ( channel #1 )
   File Line ( channel #1 )
   File Feature Histogram Results ( #2, differential, statistics, bin details, channel #1 )
   File Line ( channel #1 )
   File Line ( channel #1 )
   File ( "Anisotropy = ", channel #1 )
   File ( ANISOT, channel #1, 3 digits after '.' )
   File Line ( channel #1 )
   File Line ( channel #1 )
   File Line ( channel #1 )
Next ( FIELD )
Close File ( channel #1 )
```

The QUIPS algorithm is executed using the QWIN Pro software platform. The analyst is initially prompted to enter the number of images in the set for a particular specimen. Next, the analyst is prompted to enter specimen identification information which is sent to the EXCEL file.

The analyst is next prompted by an interactive command window and an input window to enter the image file prefix of the Micro-CT images to be analyzed. After this step, all subsequent images for a given sample will be read automatically by the image analysis algorithm described above.

The analyst is next prompted to manually select, with the computer mouse, the connecting ligament region of interest for analysis. Care should be taken to select only the connecting ligament of interest.

After several steps of image processing that will occur automatically, the analyst will again be prompted to clean up any over-extended region of interest (ROI) areas. This is done using the computer mouse as well as toggling the overlying binary image on and off by simultaneously using the 'control' and 'b' keys on the computer keyboard. After this step, the binary should only be covering the connecting ligament.

The process of selecting the connecting ligament 14 region of interest and clean up of over-extended regions will repeat until all the images for a particular specimen have been analyzed.

After all images have been analyzed, the following measurement parameter data will be located in the corresponding EXCEL file:

| Replicate # |
|---|
| Anisotropy |

There will be 6 values listed in columns for the Anisotropy parameter. For the purposes of comparing anisotropy values between connecting ligaments 14 which connect longitudinally adjacent nodes 12 and connecting ligaments 14 which connect laterally adjacent nodes 12, the data in the column labeled 'Anisotropy' can be compared between different specimens by performing a Student's T analysis at the 90% confidence level.

Embodiments

Embodiment 1: In a first embodiment, an absorbent article may have a front waist region with a front waist edge, a rear waist region with a rear waist edge, and a crotch region disposed between the front waist region and the rear waist region, and the article may comprise an outer cover, a bodyside liner, an absorbent body disposed between the outer cover and the body side liner, and a nonwoven material coupled to the bodyside liner having a front edge, a rear edge, and a material length. The nonwoven material may comprise an apertured zone comprising a plurality of openings formed between nodes and connecting ligaments of the nonwoven material and providing a percent open area for the apertured zone of the nonwoven material that is greater than about 15%, as determined by the Material Sample Analysis Test Method. The nonwoven material may be coupled to bodyside liner by a primary front waist bond extending throughout a primary front waist bonding region and a primary rear waist bond extending throughout a primary rear waist bonding region, the primary front waist bonding region extending through the apertured zone and the primary rear waist bonding region being spaced from the primary front waist bonding region, and the primary rear waist bonding region may have a length that is between about 2% and about 10% of the material length and the primary front waist bonding region may have a length that is between about 20% and about 50% of the material length.

Embodiment 2: In a second embodiment, the primary front waist bond of embodiments 1 may comprise a mechanical bond.

Embodiment 3: In a third embodiment, the primary rear waist bond of any one of embodiment 1 or embodiment 2 may comprise an adhesive bond.

Embodiment 4: In a fourth embodiment, the primary rear waist bonding region of any one of the embodiments 1-3 may have a primary rear bonding region edge and the primary rear bonding region edge may be spaced from the nonwoven material rear edge by at least 2 mm.

Embodiment 5: In a fifth embodiment, the primary rear waist bond of any one of the embodiments 1-4 may have a primary rear bonding region edge and the primary rear bonding region edge may be spaced from the nonwoven material rear edge by at least 5 mm.

Embodiment 6: In a sixth embodiment, the nonwoven material of any one of embodiments 1-5 may further be coupled to the bodyside liner by a secondary rear waist bond which at least partially overlaps the primary rear waist bond.

Embodiment 7: In a seventh embodiment, the primary rear waist bond and the secondary rear waist bond of any of the embodiments 1-6 may be a mechanical bond and an adhesive bond, respectively, and the adhesive of the secondary rear waist bond may be disposed in an amount of between about 10 gsm and about 40 gsm.

Embodiment 8: In an eighth embodiment, the adhesive of the secondary rear waist bond of embodiment 7 may be disposed in an amount of between about 10 gsm and about 20 gsm.

Embodiment 9: In a ninth embodiment, the nonwoven material further of any one of the embodiments 1-9 may further comprise a first side zone and a second side zone, the first side zone and the second side zone each extending between the nonwoven material rear edge and the nonwoven material front edge, each of the first side zone and the second side zone being bonded to the bodyside liner by adhesive within side zone adhesive bonding regions.

Embodiment 10: In a tenth embodiment, the adhesive within the side zone adhesive bonding regions of embodiment 9 may be disposed in an amount of between about 6.5 gsm and about 12.5 gsm.

Embodiment 11: In an eleventh embodiment, each of the first side zone and the second side zone of any one of embodiment 9 or embodiment 10 may have respective side zone widths, and wherein the side zone adhesive bonding regions bonding each of the first side zone and the second side zone to the bodyside liner may have side zone adhesive bonding region widths, each of the side zone adhesive bonding region widths being between about 50% and about 90% of respective side zone widths.

Embodiment 12: In a twelfth embodiment, an absorbent article may have a front waist region with a front waist edge, a rear waist region with a rear waist edge, and a crotch region disposed between the front waist region and the rear waist region, the article may further comprise an outer cover, a bodyside liner, an absorbent body disposed between the outer cover and the body side liner, and a nonwoven material having a front edge, a rear edge, and a material length coupled to the bodyside liner. The nonwoven material may further comprise an apertured zone comprising a plurality of openings formed between nodes and connecting ligaments of the nonwoven material and providing a percent open area for the apertured zone of the nonwoven material that is greater than about 15%, as determined by the Material Sample Analysis Test Method, wherein the nonwoven material is coupled to the bodyside liner by a rear waist mechanical bond extending through the apertured zone and covering a primary rear waist bonding region, a rear waist adhesive bond extending through the apertured zone and covering a secondary rear waist bonding region which at least partially overlaps the primary rear waist bonding region, and a front waist bond extending through the apertured zone and covering a front waist bonding region that is spaced from the primary rear waist bonding region and the secondary rear waist bonding region. The front waist bonding region may further have a length that is between about 20% and about 50% of the material length, the primary rear waist bonding region may further have a length that is between about 2% and about 10% of the material length, and the secondary rear waist bonding region may further have a length that is between about 2% and about 10% of the material length.

Embodiment 13: In a thirteenth embodiment, the secondary rear waist bonding region of embodiment 12 may completely overlap the primary rear waist bonding region.

Embodiment 14: In a fourteenth embodiment, the secondary rear waist bonding region of any one of embodiment 12 or embodiment 13 may have a rear bond region edge which is spaced from the nonwoven material rear edge by between about 2 mm and about 10 mm.

Embodiment 15 In a fifteenth embodiment, the secondary rear waist bonding region of any one of embodiments 12-14 may have a rear bond region edge which is spaced from the nonwoven material rear edge by between about 2 mm and about 5 mm.

Embodiment 16: In a sixteenth embodiment, the adhesive of the rear waist adhesive bond of any one of embodiments 12-15 may be disposed in an amount of between about 10 gsm and about 20 gsm.

Embodiment 17: In a seventeenth embodiment, the adhesive of the rear waist adhesive bond of any one of embodiments 12-16 may be disposed in an amount of between about 12 gsm and about 18 gsm.

Embodiment 18: In an eighteenth embodiment, the nonwoven material of any one of embodiments 12-17 may further comprise a first side zone and a second side zone, the first side zone and the second side zone each extending between the nonwoven material rear edge and the nonwoven material front edge, each of the first side zone and the second side zone being bonded to the bodyside liner by adhesive within side zone adhesive bonding regions.

Embodiment 19: In a nineteenth embodiment, the adhesive within the side zone adhesive bonding regions of embodiment 18 may be disposed in an amount of between about 6.5 gsm and about 12.5 gsm.

Embodiment 20: In a twentieth embodiment, the secondary rear waist bonding region of any one of the embodiments 12-19 may have a length that is between about 2% and about 5% of the material length.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front waist region with a front waist edge, a rear waist region with a rear waist edge, and a crotch region disposed between the front waist region and the rear waist region, the article comprising:
   an outer cover;
   a bodyside liner having a body-facing surface;
   an absorbent body disposed between the outer cover and the body side liner; and
   a nonwoven material coupled to the body-facing surface of the bodyside liner and having a front edge, a rear edge, and a material length, the nonwoven material comprising:
   an apertured zone comprising a plurality of openings formed between nodes and connecting ligaments of the nonwoven material and providing a percent open area for the apertured zone of the nonwoven material that is greater than 15%, as determined by the Material Sample Analysis Test Method;
   wherein the nonwoven material is coupled to bodyside liner by a primary front waist bond extending throughout a primary front waist bonding region and a primary rear waist bond extending throughout a primary rear waist bonding region, the primary front waist bonding region extending through the apertured zone and the primary rear waist bonding region being spaced from the primary front waist bonding region,
   wherein the primary rear waist bonding region has a length that is between 2% and 10% of the material length and the primary front waist bonding region has a length that is between 20% and 50% of the material length and
   wherein the nonwoven material is further coupled to the bodyside liner by a secondary rear waist bond which at least partially overlaps the primary rear waist bond.

2. The article of claim 1, wherein the primary front waist bond comprises a mechanical bond.

3. The article of claim 2, wherein the primary rear waist bond comprises an adhesive bond.

4. The article of claim 3, wherein the primary rear waist bonding region has a primary rear bonding region edge and the primary rear bonding region edge is spaced from the nonwoven material rear edge by at least 2 mm.

5. The article of claim 3, wherein the primary rear waist bond has a primary rear bonding region edge and the primary rear bonding region edge is spaced from the nonwoven material rear edge by at least 5 mm.

6. The article of claim 1, wherein the primary rear waist bond is a mechanical bond and the secondary rear waist bond is an adhesive bond, and wherein the adhesive of the secondary rear waist bond is disposed in an amount of between 10 gsm and 40 gsm.

7. The article of claim 6, wherein the adhesive of the secondary rear waist bond is disposed in an amount of between 10 gsm and 20 gsm.

8. The article of claim 1, wherein the nonwoven material further comprises a first side zone and a second side zone, the first side zone and the second side zone each extending between the nonwoven material rear edge and the nonwoven material front edge, each of the first side zone and the second side zone being bonded to the bodyside liner by adhesive within side zone adhesive bonding regions.

9. The article of claim 8, wherein the adhesive within the side zone adhesive bonding regions is disposed in an amount of between 6.5 gsm and 12.5 gsm.

10. The article of claim 8, wherein each of the first side zone and the second side zone have respective side zone widths, and wherein the side zone adhesive bonding regions bonding each of the first side zone and the second side zone to the bodyside liner have side zone adhesive bonding region widths, each of the side zone adhesive bonding region widths being between 50% and 90% of respective side zone widths.

11. An absorbent article having a front waist region with a front waist edge, a rear waist region with a rear waist edge, and a crotch region disposed between the front waist region and the rear waist region, the article comprising:
- an outer cover;
- a bodyside liner;
- an absorbent body disposed between the outer cover and the body side liner; and
- a nonwoven material having a front edge, a rear edge, and a material length coupled to the bodyside liner, the nonwoven material comprising:
  - an apertured zone comprising a plurality of openings formed between nodes and connecting ligaments of the nonwoven material and providing a percent open area for the apertured zone of the nonwoven material that is greater than 15%, as determined by the Material Sample Analysis Test Method;
- wherein the nonwoven material is coupled to the bodyside liner by a rear waist mechanical bond extending through the apertured zone and covering a primary rear waist bonding region, a rear waist adhesive bond extending through the apertured zone and covering a secondary rear waist bonding region which at least partially overlaps the primary rear waist bonding region, and a front waist bond extending through the apertured zone and covering a front waist bonding region that is spaced from the primary rear waist bonding region and the secondary rear waist bonding region,
- wherein:
  - the front waist bonding region has a length that is between 20% and 50% of the material length,
  - the primary rear waist bonding region has a length that is between 2% and 10% of the material length, and
  - the secondary rear waist bonding region has a length that is between 2% and 10% of the material length.

12. The article of claim 10, wherein the secondary rear waist bonding region completely overlaps the primary rear waist bonding region.

13. The article of claim 10, wherein the secondary rear waist bonding region has rear bond region edge which is spaced from the nonwoven material rear edge by between 2 mm and 10 mm.

14. The article of claim 10, wherein the secondary rear waist bonding region has a rear bond region edge which is spaced from the nonwoven material rear edge by between 2 mm and 5 mm.

15. The article of claim 10, wherein the adhesive of the rear waist adhesive bond is disposed in an amount of between 10 gsm and 20 gsm.

16. The article of claim 10, wherein the adhesive of the rear waist adhesive bond is disposed in an amount of between 12 gsm and 18 gsm.

17. The article of claim 10, wherein the nonwoven material further comprises a first side zone and a second side zone, the first side zone and the second side zone each extending between the nonwoven material rear edge and the nonwoven material front edge, each of the first side zone and the second side zone being bonded to the bodyside liner by adhesive within side zone adhesive bonding regions.

18. The article of claim 16, wherein the adhesive within the side zone adhesive bonding regions is disposed in an amount of between 6.5 gsm and 12.5 gsm.

19. The article of claim 10, wherein the secondary rear waist bonding region has a length that is between 2% and 5% of the material length.

* * * * *